US007892756B2

(12) United States Patent
Brand et al.

(10) Patent No.: US 7,892,756 B2
(45) Date of Patent: Feb. 22, 2011

(54) HUMAN SALTY TASTE RECEPTOR AND METHODS OF MODULATING SALTY TASTE PERCEPTION

(75) Inventors: Joseph G. Brand, Wayne, PA (US); Taufiqul Huque, Philadelphia, PA (US)

(73) Assignee: Monell Chemical Senses Center, Philadelphia, PA (US)

( * ) Notice: Subject to any disclaimer, the term of this patent is extended or adjusted under 35 U.S.C. 154(b) by 124 days.

(21) Appl. No.: 11/875,200

(22) Filed: Oct. 19, 2007

(65) Prior Publication Data
US 2008/0108148 A1 May 8, 2008

Related U.S. Application Data

(60) Provisional application No. 60/853,290, filed on Oct. 19, 2006.

(51) Int. Cl.
G01N 33/53 (2006.01)
(52) U.S. Cl. .................................................. 435/7.1
(58) Field of Classification Search ................... None
See application file for complete search history.

(56) References Cited

U.S. PATENT DOCUMENTS

| 5,693,756 A | 12/1997 | Li et al. |
| 2004/0072254 A1 | 4/2004 | Callamaras et al. |
| 2004/0624757 | 11/2004 | Stamou et al. |
| 2005/0059094 A1 | 3/2005 | Servant et al. |
| 2006/0035315 A1 | 2/2006 | Yue et al. |
| 2006/0094053 A1 | 5/2006 | Stamou et al. |
| 2010/0009385 A1 | 1/2010 | Moyer et al. |

FOREIGN PATENT DOCUMENTS

| WO | WO 02/087306 | 11/2002 |
| WO | WO 2006/013109 A1 | 2/2006 |
| WO | 2006/082110 A2 | 8/2006 |
| WO | WO 2006/105985 A1 | 10/2006 |
| WO | WO 2007/057428 A1 | 5/2007 |
| WO | 2007/092185 A2 | 8/2007 |

OTHER PUBLICATIONS

Ji et al., "delta Subunit Confers Novel Biophysical Features to alpha, beta, gamma-Human Epithelial Sodium Channel (ENaC) via a Physical Interaction," The Journal of Biological Chemistry, Mar. 2006, 281(12), 8233-8241; p. 8240, vol. 2; Fig. 9 and the abstract.
Babini et al., "A New Subunit of the Epithelial Na+ Channel Identifies Regions Involved in Na+ Self-Inhibition," Journal of Biological Chemistry, May 2003, 278(31), 28418-28426; p. 28418, col. 1 and 2 and the abstract.
UniProtKB/Swiss-Prot Entry P51172. UniProtKB/Swiss-Prot [online] Oct. 17, 2006 [retrieved on Apr. 19, 2008] Retrieved from the Internet URL: <http://www.expasy.ch/uniprot/P51172>; p. 1-5, especially p. 4 and 5.
Applied Biosystems Product Bulletin, Reverse Transcription PCR, "High Capacity cDNA Reverse Transcription Kit." (Jun. 2006).

Brand et al., "Inhibition by amiloride of chorda tympani responses evoked by monovalent salts," (1985) Brain Res. 334:207-214.
Breslin et al., "Human taste: peripheral anatomy, taste transduction, and coding," (2006) Adv. Otorhinolaryngol. 63:152-190.
Caldwell, R. A. et al., "Neutrophil elastase activates near-silent epithelial Na+ channels and increases airway epithelial Na+ transport," (2005) Am. J. Physiol. Lung Cell Mol. Physiol. 288:L813-L819.
Canessa, C. M. et al. "Amiloride-sensitive epithelial Na+ channel is made of three homologous subunits," (1994) Nature 367:463-467.
Carrattino, M. D. et al., "Mutations in the Pore Region Modify Epithelial Sodium channel Gating by Shear Stress," The Journal of Biological Chemistry, Feb. 11, 2005, 280(6), 4393-4401.
Daniells, S., "Nestle taste research may benefit salt reduction," Apr. 23, 2007.
de Planque, M.R.R. et al., "Controlled delivery of membrane proteins to artificial lipid bilayers by nystatin-ergosterol modulated vesicle fusion," IEE Proc-Nanobiotechnol, Apr. 2006, 153(2), 21-30.
Feigin, A. M. et al., "Enhancement of gustatory nerve fibers to NaCl and formation of ion channels by commercial novobiocin," (1994) Am. J. Physiol. 266:C1165-72.
Firsov, D. et al., "The heterotetrameric architecture of the epithelial sodium channel (ENaC)," (1998) EMBO J. 17 (2):344-352.
Gill, S. et al., "Flux assays in high throughput screening of ion channels in drug discovery," (2003) Assay Drug Dev. Technol. 1:709-717.
Grosvenor, W. et al,. "Biochemical enrichment and biophysical characterization of a taste receptor for L-arginine from the catfish, *Ictalurus puntatus*,"(2004) BMC Neurosci. 5:2202-2205.
Halpern, B. P. et al., "Amiloride and vertebrate gustatory responses to NaCl," (1998) Neurosci. Biobehav. Rev. 23 (1):5-47.
Mano, I. et al., "DEG/ENaC channels: a touchy superfamily that watches its salt," (1999) Bioessays 21:568-578.
Mierson, S. et al., "Basolateral amiloride-sensitive Na+ transport pathway in rat tongue epithelium," (1996) J. Neurophysiol. 76:1297-1309.
Nagel, G et al., "CTFR fails to inhibit the epithelial sodium channel ENaC expressed in *Xenopus laevis* oocytes," (2005) J. Physiol. 564(Pt 3):671-678.
Rao, U. S. et al. (2002) "Activation of Large Conductance Sodium Channels Upon Expression of Amiloride-Sensitive Sodium Channel in SF9 Insect Cells" J. Biol. Chem. 277(7):4900-4905.
Schoenfeld, M. A. et al., "Functional magnetic resonance tomography correlates of taste perception in the human primary taste cortex," (2004) Neuroscience. 127:347-353.

(Continued)

*Primary Examiner*—Michael Pak
(74) *Attorney, Agent, or Firm*—Woodcock Washburn LLP

(57) ABSTRACT

Methods for identifying modulators of the epithelial sodium ion channel and for identifying modulators of salty taste perception are described. Also featured are isolated human salty taste receptors, artificial lipid bilayers comprising an epithelial sodium ion channels, and kits for practicing the claimed methods.

11 Claims, 15 Drawing Sheets

OTHER PUBLICATIONS

Sheng, S. et al., "Characterization of the Selectivity Filter of the Epithelial Sodium Channel," (2000) J. Biol. Chem. 275 (12):8572-8581.

Spielman, A. I. et al. "Collection of taste tissue from mammals," Experimental Cell Biology of Taste and Olfaction. Spielman AI and Brand JG eds. CRC Press, Boca Raton, FL, pp. 25-32, 1995.

Staruschenko, A. et al., "Epithelial Na+ Channel Subunit Stoichiometry," (2005) Biophys. J. 88:3966-3975.

Staruschenko, A. et al., "Fluorescence Resonance Energy Transfer Analysis of Subunit Stoichiometry of the Epithelial Na+ Channel," (2004) J. Biol. Chem. 279(26):27729-27734.

Tong, Q. et al., "Direct Activation of the Epithelial Na+ Channel by Phosphatidylinositol 3,4,5-Trisphosphate and Phosphatidylinositol 3,4-Bisphosphate Produced by Phosphionositide 3-OH Kinase," (2004) J. Biol. Chem. 279 (21):22654-22663.

Waldman, R. et al., "Molecular Cloning and Functional Expression of a Novel Amiloride-sensitive Na+ Channel," (1995) J. Biol. Chem. 270(46):27411-27414.

Abankwa, et al., "A FRET Map of Membrane Anchors Suggests Distinct Microdomains of Heterotrimeric G Proteins", Journal of Cell Science, Aug. 15, 2007, 120(16), 2953-2962.

Berdiev, et al., "Epithelial Sodium Channel in Planar Lipid Bilayers", Ion Channels: Methods and Protocols (Methods in Molecular Biology), Humana Press, First Edition, Apr. 17, 2006, 337(Chapter 8), 89-99.

Bolinger, et al., "An Integrated Self-Assembled Nanofluidic System for Controlled Biological Chemistries", Angewandte Chemie, International Edition, Jul. 9, 2008, 47(30), 5544-5549.

Cook, et al., "Large-Scale and Study of a Synthetic G Protein-Coupled Receptor: Human Olfactory Receptor 17-4", Department of Biological Engineering and Center for Biomedical Engineering, MIT, Proceedings of the National Academy of Sciences of the United States of America, Jul. 6, 2009, 106(29), 11925-11930.

Danelon et al., "Modulation of Proton-Induced Current Fluctuations in the Human Nicotinic Acetylcholine Receptor Channel", Biochimica et Biophysica Acta, Biomembranes, Jan. 2007, 1768(1), 76-89.

Danelon, et al., "Fabrication and Functionalization of Nanochannels by Electron-Bean-Induced Silicon Oxide Deposition", Langmuir, Dec. 5, 2006, 22-(25), 10711-10715.

Danelon, et al., "Micro-and Nanostructured Devices for the Investigation of Biomolecular Interactions", Chimia, Nov. 2006, 60(11), 754-760.

Danelon, et al., "Probing the Function of Ionotropic and G-Protein-Coupled Receptors in Surface-Confined Membranes", Methods, Oct. 2008, 46(2), 104-115.

Gopalakrishnan, et al., "Multifunctional Lipid/Quantum Dot Hybrid Nanocontainers for Controlled Targeting of Live Cells", Angewandte Chemie, International Edition, Jul. 18, 2006, 45(33), 5478-5483.

Grandl, et al., "Fluorescent Epibatidine Agonists for Neuronal and Muscle-Type Nicotinic Acetylcholine Receptors", Angewandte Chemie, International Edition, Mar. 27, 2007, 46(19), 3505-3508.

Grandl, et al., "Functional Asymmetry of Transmembrane Segments in Nicotinic Acetylcholine Receptors", European Biophysics Journal, Oct. 2006, 35(8), 685-693.

Guignet, et al., "Repetitive Reversible Labeling of Proteins at Polyhistiden Sequences for Single-Molecule Imaging in Live Cells", ChemPhysChem, Jun. 4, 2007, 8(8), 1221-1227.

Hovius, et al., "Fluorescent Labeling of Membrane Proteins in Living Cells", Structural Genomics of Membrane Proteins, CRC Press, First Edition, Feb. 23, 2006, Chapter 12, 199-210.

Ismailov, et al., "Identification of an Amilroide Binding Domain Within the α-Subunit of the Epithelial Na$^+$ Channel", Journal of Biological Chemistry, Aug. 22, 1997, 272(34), 21075-21083.

Jacquier, et al., "Characterization of an Extended Receptive Ligand Repertoire of the Human Olfactory Receptor OR17-40 Comprising Structurally Related Compounds", Journal of Neurochemistry, Mar. 15, 2006, 97(2), 537-544.

Jenke, et al., "Micropositioning and Microscopic Observation of Individual Picoliter-Sized Containers Within SU-8 Microchannels", Microfluidics and Nanofluidics, Apr. 2007, 3(2), 189-194.

Merenda, et al., "Refractive Multiple Optical Tweezers for Parallel Biochemical Analysis in Micro-Fluidics", Proceedings of SPIE-The International Society for Optical Engineering, Jan. 24, 2007, 6483, 64830A/1-64830A/9.

Meyer, et al., "Covalent Labeling of Cell-Surface Proteins for In-Vivo FRET Studies", FEBS Letters, Mar. 6, 2006, 580(6), 1654-1658.

Meyer, et al., "FRET Imaging Reveals That Functional Neurokinin-1 Receptors are Monomeric and Reside in Membrane Microdomains of Live Cells", Proceedings of the National Academy of Sciences of the United States of America, Feb. 14, 2006, 103(7), 2138-2143.

Minelli, et al., "Organization of Nanoparticles on Hard Substrates Using Block Copolymer Films as Templates", Journal of Nanoscience and Nanotechnology, Jun. 2006, 6(6), 1611-1619.

Perez, et al., "Monitoring the Diffusion of Single Heterotrimeric G. Proteins in Supported Cell-Membrane Sheets Reveals Their Partitioning into Microdomains", Journal of Molecular Biology, Nov. 10, 2006, 363(5), 918-930.

Perez, et al., "Supported Cell-Membrane Sheets for Functional Fluorescence Imaging of Membrane Proteins", Advanced Functional Materials, Jan. 9, 2006, 16(2), 306-312.

Pick, et al., "Distribution Plasticity of the Human Estrogen Receptor α in Live Cells: Distinct Imaging of Consecutively Expressed Receptors", Journal of Molecular Biology, Dec. 14, 2007, 374(5), 1213-1223.

Pick, et al., "Dual Activities of Odorants on Olfactory and Nuclear Hormone Receptors", Journal of Biological Chemistry, Oct. 30, 2009, 284(44), 30547-30555.

Prummer, et al., "Mobility and Signaling of Single Receptor Proteins", Springer Series in Biophysics, Single Molecules and Nanotechnology, Springer, First Edition, Jan. 8, 2008, 12(Chapter 6), 131-162.

Prummer, et al., "Post-Translational Covalent Labeling Reveals Heterogeneous Mobility of Individual G. Protein-Coupled Receptors in Living Cells", ChemBioChem, Apr. 11, 2006, 7(6), 908-911.

Rao, et al., "Activation of Large Conductance Sodium Channels Upon Expression of Amiloride-Sensitive Sodium Channel in Sf9 Insect Cells", Journal of Biological Chemistry, vol. 277, No. 7, Issue of Feb. 15, 2002, 4900-4905.

Riera, et al., "Artificial Sweeteners and Salts Producing A Metallic Taste Sensation Activate TRPV1 Receptors", American Journal of Physiology, Jun. 2, 2007, 293(2, Pt. 2), R626-R634.

Riera, et al., "Sensory Attributes of Complex Tasting Divalent Salts are Mediated by TRPM5 and TRPV1 Channels", Journal of Neuroscience, Feb. 25, 2009, 29(8), 2654-2662.

Riera, et al., "The Capsaicin Receptor Participates in Artificial Sweetener Aversion", Biochemical and Biophysical Research Communications, Nov. 28, 2008, 376(4), 653-657.

Sakr, et al., "Engineered Site-Directed Labeling of Nicotinic Acetylcholine Receptors Using Reactive Epibatidine Derivatives: Appraisal of Epibatidine-Docking Models in Neuronal and Muscular Receptors", Journal of Molecular Neuroscience, Feb. 2006, 30(1-2), 35-36.

Segura, et al., "Increased Mobility of Major Histocompatibility Complex I-Peptide Complexes Decreases the Sensitivity of Antigen Recognition", Journal of Biological Chemistry, Jun. 25, 2008, 283(35), 24254-24263.

Terrettaz, et al., "A Synthetic Membrane Protein in Tethered Lipid Bilayers for Immunosensing in Whole Blood", Journal of Structural Biology, Oct. 2009, 168(1), 177-182.

Zava, et al., "A Cytotoxic Tris(Bipyridyl) Complex That Accumulates at Plaza Membranes", Swiss Federal Institute of Technology, ChemBioChem, Jun. 25, 2009, 10(11), 1796-1800.

Ismailov et al., "Triple-barrel organization of ENaC, a cloned epithelial Na+ channel" Journal of Biological Chemistry, Jan. 12, 1996, 271(2), 807-816.

Awayda et al., "Protein kinase regulation of a cloned epithelial Na+ channel" Journal of General Physiology, Jul. 1996, 108(1), 49-65.

Rao et al., "Expression of amiloride-sensitive, sodium channel: A strategy for the coexpression of multimeric membrane protein in Sf9 insect cells" Analytical Biochemistry, Academic Press Inc, New York, Nov. 15, 2000, 286(2), 206-213.

Oh et al., "Rapid purification of an amiloride-sensitive sodium channel from bovine kidney and its functional reconstitution" Protein Expression and Purification, Aug. 1993, 4(4), 312-319.

Awayda et al., "A cloned renal epithelial Na+ channel protein displays stretch activation in planar lipid bilayers" American Journal of Physiology, American Physiological Society, Bethesda, MD, US, Jan. 1, 1995, 268(6 part 1), C1450-C1459.

Ji et al., "delta-subunit confers novel biophysical features to alpha beta gamma-human epithelial sodium channel (ENaC) via a physical interaction" Journal of Biological Chemistry, Mar. 24, 2006, 281(12), 8233-8241.

Grosvenor et al., "Biochemical enrichment and biophysical characterization of a taste receptor for L-arginine from the catfish, *Ictalurus puntatus*" BMC Neuroscience, Biomed Central, London, GB, Jul. 28, 2004, 5(1), 25.

Ji et al., "The role of pre-H2 domains of alpha- and delta-epithelial Na+ channels in ion permeation, conductance, and amiloride sensitivity." Journal of Biological Chemistry, Feb. 27, 2004 279(9), 8428-8440.

```
DENACGB  1  MAEHRSMDGRMEAATRGGSHLQAAAQTPPRPGPPSAPPPPPKEGHQEGLVELPASFRELLTFFCTNATIHGAIRLVCSRG
DENACA   1  MAEHRSMDGRMEAATRGGSHLQAAAQTPPRPGPPSAPPPPPKEGHQEGLVELPASFRELLTFFCTNATIHGAIRLVCSRG
DENACD   1  MAEHRSMDGRMEAATRGGSHLQAAAQTPPRPGPPSAPPPPPKEGHQEGLVELPASFRELLTFFCTNATIHGAIRLVCSRG
DENACE   1  MAEHRSMDGRMEAATRGGEHLQAAAQTPPRPGPPSAPPPPPKEGHQEGLVELPASFRELLTFFCTNATIHGAIRLVCSRG
DENACG   1  MAEHRSMDGRMEAATRGGSHLQAAAQTPPRPGPPSAPPPPPKEGHQEGLVELPASFRELLTFFCTNATIHGAIRLVCSRG
DENACH   1  MAEHRSMDGRMEAATRGGSHLQAAAQTPPRPGPPSAPPPPPKEGHQEGLVELPASFRELLTFFCTNATIHGTIRLVCSRG
DENACI   1  MAEHRSMDGRMEAATRGGSHLQAAAQTPPRPGPPSAPPPPPKEGHQEGLVELPASFRELLTFFCTNATIHGAIRLVCSRG
DENACJ   1  MAEHRSMDGRMEAATRGGSHLQAAAQTPPRPGPPSAPPPPPKEGHQEGLVELPASFRELLTFFCTNATIHGAIRLVCSRG
DENACT   1  MAEHRSMDGRMEAATRGGSHLQAAAQTPPRPGPPSAPPPPPKEGHQEGLVELPASFRELLTFFCTNATIHGAIRLVCSRG
DENACV   1  MAEHRSMDGRMEAATRGGSHLQAAAQTPPRPGPPSAPPPPPKEGHQEGLVELPASFRELLTFFCTNATIHGAIRLVCSRG
DENACW   1  MAEHRSMDGRMEAATRGGSHLQAAAQTPPRPGPPSAPPPPPKEGHQEGLVELLTFFCTNATIHGAIRLVCSRG

DENACGB  81  NRLKTTSWGLLSLGALVALCWQLGLLFERHWHRPVLMAVSVHSERKLLPLVTLCDGNPRRPSPVLRHLELLDEFARENID
DENACA   81  NRLKTTSWGLLSLGALVALCWQLGLLFERHWHRPVLMAVSVHSERKLLPLVTLCDGNPRRPSPVLRHLELLDEFARENID
DENACD   81  NRLKTTSWGLLSLGALVALCWQLGLLFERHWHRPVLMAVSVHSERKLLPLVTLCDGNPRRPSPVLRHLELLDEFARENID
DENACE   81  NRLKTTSWGLLSLGALVALCWQLGLLFERHWHRPVLMAVSVHSERKLLPLVTLCDGNPRRPSPVLRHLELLDEFARENID
DENACG   81  NRLKTTSWGLLSLGALVALCWQLGLLFERHWHRPVLMAVSVHSERKLLPLVTLCDGNPRRPSPVLRHLELLDEFARENID
DENACH   81  NRLKTTSWGLLSLGALVALCWQLGLLFERHWHRPVLMAVSVHSERKLLPLVTLCDGNPRRPSPVLRHLELLDEFARENID
DENACI   81  NRLKTTSWGLLSLGALVALCWQLGLLFERHWHRPVLMAVSVHSERKLLPLVTLCDGNPRRPSPVLRHLELLDEFARENID
DENACJ   81  NRLKTTSWGLLSLGALVALCWQLGLLFERHWHRPVLMAVSVHSERKLLPLVTLCDGNPRRPSPVLRHLELLDEFARENID
DENACT   81  NRLKTTSWGLLSLGALVALCWQLGLLFERHWHRPVLMAVSVHSERKLLPLVTLCDGNPRRPSPVLRHLELLDEFARENID
DENACV   81  NRLKTTSWGLLSLGALVALCWQLGLLFERHWHRPVLMAVSVHSERKLLPLVTLCDGNPRRPSPVLRHLELLDEFARENID
DENACW   81  NRLKTTSWGLLSLGALVALCWQLGLLFERHWHRPVLMAVSVHSERKLLPLVTLCDGNPRRPSPVLRHLELLDEFARENID
```

Figure 3A

```
DENACGB  161  SLYNVNLSKGRAALSATVPRHEPPFHLDREIRLQRLSHSGSRVRVGFRLCNSTGGDCFYRGYTSGVAAVQDWYHFHYVDI
DENACA   161  SLYNVNLSKGRAALSATVPRHEPPFHLDREIRLQRLSHSGSRVRVGFRLCNSTGGDCFYRGYTSGVAAVQDWYHFHYVDI
DENACD   161  SLYNVNLSKGRAALSATVPRHEPPFHLDREIRLQRLSHSGSRVRVGFRLCNSTGGDCFYRGYTSGVAAVQDWYHFHYVDI
DENACE   161  SLYNVNLSKGRAALSATVEHEPPFHLDREIRLSLSHSGSRVRVGFRLCNSTGGDCFYRGYTSGVAAVQDWYHFHYVDI
DENACG   161  SLYNVNLSKGRAALSATVPRHEPPFHLDREIRLQRLSHSGSRVRVGFRLCNSTGGDCFYRGYTSGVAAVQDWYHFHYVDI
DENACH   161  SLYNVNLSKGRAALSATVEHEPPFHLDREIRLQRLSHSGSRVRVGFRLCNSTGGDCFYRGYTSGVAAVQDWYHFHYVDI
DENACI   161  SLYNVNLSKGRAALSATVPRHEPPFHLDREIRLQRLSHSGSRVRVGFRLCNSTGGDCFYRGYTSGVAAVQDWYHFHYVDI
DENACJ   161  SLYNVNLSKGRAALSATVEHEPPFHLDREIRLQRLSHSGSRVRVGFRLCNSTGGDCFYRGYTSGVAAVQDWYHFHYVDI
DENACT   161  SLYSVNLSKGRAALSATVPRHEPPFHLDREIRLQRLSHSGSRVRVGFRLCNSTGGDCFYRGYTSGVAAVQDWYHFHYVDI
DENACV   161  SLYNVNLSKGRAALSATVPRHEPPFHLDREIRLQRLSHSGSRVRVGFRLCNSTGGDCFYRGYTSGVAAVQDWYHFHYVDI
DENACW   161  SLYNVNLSKGRAALSATVPRHEPPFHLDREIRLQRLSHSGSRVRVGFRLCNSTGGDCFYRGYTSGVAAVQDWYHFHYVDI

DENACGB  241  LALLPAAWEDSHGSQDGHFVLSCSYDGLDCQARQFRTFHHPTYGSCYTVDGVWTAQRPGITHGVGLVLRVEQQPHLPLLS
DENACA   241  LALLPAAWEDSHGSQDGHFVLSCSYDGLDCQARQFRTIHHPTYGSCYTVDGVWTAQRPGITHGVGLVLRVEQQPHLPLLS
DENACD   241  LALLPAAWEDSHGSQDGHFVLSCSYDGLDCQARQFRTFHHPTYGSCYTVDGVWTAQRPGITHGVGLVLRVEQQPHLPLLS
DENACE   241  LALLPAAWEDSHGSQDGHFVLSCSYDGLDCQARQFRTFHHPTYGSCYTVDGVWTAQRPGITHGVGLVLRVEQQPHLPLLS
DENACG   241  LALLPAAWEDSHGSQDGHFVLSCSYDGLDCQARQFRTFHHPTYGSCYTVDGVWTAQRPGITHGVGLVLRVEQQPHLPLLS
DENACH   241  LALLPAAWEDSHGSQDGHFVLSCSYDGLDCQARQFRTFHHPTYGSCYTVDGVWTAQRPGITHGVGLVLRVEQQPHLPLLS
DENACI   241  LALLPAAWEDSHGSQDGHFVLSCSYDGLDCQARQFRTFHHPTYGSCYTVDGVWTAQRPGITHGVGLVLRVEQQPHLPLLS
DENACJ   241  LALLPAAWEDSHGSQDGHFVLSCSYDGLDCQARQFRTFHHPTYGSCYTVDGVWTAQRPGITHGVGLVLRVEQQPHLPLLS
DENACT   241  LALLPAAWEDSHGSQDGHFVLSCSYDGLDCQARQFRTFHHPTYGSCYTVDGVWTAQRPGITHGVGLVLRVEQQPHLPLLS
DENACV   241  LALLPAAWEDSHGSQDGHFVLSCSYDGLDCQARQFRTFHHPTYGSCYTVDGVWTAQRPGITHGVGLVLRVEQQPHLPLLS
DENACW   241  LALLPAAWEDSHGSQDGHFVLSCSYDGLDCQARQFRTTHHPTYGSCYTVDGVWTAQRPGITHGVGLVLRVEQQPHLPLLS
```

Figure 3B

```
DENACGB  321 TLAGIRVMVHGRNHTPFLGHHSFSVRPGTEATISIREDEVHRLGSPYGHCTAGGEGVEVELLHNTSYTRQACLVSCFQQL
DENACA   321 TLAGIRVMVHGRNHTPFLGHHSFSVRPGTEATIRIREDEVHRLGSPYGHCTAGGEGVEVELLHNTSYTRQACLVSCFQQL
DENACD   321 TLAGIRVMVHGRNHTPFLGHHSFSVRPGTEATISIREDEVHRLGSPYGHCTAGGEGVEVELLHNTSYTRQACLVSCFQQL
DENACE   321 TLAGIRVMVHGRNHTPFLGHHSFSVRPGTEATISIREDEVHRLGSPYGHCTAGGEGVEVELLHNTSYTRQACLVSCFQQL
DENACG   321 TLAGIRVMVHGRNHTPFLGHHSFSVRPGTEATISIREDEVHRLGSPYGHCTAGGEGVEVELLHNTSYTRQACLVSCFQQL
DENACH   321 TLAGIRVMVHGRNHTPFLGHHSFSVRPGTEATISIREDEVHRLGSPYGHCTAGGEGVEVQLLHNTSYTRQACLVSCFQQL
DENACI   321 TLAGIRVMVHGRNHTPFLGHHSFSVRPGTEATISIREDEVHRLGSPYGHCTAGGEGVEVELLHNTSYTRQACLVSCFQQL
DENACJ   321 TLAGIRVMVHGRNHTPFLGHHSFSVRPGTEATISIREDEVHRLGSPYGHCTAGGEGVEVQELHNTSYTRQACLVSCFQQL
DENACT   321 TLAGIRVMVHGRNHTPFLGHHSFSVRPGTEATISIREDEVHRLGSPYGHCTAGGEGVEVELLHNTSYTRQPCLVSCFQQL
DENACV   321 TLAGIRVMVHGRNHTPFLGHHSFSVRPGTEATISIREDEVHRLGSPYGHCTAGGEGVEVELLHNTSYTRQACLVSCFQQL
DENACW   321 TLAGIRVMVHGRNHTPFLGHHSFSVRPGTEATIRIREDEVHRLGSPYGHCTAGGEGVEVELLHNTSYTRQACLVSCFQQL

DENACGB  401 MVETCSCGYYLHPLPAGAEYCSSARHPAWGHCFYRLYQDLETHRLPCTSRCPRPCRESAFKLSTGTSRWPSAKSAGWTLA
DENACA   401 MVETCSCGYYLHPLPAGAEYCSSARHPAWGHCFYRLYQDLETHRLPCTSRCPRPCRESAFKLSTGTSRWPSAKSAGWTLA
DENACD   401 MVETCSCGYYLHPLPAGAEYCSSARHPAWGHCFYRLYQDLETHRLPCTSRCPRPCRESAFKLSTGTSRWPSAKSAGWTLA
DENACE   401 MVETCSCGYYLHPLPAGAEYCSSARHPAWGHCFYRLYQDLETHRLPCTSRCPRPCRESAFKLSTGTSRWPSAKSAGWTLA
DENACG   401 MVETCSCGYYLHPLPAGAEYCSSARHPAWGHCFYRLYQDLETHRLPCTSRCPRPCRESAFKLSTGTSRWPSAKSAGWTLA
DENACH   401 MVETCSCGYYLHPLPAGAEYCSSARHPAWGHCFYRLYRDLETHRLPCTSRCPRPCRESAFKLSTGTSRWPSAKSAGWTLA
DENACI   401 MVETCSCGYYLHPLPAGAEYCSSARHPAWGHCFYRLYQDLETHRLPCTSRCPRPCRESAFKLSTGTSRWPSAKSAGWTLA
DENACJ   401 MVETCSCGYYLHPLPAGAEYCSSARHPAWGHCFYRLYQDLETHRLPCTSRCPRPCRESAFKLSTGTSRWPSAKSAGWTLA
DENACT   401 MVETCSCGYYLHPLPAGAEYCSSARHPAWGHCFYRLYQDLETHRLPCTSRCPRPCRESAFKLSTGTSRWPSAKSAGWTLA
DENACV   401 MVETCSCGYYLHPLPAGAEYCGSARHPAWGHCFYRLYQDLETHRLPCTSRCPRPCRESAFKLSTGTSRWPSAKSAGWTLA
DENACW   401 MVETCSCGYYLHPLPAGAEYCSSARHPAWGHCFYRLYQDLETHRLPCTSRCPRPCRESAFKLSTGTSRWPSAKSAGWTLA
```

Figure 3C

```
DENACGB  481  TLGEQGLPHQSHRQRSSLAKINIVYQELNYRSVEEAPVYSVPQLLSAMGSLYSLWFGASVLSLLELLELLLDASALTLVL
DENACA   481  TLGEQGLPHQSHRQRSSLAKINIVYQELNYRSVEEAPVYSVPQLLSAMGSLCSLWFGASVLSLLELLELLLDASALTLVL
DENACD   481  TLGEQGLPHQSHRQRSSLAKINIVYQELNYRSVEEAPVYSVPQLLSAMGSLCSLWFGASVLSLLELLELLLDASALTLVL
DENACE   481  TLGEQGLPHQSHRQRSSLAKINIVYQELNYRSVEEAPVYSVPQLLSAMGSLCSLWFGASVLSLLELLELLLDASALTLVL
DENACG   481  TLGEQGLPHQSHRQRSSLAKINIVYQGLNYRSVEEAPVYSVPQLLSAMGSLCSLWFGASVLSLLELLELLLDASALTLVL
DENACH   481  TLGEQGLPHQSHRQRSSLAKINIVYQELNYRSVEEAPVYSVPQLLSAMGSLCSLWFGASVLSLLELLELLLDASALTLVL
DENACI   481  TLGEQGLPHQGHRQRSSLAKINIVYQELNYRSVEEAPVYSVPQLLSAMGSLCSLWFGASVLSLLELLELLLDASALTLVL
DENACJ   481  TLGEQGLPHQSHRQRSSLAKINIVYQELNYRSVEEAPVYSVPQLLSAMGSLCSLWFGASVLSLLELLELLLDASALTLVL
DENACT   481  TLGEQGLPHQSHRQRSSLAKINIVYQELNYRSVEEAPVYSVPQLLSAMGSLCSLWFGASVLSLLELLELLLDASALTLVL
DENACV   481  TLGEQGLPHQSHRQRSSLAKINIVYQELNYRSVEEAPVYSVPQLLSAMGSLCSLWFGASVLSLLELLELLLDASALTLVL
DENACW   481  TLGEQGLPHQSHRQRSSLAKINIVYQELNYRSVEEAPVYSVPQLLSAMGSLCSLWFGASVLSLLELLELLLDASALTLVL

DENACGB  561  GGRRLRRAWFSWPRASPASGASSIKPEASQMPPPAGGTSDDPEPSGPHLPRVMLPGVLAGVSAEESWAGPQPLETLDT
DENACA   561  GGRRLHRAWFSWPRASPASGASSIKPEASQMPPPAGGTSDDPEPSGPHLPRVMLPGVLAGVSAEESWAGPQPLETLDT
DENACD   561  GGRRLRRAWFSWPRASPASGASSIKPEASQMPPPAGGTSDDPEPSGPHLPRVMLPGVLAGVSAEESWAGPQPLETLDT
DENACE   561  GGRRLRRAWFSWPRASPASGASSIKPEASQMPPPAGGTSDDPEPSGPHLPRVMLPGVLAGVSAEESWAGPQPLETLDK
DENACG   561  GGRRLRRAWFSWPRASPASGASSIKPEASQMPPPAGGTSDDPEPSGPHLPRVMLPGVLAGVSAEESWAGPQPLETLDT
DENACH   561  GGRRLRRAWFSWPRASPASGASSIKPEAGQMPPPAGGTSDDPEPSGPHLPRVMLPGVLAGVSAEESWAGPQPLETLDT
DENACI   561  GGRRLRRAWFSWPRASPASGASSIKPEASQMPPPAGGTSDDPEPSGPHLPRVMLPGVLAGVSAEESWAGPQPLETLDT
DENACJ   561  GGRRLRRAWFSWPRASPASGASSIKPEASQMPPPAGGTSDDPEPSGPHLPRVMLPGVLAGVSAEESWAGPQPLETLDT
DENACT   561  GGRRLRRAWFSWPRASPASGASSIKPEASQMPPPAGGTSDDPEPSGPHLPRVMLPGVLAGVSAEESWAGPQPLETLDT
DENACV   561  GGRRLRRAWFSWPRASPASGASSIKPEASQMPPPAGGTSDDPEPSGPHLPRVMLPGVLAGVSAEESWAGPQPLETLDT
DENACW   561  GGRRLHRAWFSWPRASPASGASSIKPEASQMPPPAGGTSDDPEPSGPHLPRVMLPGVLAGVSAEESWAGPQPLETLDT
```

Figure 3D

```
GENACGB   1  MAPGEKIKAKIKKNLPVTGPQAPTIKELMRWYCLNTNTHGCRRIVVSRGRLRRLLWIGFTLTAVALILWQCALLVFSFYT
GENACA    1  MAPGEKIKAKIKKNLPVTGPQAPTIKELMRWYCLNTNTHGCRRIVVSRGRLRRLLWIGFTLTAVALILWQCALLVFSFYT
GENACB    1  MAPGEKIKAKIKKNLPVTGPQAPTIKELMRWYCLNTNTHGCRRIVVSRGRLRRLLWIGFTLTAVALILWQCALLVFSFYT
GENACD    1  MAPGEKIKAKIKKNLPVTGPQAPTIKELMRWYCLNTNTHGCRRIVVSRGRLRRLLWIGFTLTAVALILWQCALLVFSFYT
GENACE    1  MAPGEKIKAKIKKNLPVTGPQAPTIKELMRWYCLNTNTHGCRRIVVSRGRLRRLLWIGFTLTAVALILWQCALLVFSFYT
GENACG    1  MAPGEKIKAKIKKNLPVTGPQAPTIKELMRWYCLNTNTHGCRRIVVSRGRLRRLLWIGFTLTAVALILWQCALLVFSFYA
GENACH    1  MAPGEKIKAKIKKNLPVTGPQAPTIKELMRWYCLNTNTHGCRRIVVSRGRLRRLLWIGFTLTAVALILWQCALLVFSFYT
GENACJ    1  MAPGEKIKAKIKKNLPVTGPQAPTIKELMRWYCLNTNTHGCRRIVVSRGRLRRLLWIGFTLTAVALILWQCALLVFSFYT
GENACT    1  MAPGEKIKAKIKKNLPVTGPQAPTIKELMRWYCLNTNTHGCRRIVVSRGRLRRLLWIGSTLTAVALILWQCALLVFSFYT
GENACV    1  MAPGEKIKAKIKKNLPVTGPQAPTIKELMRWYCLNTNTHGCRRIVVSRGRLRRLLWIGFTLTAVALILWQCALLVFSFYT
GENACW    1  MAPGEKIKAKIKKNLPVTGPQAPTIKELMRWYCLNTNTHGCRRIVVSRGRLRRLLWIGFTLTAVALILRQCALLVFSFYT

GENACGB  81  VSVSIKVHFRKLDFPAVTICNINPYKYSTVRHLLADLEQETREALKSLYGFPESRKRREAESWNSVSEGKQPRFSHRIPL
GENACA   81  VSVSIKVNFRKLDFPAVTICNINPYKYSTVRHLLADLEQETREALKSLYGFPESRKRREAESWNSVSEGKQPRFSHRIPL
GENACB   81  VSVSIKVNFRKLDFPAVTICNINPYKYSTVRHLLADLEQETREALKSLYGFPESRKRREAESWNSVSEGKQPRFSHRIPL
GENACD   81  VSVSIKVHFRKLDFPAVTICNINPYKYSTVRHLLADLEQETREALKSLYGFPESRKRREAESWNSVSEGKQPRFSHRIPL
GENACE   81  VSVSIKVHFRKLDFPAVTICNINPYKYSTVRHLLADLEQETREALKSLYGFPESRKRREAESWNSVSEGKQPRFSHRIPL
GENACG   81  VSVSIKVHFRKLDFPAVTICNINPYKYSTVRHLLADLEQETREALKSLYGFPESRKRREAESWNSVSEGKQPRFSHRIPL
GENACH   81  VSVSIKVHFRKLDFPAVTICNINPYKYSTVRHLLADLEQETREALKSLYGFPESRKRREAESWNSVSEGKQPRFSHRIPL
GENACJ   81  VSVSIKVHFRKLDFPAVTICNINPYKYSTVRHLLADLEQETREALKSLYGFPESRKRREAESWNSVSEGKQPRFSHRIPP
GENACT   81  VSVSIKVHFRKLDFPAVTICNINPYKYSTVRHLLADLEQETREALKSLYGFPESRKRREAESWNSVSEGKQPRFSHRIPL
GENACV   81  VSVSIKVHFRKLDFPAVTICNINPYKYSTVRHLLADLEQETREALKSLYGFPESRKRREAESWNSVSEGKQPRFSHRIPL
GENACW   81  VSVSIKVHFRKLDFPAVTICNINPYKYSTVRHLLADLEQETREALKSLYGFPESRKRREAESWNSVSEGKQPRFSHRIPL
```

Figure 8A

```
GENACGB  161 LIFDQDEKGKARDFFTGRKRKVGGSIIHKASNVMHIESKQVVGFQLCSNDTSDCATYTFSSGINAIQEWYKLHYMNIMAQ
GENACA   161 LIFDQDEKGKARDFFTGRKRKVGGSIIHKASNVMHIESKQVVGFQLCSNDTSDCATYTFSSGINAIQEWYKLHYMNIMAQ
GENACB   161 LIFDQDEKGKARDFFTGRKRKVGGSIIHKASNVMHIESKQVVGFQLCSNDTSDCATYTFSSGINAIQEWYKLHYMNIMAQ
GENACD   161 LIFDQDEKGKARDFFTGRKRKVGGSIIHKASNVMHIESKQVVGFQLCSNDTSDCATYTFSSGINAIQEWYKLHYMNIMAQ
GENACE   161 LIFDQDEKGEARDFFTGRKRKVGGSIIHKASNVMHIESKQVVGFQLCSNDTSDCATYTFSSGINAIQEWYKLHYMNIMAQ
GENACG   161 LIFDQDEKGKARDFFTGRKRKVGGSIIHKASNVMHIESKQVVGFQLCSNDTSDCATYTFSSGINAIQEWYKLHYMNIMAQ
GENACH   161 LIFDQDEKGKARDFFTGRKRKVGGSIIHKASNVMHIESKQVVGFQLCSNDTSDCATYTFSSGINAIQEWYKLHYMNIMAQ
GENACJ   161 LIFDQDEKGKARDFFTGRKRKVGGSIIHKASNVMHIESKQVVGFQLCSNDTSDCATYTFSLGINAIQEWYKLHYMNIMAQ
GENACT   161 LIFDQDEKGKARDFFTGRKRKVGGSIIHKASNVMHIESKQVVGFQLCSNDTSDCATYTFSSGINAIQEWYKLHYMNIMAQ
GENACV   161 LIFDQDEKGKARDFFTGRKRKVGGSIIHKASNVMHIESKQVVGFQLCSNDTSDCATYTFSSGINAIQEWYKLHYMNIMAQ
GENACW   161 LIFDQDEKGKARDFFTGRKRKVGGSIIHKASNVMHIESKQVVGFQLCSNDTSDCATYTFSSGINAIQEWYKLHYMNIMAQ

GENACGB  241 VPLEKKINMSYSAEELLVTCFFDGVSCDARNFTLFHHPMHGNCYTFNNRENETILSTSMGGSEYGLQVILYINEEEYNPF
GENACA   241 VPLEKKINMSYSAEELLVTCFFDGVSCDARNFTLFHHPMHGNCYTFNNRENETILSTSMGGSEYGLQVILYINEEEYNPF
GENACB   241 VPLEKKINMSYSAEELLVTCFFDGVSCDARNFTLFHHPMHGNCYTFNNRENETILSTSMGGSEYGLQVILYINEEEYNPF
GENACD   241 VPLEKKINMSYSAEELLVTCFFDGVSCDARNFTLFHHPMHGNCYTFNNRENETILSTSMGGSEYGLQVILYINEEEYNPF
GENACE   241 VPLEKKINMSYSAEELLVTCFFDGVSCDARNFTLFHHPMHGNCYTFNNRENETILSTSMGGSEYGLQVILYINEEEYNPF
GENACG   241 VPLEKKINMSYSAEELLVTCFFDGVSCDARNFTLFHHPMHGNCYTFNNRENETILSTSMGGSEYGLQVILYINEEEYNPF
GENACH   241 VPLEKKINMSYSAEELLVTCFFDGVSCDARNFTLFHHPMHGNCYTFNNRENETILSTSMGGSEYGLQVILYINEEEYNPF
GENACJ   241 VPLEKKINMSYSAEELLVTCFFDGVSCDARNFTLFHHPMHGNCYTFNNRENETILSTSMGGSEYGLQVILYINEEEYNPF
GENACT   241 VPLEKKINMSYSAEELLVTCFFDGVSCDARNFTLFHHPMHGNCYTFNNRENETILSTSMGGSEYGLQVILYINEEEYNPF
GENACV   241 VPLEKKINMSYSAEELLVTCFFDGVSCDARNFTLFHHPMHGNCYTFNNRENETILSTSMGGSEYGLQVILYINEEEYNPF
GENACW   241 VPLEKKINMSYSAEELLVTCFFDGVSCDARNFTLFHHPMHGNCYTFNNRENETILSTSMGGSEYGLQVILYINEEEYNPF
```

Figure 8B

```
GENACGB  321  LVSSTGAKVIIHRQDEYESVEDVGTEIETTMVTSIGMHLTESFKLSEPSSQCTFGGSDVPIRNIYNAAYSLQICLHSCFQ
GENACA   321  LVSSTGAKVIIHRQDEYPFVEDVGTEIETAMVTSIGMHLTESFKLSEPYSQCTEDGSDVPIRNIYNAAYSLQICLHSCFQ
GENACB   321  LVSSTGAKVIIHRQDEYPFVEDVGTEIETAMVTSIGMHLTESFKLSEPYSQCTEDGSDVPIRNIYNAAYSLQICLHSCFQ
GENACD   321  LVSSTGAKVIIHRQDEYPFVEDVGTEIETAMVTSIGMHLTESFKLSEPYSQCTEDGSDVPIRNIYNAAYSLQICLHSCFQ
GENACE   321  LVSSTGAKVIIHRQDEYPFVEDVGTEIETAMVTSIGMHLTESFKLSEPYSQCTEDGSDVPIRNIYNAAYSLQICLHSCFQ
GENACG   321  LVSSTGAKVIIHRQDEYPFVEDVGTEIETAMVTSIGMHLTESFKLSEPYSQCTEDGSDVPIRNIYNAAYSLQICLHSCFQ
GENACH   321  LVSSTGAKVIIHRQDEYPFVEDVGTEIETAMVTSIGMHLTESFKLSEPYSQCTEDGSDVPIRNIYNAAYSLQICLHSCFQ
GENACJ   321  LVSSTGAKVIIHRQDEYPFVEDVGTEIETAMVTSIGMHLTESFKLSEPYSQCTEDGSDVPIRNIYNAAYSLQICLHSCFQ
GENACT   321  LVSSTGAKVIIHRQDEYPFVEDVGTEIETAMVTSIGMHLTESFKLSEPYSQCTEDGSDVPIRNIYNAAYSLQICLHSCFQ
GENACV   321  LVSSTGAKVIIHRQDEYPFVEDVGTEIETAMVTSIGMHLTESFKLSEPYSQCTEDGSDVPIRNIYNAAYSLQICLHSCFQ
GENACW   321  LVSSTGAKVIIHRQDEYPFVEDVGTEIETAMVTSIGMHLTESFKLSEPYSQCTEDGSDVPIRNIYNAAYSLQICLHSCFQ

GENACGB  401  TKMVEKCGCAQYSQPLPPAANYCNYQQHPNWMYCYYQLHRAFVQEELGCQSVCKEACRFKEWTLTTSLAQWPSVVSEKWL
GENACA   401  TKMVEKCGCAQYSQPLPPAANYCNYQQHPNWMYCYYQLHRAFVQEELGCQSVCKEACSFKEWTLTTSLAQWPSVVSEKWL
GENACB   401  TKMVEKCGCAQYSQPLPPAANYCNYQQHPNWMYCYYQLHRAFVQEELGCQSVCKEACSFKEWTLTTSLAQWPSVVSEKWL
GENACD   401  TKMVEKCGCAQYSQPLPPAANYCNYQQHPNWMYCYYQLHRAFVQEELGCQSVCKEACSFKEWTLTTSLAQWPSVVSEKWL
GENACE   401  TKMVEKCGCAQYSQPLPPAANYCNYQQHPNWMYCYYQLHRAFVQEELGCQSVCKEACSFKEWTLTTSLAQWPSVVSEKWL
GENACG   401  TKMVEKCGCAQYSQPLPPAANYCNYQQHPNWMYCYYQLHRAFVQEELGCQSVCKEACSFKEWTLTTSLAQWPSVVSEKWL
GENACH   401  TKMVEKCGCAQYSQPLPPAANYCNYQQHPNWMYCYYQLHRAFVQEELGCQSVCKEACSFKEWTLTTSLAQWPSVVSEKWL
GENACJ   401  TKMVEKCGCAQYSQPLPPAANYCNYQQHPNWMYCYYQLHRAFVQEELGCQSVCKEACSLKEWTLTTSLAQWPSVVSEKWL
GENACT   401  TKMVEKCGCAQYSQPLPPAANYCNYQQHPNWMYCYYQLHRAFVQEELGCQSVCKEACSFKEWTLTTSLAQWPSVVSEKWL
GENACV   401  TKMVEKCGCAQYSQPLPPAANYCNYQQHPNWMYCYYQLHRAFVQEELGCQSVCKEACSFKEWTLTTSLAQWPSVVSEKWL
GENACW   401  TKMVEKCGCAQYSQPLPPAANYCNYQQHPNWMYCYYQLHRAFVQEELGCQSVCKEACSFKEWTLTTSLAQWPSVVSEKWL
```

Figure 8C

```
GENACGB  481  LPVLTWDQGRQVNKKLNKTDLAKLLIFYKDLNQRSIMESPANSIEMLLSNFGGQLGLWMSCSVVCVIEIIEVFFIDFFSI
GENACA   481  LPVLTWDQGRQVNKKLNKTDLAKLLIFYKDLNQRSIMESPANSIEMLLSNFGGQLGLWMSCSVVCVIEIIEVFFIDFFSI
GENACB   481  LPVLTWDQGRQVNKKLNKTDLAKLLIFYKDLNQRSIMESPANSIEMLLSNFGGQLGLWMSCSVVCVIEIIEVFFIDFFSI
GENACD   481  LPVLTWDQGRQVNKKLNKTDLAKLLIFYKDLNQRSIMESPANSIEMLLSNFGGQLGLWMSCSVVCVIEIIEVFFIDFFSI
GENACE   481  LPVLTWDQGRQVNKKLNKTDLAKLLIFYKDLNQRSIMESPANSIEMLLSNFGGQLGLWMSCSVVCVIEIIEVFFIDFFSI
GENACG   481  LPVLTWDQGRQVNKKLNKTDLAKLLIFYKDLNQRSIMESPANSIEMLLSNFGGQLGLWMSCSVVCVIEIIEVFFIDFFSI
GENACH   481  LPVLTWDQGRQVNKKLNKTDLAKLLIFYKDLNQRSIMESPANSIEMLLSNFGGQLGLWMSCSVVCVIEIIEVFFIDFFSI
GENACJ   481  LPVLTWDQGRQVNKKLNKTDLAKLLIFYKDLNQRSIMESPANSIEMLLSNFGGQLGLWMSCSVVCVMEIIEVFFIDFFSI
GENACT   481  LPVLTWDQGRQVNKKLNKTDLAKLLIFYKDLNQRSIMESPANSIEMLLSNFGGQLGLWMSCSVVCVIEIIEVFFIDFFSI
GENACV   481  LPVLTWDQGRQVNKKLNKTDLAKLLIFYKDLNQRSIMESPANSIEMLLSNFGGQLGLWMSCSVVCVIEIIEVFFIDFFSI
GENACW   481  LPVLTWDQGRQVNKKLNKTDLAKLLIFYKDLNQRSIMESPANSIEMLLSNFGGQLGLWMSCSVVCVIEIIEVFFIDFFSI

GENACGB  561  IARRQWQKAKEWWAWKQAPPCPEAPRSPQGQDNPALDIDDDLPTFNSALHLPPALGTQVPGTPPPKYNTLRLERAFSNQL
GENACA   561  IARRQWQKAKEWWAWKQAPPCPEAPRSPQGQDNPALDIDDDLPTFNSALHLPPALGTQVPGTPPPKYNTLRLERAFSNQL
GENACB   561  IARRQWQKAKEWWAWKQAPPCPEAPRSPQGQDNPALDIDDDLPTFNSALHLPPALGTQVPGTPPPKYNTLRLERAFSNQL
GENACD   561  IARRQWQKAKEWWAWKQAPPCPEAPRSPQGQDNPALDIDDDLPTFNSALHLPPALGTQVPGTPPPKYNTLRLERAFSNQL
GENACE   561  IARRQWQKAKEWWAWKQAPPCPEAPRSPQGQDNPALDIDDDLPTFNSALHLPPALGTQVPSTPPPKYNTLRLERAFSNQL
GENACG   561  TARRQWQKAKEWWAWKQAPPCPEAPRSPQGQDNPALDIDDDLPTFNSALHLPPALGTQVPGTPPPKYNTLRLERAFSNSL
GENACH   561  IARRQWQKAKEWWAWKQAPPCPEAPRSPQGQDNPALDIDGLPTFNSALHLPPALGTQVPGTPPPKYNTLRLERAFSNQL
GENACJ   561  TARRQWQKAKEWWAWKQAPPCPEAPRSPQGQDNPALDIDDDLPTFNSALHLPPALGTQVPGTPPPKYNTLRLERAFSNQL
GENACT   561  IARRQWQKAKEWWAWKQAPPCPEAPRSPQGQDNPALDIDDDLPTFNSALHLPPALGTQVPGTPPPKYNTLRLERAFSNQL
GENACV   561  IARRQWQKAKEWWAWKQAPPCPEAPRSPQGQDNPALDIDDDLPTFNSALHLPPALGTQVPGTPPPKYNTLRLERAFSNQL
GENACW   561  IARRQWQKAKEWWAWKQAPPCPEAPRSPQGQDNPALDIDDDLPTFNSALHLPPALGTQVPGTPPPKYNTLRLERAFSNQL

GENACGB  641  TDTQMLDEL
GENACA   641  TDTQMLDEL
GENACB   641  TDTQMLDEL
GENACD   641  TDTQMLDEL
GENACE   641  TDTQMLDEL
GENACG   641  TDTQMLDEL
GENACH   641  TDTQMLDEL
GENACJ   641  TDTQMLDEL
GENACT   641  TDTQMLDEL
GENACV   641  TDTQMLDEL
GENACW   641  TDTQMLDEL
```

Figure 8D

SEQUENCE LISTING

<160> NUMBER OF SEQ ID NOS: 36

<210> SEQ ID NO 1
<211> LENGTH: 2010
<212> TYPE: DNA
<213> ORGANISM: Homo sapiens

<400> SEQUENCE: 1

| | | | | | |
|---|---|---|---|---|---|
| atggagggga | acaagctgga | ggagcaggac | tctagccctc | cacagtccac tccagggctc | 60 |
| atgaagggga | acaagcgtga | ggagcagggg | ctgggcccg | aacctgcggc gccccagcag | 120 |
| cccacggcgg | aggaggaggc | cctgatcgag | ttccaccgct | cctaccgaga gctcttcgag | 180 |
| ttcttctgca | acaacaccac | catccacggc | gccatccgcc | tggtgtgctc ccagcacaac | 240 |
| cgcatgaaga | cggccttctg | gcagtgctg | tggctctgca | cctttggcat gatgtactgg | 300 |
| caattcggcc | tgcttttcgg | agagtacttc | agctaccccg | tcagcctcaa catcaacctc | 360 |
| aactcggaca | agctcgtctt | ccccgcagtg | accatctgca | ccctcaatcc ctacaggtac | 420 |
| ccggaaatta | agaggagct | ggaggagctg | accgcatca | cagagcagac gctctttgac | 480 |
| ctgtacaaat | acagctcctt | caccactctc | gtggccggct | cccgcagccg tcgcgacctg | 540 |
| cgggggactg | tgccgcaccc | cttgcagcgc | ctgagggtcc | cgcccccgcc tcacggggcc | 600 |
| cgtcgagccc | gtagcgtggc | ctccagcttg | cggacaaca | accccaggt ggactggaag | 660 |
| gactggaaga | tcggcttcca | gctgtgcaac | cagaacaaat | cggactgctt ctaccagaca | 720 |
| tactcatcag | gggtggatgc | ggtgagggag | tggtaccgct | tccactacat caacatcctg | 780 |
| tcgaggctgc | cagagactct | gccatccctg | gaggaggaca | cgctgggcaa cttcatcttc | 840 |
| gcctgccgct | tcaaccaggt | ctcctgcaac | caggcgaatt | actctcactt ccaccacccg | 900 |
| atgtatggaa | actgctatac | tttcaatgac | aagaacaact | ccaacctctg gatgtcttcc | 960 |
| atgcctggaa | tcaacaacgg | tctgtccctg | atgctgcgcg | cagagcagaa tgacttcatt | 1020 |
| cccctgctgt | ccacagtgac | tggggcccgg | gtaatggtgc | acgggcagga tgaacctgcc | 1080 |
| tttatggatg | atggtggctt | taacttgcgg | cctggcgtgg | agacctccat cagcatgagg | 1140 |
| aaggaaaccc | tggacagact | tgggggcgat | tatggcgact | gcaccaagaa tggcagtgat | 1200 |
| gttcctgttg | agaaccttta | ccctcaaag | tacacacagc | aggtgtgtat tcactcctgc | 1260 |
| ttccaggaga | gcatgatcaa | ggagtgtggc | tgtgcctaca | tcttctatcc gcggccccag | 1320 |
| aacgtggagt | actgtgacta | cagaaagcac | agttcctggg | gtactgcta ctataagctc | 1380 |
| caggttgact | tctcctcaga | ccacctgggc | tgtttcacca | agtgccggaa gccatgcagc | 1440 |
| gtgaccagct | accagctctc | tgctggttac | tcacgatggc | cctcggtgac atcccaggaa | 1500 |
| tgggtcttcc | agatgctatc | gcgacagaac | aattacaccg | tcaacaacaa gagaaatgga | 1560 |
| gtggccaaag | tcaacatctt | cttcaaggag | ctgaactaca | aaaccaattc tgagtctccc | 1620 |
| tctgtcacga | tggtcaccct | cctgtccaac | ctgggcagcc | agtggagcct gtggttcggc | 1680 |
| tcctcggtgt | tgtctgtggt | ggagatggct | gagctcgtct | ttgacctgct ggtcatcatg | 1740 |
| ttcctcatgc | tgctccgaag | gttccgaagc | cgatactggt | ctccaggccg agggggcagg | 1800 |
| ggtgctcagg | aggtagcctc | cacccctgca | tcctcccctc | cttcccactt ctgccccac | 1860 |
| cccatgtctc | tgtccttgtc | ccagccaggc | cctgctccct | ctccagcctt gacagcccct | 1920 |
| cccccctgcct | atgccaccct | gggccccgc | ccatctccag | ggggctctgc aggggccagt | 1980 |
| tcctccacct | gtcctctggg | ggggcccctga | | | 2010 |

<210> SEQ ID NO 2
<211> LENGTH: 668
<212> TYPE: PRT
<213> ORGANISM: Homo Sapiens

<400> SEQUENCE: 2

| | | | | | | | | | | | | | | | |
|---|---|---|---|---|---|---|---|---|---|---|---|---|---|---|---|
| Glu | Gly | Asn | Lys | Leu | Glu | Glu | Gln | Asp | Ser | Pro | Pro | Gln | Ser | Thr | |
| 1 | | | | 5 | | | | | 10 | | | | | 15 | |
| Pro | Gly | Leu | Met | Lys | Gly | Asn | Lys | Arg | Glu | Glu | Gln | Gly | Leu | Gly | Pro |
| | | | 20 | | | | | 25 | | | | | 30 | | |
| Glu | Pro | Ala | Ala | Pro | Gln | Gln | Pro | Thr | Ala | Glu | Glu | Ala | Leu | Ile | |
| | | 35 | | | | | 40 | | | | | 45 | | | |
| Glu | Phe | His | Arg | Ser | Tyr | Arg | Glu | Leu | Phe | Glu | Phe | Phe | Cys | Asn | Asn |
| | 50 | | | | | 55 | | | | | 60 | | | | |
| Thr | Thr | Ile | His | Gly | Ala | Ile | Arg | Leu | Val | Cys | Ser | Gln | His | Asn | Arg |
| 65 | | | | | 70 | | | | | 75 | | | | | 80 |
| Met | Lys | Thr | Ala | Phe | Trp | Ala | Val | Leu | Trp | Leu | Cys | Thr | Phe | Gly | Met |
| | | | | 85 | | | | | 90 | | | | | 95 | |
| Met | Tyr | Trp | Gln | Phe | Gly | Leu | Leu | Phe | Gly | Tyr | Phe | Ser | Tyr | Pro | |
| | | | 100 | | | | | 105 | | | | | 110 | | |
| Val | Ser | Leu | Asn | Ile | Asn | Leu | Asn | Ser | Asp | Lys | Leu | Val | Phe | Pro | Ala |
| | | 115 | | | | | 120 | | | | | 125 | | | |
| Val | Thr | Ile | Cys | Thr | Leu | Asn | Pro | Tyr | Arg | Tyr | Pro | Glu | Ile | Lys | Glu |
| | 130 | | | | | 135 | | | | | 140 | | | | |
| Glu | Leu | Glu | Glu | Leu | Asp | Arg | Ile | Thr | Glu | Gln | Thr | Leu | Phe | Asp | Leu |
| 145 | | | | | 150 | | | | | 155 | | | | | 160 |
| Tyr | Lys | Tyr | Ser | Ser | Phe | Thr | Thr | Leu | Val | Ala | Gly | Ser | Arg | Ser | Arg |
| | | | | 165 | | | | | 170 | | | | | 175 | |
| Arg | Asp | Leu | Arg | Gly | Thr | Leu | Pro | His | Pro | Leu | Gln | Arg | Leu | Arg | Val |
| | | | 180 | | | | | 185 | | | | | 190 | | |
| Pro | Pro | Pro | Pro | His | Gly | Ala | Arg | Arg | Ala | Arg | Ser | Val | Ala | Ser | Ser |
| | | | | 195 | | | | | 200 | | | | | 205 | |
| Leu | Arg | Asp | Asn | Asn | Pro | Gln | Val | Asp | Trp | Lys | Asp | Trp | Lys | Ile | Gly |
| | 210 | | | | | 215 | | | | | 220 | | | | |
| Phe | Gln | Leu | Cys | Asn | Gln | Asn | Lys | Ser | Asp | Cys | Phe | Tyr | Gln | Thr | Tyr |
| 225 | | | | | 230 | | | | | 235 | | | | | 240 |
| Ser | Ser | Gly | Val | Asp | Ala | Val | Arg | Glu | Trp | Tyr | Arg | Phe | His | Tyr | Ile |
| | | | | 245 | | | | | 250 | | | | | 255 | |
| Asn | Ile | Leu | Ser | Arg | Leu | Pro | Glu | Thr | Leu | Pro | Ser | Leu | Glu | Glu | Asp |
| | | | 260 | | | | | 265 | | | | | 270 | | |
| Thr | Leu | Gly | Asn | Phe | Ile | Phe | Ala | Cys | Arg | Phe | Asn | Gln | Val | Ser | Cys |
| | | 275 | | | | | 280 | | | | | 285 | | | |
| Asn | Gln | Ala | Asn | Tyr | Ser | His | Phe | His | His | Pro | Met | Tyr | Gly | Asn | Cys |
| | 290 | | | | | 295 | | | | | 300 | | | | |
| Tyr | Thr | Phe | Asn | Asp | Lys | Asn | Asn | Ser | Asn | Leu | Trp | Met | Ser | Ser | Met |
| 305 | | | | | 310 | | | | | 315 | | | | | 320 |
| Pro | Gly | Ile | Asn | Asn | Gly | Leu | Ser | Leu | Met | Leu | Arg | Ala | Glu | Gln | Asn |
| | | | | 325 | | | | | 330 | | | | | 335 | |
| Asp | Phe | Ile | Pro | Leu | Leu | Ser | Thr | Val | Thr | Gly | Ala | Arg | Val | Met | Val |
| | | | 340 | | | | | 345 | | | | | 350 | | |
| His | Gly | Gln | Asp | Glu | Pro | Ala | Phe | Met | Asp | Asp | Gly | Gly | Phe | Asn | Leu |
| | | 355 | | | | | 360 | | | | | 365 | | | |
| Arg | Pro | Gly | Val | Glu | Thr | Ser | Ile | Ser | Met | Arg | Lys | Glu | Thr | Leu | Asp |

```
         370                 375                 380
Arg Leu Gly Gly Asp Tyr Gly Asp Cys Thr Lys Asn Gly Ser Asp Val
385                 390                 395                 400

Pro Val Glu Asn Leu Tyr Pro Ser Lys Tyr Thr Gln Gln Val Cys Ile
                405                 410                 415

His Ser Cys Phe Gln Glu Ser Met Ile Lys Glu Cys Gly Cys Ala Tyr
            420                 425                 430

Ile Phe Tyr Pro Arg Pro Gln Asn Val Glu Tyr Cys Asp Tyr Arg Lys
        435                 440                 445

His Ser Ser Trp Gly Tyr Cys Tyr Tyr Lys Leu Gln Val Asp Phe Ser
    450                 455                 460

Ser Asp His Leu Gly Cys Phe Thr Lys Cys Arg Lys Pro Cys Ser Val
465                 470                 475                 480

Thr Ser Tyr Gln Leu Ser Ala Gly Tyr Ser Arg Trp Pro Ser Val Thr
                485                 490                 495

Ser Gln Glu Trp Val Phe Gln Met Leu Ser Arg Gln Asn Asn Tyr Thr
            500                 505                 510

Val Asn Asn Lys Arg Asn Gly Val Ala Lys Val Asn Ile Phe Phe Lys
        515                 520                 525

Glu Leu Asn Tyr Lys Thr Asn Ser Glu Ser Pro Ser Val Thr Met Val
    530                 535                 540

Thr Leu Leu Ser Asn Leu Gly Ser Gln Trp Ser Leu Trp Phe Gly Ser
545                 550                 555                 560

Ser Val Leu Ser Val Val Glu Met Ala Glu Leu Val Phe Asp Leu Leu
                565                 570                 575

Val Ile Met Phe Leu Met Leu Leu Arg Arg Phe Arg Ser Arg Trp Pro
            580                 585                 590

Ser Pro Gly Arg Gly Gly Arg Gly Ala Gln Glu Val Ala Ser Thr Leu
        595                 600                 605

Ala Ser Ser Pro Pro Ser His Phe Cys Pro His Pro Met Ser Leu Ser
    610                 615                 620

Leu Ser Gln Pro Gly Pro Ala Pro Ser Pro Ala Leu Thr Ala Pro Pro
625                 630                 635                 640

Pro Ala Tyr Ala Thr Leu Gly Pro Arg Pro Ser Pro Gly Gly Ser Ala
                645                 650                 655

Gly Ala Ser Ser Ser Thr Cys Pro Leu Gly Gly Pro
            660                 665

<210> SEQ ID NO 3
<211> LENGTH: 1923
<212> TYPE: DNA
<213> ORGANISM: Homo Sapiens

<400> SEQUENCE: 3
atgcacgtga agaagtacct gctgaagggc ctgcatcggc tgcagaaggg ccccggctac      60
acgtacaagg agctgctggt gtggtactgc gacaacacca acacccacgg ccccaagcgc     120
atcatctgtg aggggcccaa gaagaaagcc atgtggttcc tgctcaccct gctcttcgcc     180
gccctcgtct gctggcagtg gggcatcttc atcaggacct acttgagctg gaggtcagc      240 gtctccctct ccgtaggctt caagaccatg gacttccccg ccgtcaccat ctgcaatgct     300
agccccttca gtattccaa atcaagcat ttgctgaagg acctggatga gctgatggaa       360
gctgtcctgg agagaatcct ggctcctgag ctaagccatg ccaatgccac caggaacctg     420
aacttctcca tctggaacca cacccctg gtccttattg atgaacggaa ccccaccac       480
```

-continued

```
cccatggtcc ttgatctctt tggagacaac cacaatggct taacaagcag ctcagcatca    540
gaaaagatct gtaatgccca cgggtgcaaa atggccatga gactatgtag cctcaacagg    600
acccagtgta ccttccggaa cttcaccagt gctacccagg cattgacaga gtggtacatc    660
ctgcaggcca ccaacatctt tgcacaggtg ccacagcagg agctagtaga gatgagctac    720
cccggcgagc agatgatcct ggcctgccta ttcggagctg agccctgcaa ctaccggaac    780
ttcacgtcca tcttctaccc tcactatggc aactgttaca tcttcaactg ggcatgaca    840 gagaaggcac ttccttcggc caaccctgga actgaattcg gcctgaagtt gatcctggac    900
ataggccagg aagactacgt ccccttcctt gcgtccacgg ccggggtcag gctgatgctt    960
cacgagcaga ggtcataccc cttcatcaga gatgagggca tctacgccat gtcgggggaca   1020 gagacgtcca tcggggtact cgtggacaag cttcagcgca tgggggagcc ctacagcccg   1080
tgcaccgtga atggttctga ggtccccgtc caaaacttct acagtgacta caacacgacc   1140
tactccatcc aggcctgtct tcgctcctgc ttccaagacc acatgatccg taactgcaac   1200
tgtggccact acctgtaccc actgcccgcgt ggggagaaat actgcaacaa ccggggacttc   1260 ccagactggg cccattgcta ctcagatcta cagatgagcg tggcgcagag agagacctgc   1320
attggcatgt gcaaggagtc ctgcaatgac acccagtaca agatgaccat ctccatggct   1380
gactggcctt ctgaggcctc cgaggactgg attttccacg tcttgtctca ggagcgggac   1440
caaagcacca atatcaccct gagcaggaag ggaattgtca agctcaacat ctacttccaa   1500
gaatttaact atcgcaccat tgaagaatca gcagccaata acatcgtctg ctgctctcg    1560 aatctgggtg ccagtttggg cttctggatg gggggctctg tgctgtgcct catcgagttt   1620
ggggagatca tcatcgactt tgtgtggatc accatcatca agctggtgg cttggccaag    1680 agcctacggc agcggcgagc ccaagccagc tacgctggcc accgccacac cgtggccgag   1740
ctggtggagg cccacaccaa ctttggcttc agcctgaca cggcccccg cagccccaac    1800 actgggccct accccagtga gcaggccctg cccatcccag caccccgcc ccccaactat    1860 gactccctgc gtctgcagcc gctggacgtc atcgagtctg acagtgaggg tgatgccatc   1920
taa                                                                 1923
```

```
<210> SEQ ID NO 4
<211> LENGTH: 640
<212> TYPE: PRT
<213> ORGANISM: Homo Sapiens

<400> SEQUENCE: 4
```

Met His Val Lys Lys Tyr Leu Leu Lys Gly Leu His Arg Leu Gln Lys
1               5                   10                  15

Gly Pro Gly Tyr Thr Tyr Lys Glu Leu Leu Val Trp Tyr Cys Asp Asn
            20                  25                  30

Thr Asn Thr His Gly Pro Lys Arg Ile Ile Cys Glu Gly Pro Lys Lys
        35                  40                  45

Lys Ala Met Trp Phe Leu Leu Thr Leu Leu Phe Ala Ala Leu Val Cys
    50                  55                  60

Trp Gln Trp Gly Ile Phe Ile Arg Thr Tyr Leu Ser Trp Glu Val Ser
65                  70                  75                  80

Val Ser Leu Ser Val Gly Phe Lys Thr Met Asp Phe Pro Ala Val Thr
                85                  90                  95

Ile Cys Asn Ala Ser Pro Phe Lys Tyr Ser Lys Ile Lys His Leu Leu
            100                 105                 110

```
Lys Asp Leu Asp Glu Leu Met Glu Ala Val Leu Glu Arg Ile Leu Ala
            115                 120                 125

Pro Glu Leu Ser His Ala Asn Ala Thr Arg Asn Leu Asn Phe Ser Ile
        130                 135                 140

Trp Asn His Thr Pro Leu Val Leu Ile Asp Glu Arg Asn Pro His His
145                 150                 155                 160

Pro Met Val Leu Asp Leu Phe Gly Asp Asn His Asn Gly Leu Thr Ser
                165                 170                 175

Ser Ser Ala Ser Glu Lys Ile Cys Asn Ala His Gly Cys Lys Met Ala
            180                 185                 190

Met Arg Leu Cys Ser Leu Asn Arg Thr Gln Cys Thr Phe Arg Asn Phe
        195                 200                 205

Thr Ser Ala Thr Gln Ala Leu Thr Glu Trp Tyr Ile Leu Gln Ala Thr
            210                 215                 220

Asn Ile Phe Ala Gln Val Pro Gln Gln Glu Leu Val Glu Met Ser Tyr
225                 230                 235                 240

Pro Gly Glu Gln Met Ile Leu Ala Cys Leu Phe Gly Ala Glu Pro Cys
                245                 250                 255

Asn Tyr Arg Asn Phe Thr Ser Ile Phe Tyr Pro His Tyr Gly Asn Cys
            260                 265                 270

Tyr Ile Phe Asn Trp Gly Met Thr Glu Lys Ala Leu Pro Ser Ala Asn
        275                 280                 285

Pro Gly Thr Glu Phe Gly Leu Lys Leu Ile Leu Asp Ile Gly Gln Glu
    290                 295                 300

Asp Tyr Val Pro Phe Leu Ala Ser Thr Ala Gly Val Arg Leu Met Leu
305                 310                 315                 320

His Glu Gln Arg Ser Tyr Pro Phe Ile Arg Asp Glu Gly Ile Tyr Ala
                325                 330                 335

Met Ser Gly Thr Glu Thr Ser Ile Gly Val Leu Val Asp Lys Leu Gln
            340                 345                 350

Arg Met Gly Glu Pro Tyr Ser Pro Cys Thr Val Asn Gly Ser Glu Val
        355                 360                 365

Pro Val Gln Asn Phe Tyr Ser Asp Tyr Asn Thr Thr Tyr Ser Ile Gln
    370                 375                 380

Ala Cys Leu Arg Ser Cys Phe Gln Asp His Met Ile Arg Asn Cys Asn
385                 390                 395                 400

Cys Gly His Tyr Leu Tyr Pro Leu Pro Arg Gly Glu Lys Tyr Cys Asn
                405                 410                 415

Asn Arg Asp Phe Pro Asp Trp Ala His Cys Tyr Ser Asp Leu Gln Met
            420                 425                 430

Ser Val Ala Gln Arg Glu Thr Cys Ile Gly Met Cys Lys Glu Ser Cys
        435                 440                 445

Asn Asp Thr Gln Tyr Lys Met Thr Ile Ser Met Ala Asp Trp Pro Ser
    450                 455                 460

Glu Ala Ser Glu Asp Trp Ile Phe His Val Leu Ser Gln Glu Arg Asp
465                 470                 475                 480

Gln Ser Thr Asn Ile Thr Leu Ser Arg Lys Gly Ile Val Lys Leu Asn
                485                 490                 495

Ile Tyr Phe Gln Glu Phe Asn Tyr Arg Thr Ile Glu Glu Ser Ala Ala
            500                 505                 510

Asn Asn Ile Val Trp Leu Leu Ser Asn Leu Gly Gly Gln Phe Gly Phe
        515                 520                 525
```

```
Trp Met Gly Gly Ser Val Leu Cys Leu Ile Glu Phe Gly Glu Ile Ile
        530                 535                 540

Ile Asp Phe Val Trp Ile Thr Ile Ile Lys Leu Val Ala Leu Ala Lys
545                 550                 555                 560

Ser Leu Arg Gln Arg Arg Ala Gln Ala Ser Tyr Ala Gly Pro Pro Pro
                565                 570                 575

Thr Val Ala Glu Leu Val Glu Ala His Thr Asn Phe Gly Phe Gln Pro
            580                 585                 590

Asp Thr Ala Pro Arg Ser Pro Asn Thr Gly Pro Tyr Pro Ser Glu Gln
        595                 600                 605

Ala Leu Pro Ile Pro Gly Thr Pro Pro Asn Tyr Asp Ser Leu Arg
    610                 615                 620

Leu Gln Pro Leu Asp Val Ile Glu Ser Asp Ser Glu Gly Asp Ala Ile
625                 630                 635                 640

<210> SEQ ID NO 5
<211> LENGTH: 1950
<212> TYPE: DNA
<213> ORGANISM: Homo Sapiens

<400> SEQUENCE: 5
```

| | | | | | |
|---|---|---|---|---|---|
| atggcacccg | agagaagat | caaagccaaa | atcaagaaga | atctgcccgt | gacgggccct | 60 |
| caggcgccga | ccattaaaga | gctgatgcgg | tggtactgcc | tcaacaccaa | cacccatggc | 120 |
| tgtcgccgca | tcgtggtgtc | ccgcggccgt | ctgcgccgcc | tcctctggat | cgggttcaca | 180 |
| ctgactgccg | tggccctcat | cctctggcag | tgcgccctcc | tcgtcttctc | cttctatact | 240 |
| gtctcagttt | ccatcaaagt | ccacttccgg | aagctggatt | ttcctgcagt | caccatctgc | 300 |
| aacatcaacc | cctacaagta | cagcaccgtt | cgccaccttc | tagctgactt | ggaacaggag | 360 |
| accagagagg | ccctgaagtc | cctgtatggc | tttccagagt | cccggaagcg | ccgagaggcg | 420 |
| gagtcctgga | actccgtctc | agagggaaag | cagcctagat | tctcccaccg | gattccgctg | 480 |
| ctgatctttg | atcaggatga | aagggcaag | gccagggact | tcttcacagg | gaggaagcgg | 540 |
| aaagtcggcg | gtagcatcat | tcacaaggct | tcaaatgtca | tgcacatcga | gtccaagcaa | 600 |
| gtggtgggat | tccaactgtg | ctcaaatgac | acctccgact | gtgccaccta | caccttcagc | 660 |
| tcgggaatca | atgccattca | ggagtggtat | aagctacact | acatgaacat | catggcacag | 720 |
| gtgcctctgg | agaagaaaat | caacatgagc | tattctgctg | aggagctgct | ggtgacctgc | 780 |
| ttctttgatg | gagtgtcctg | tgatgccagg | aatttcacgc | ttttccacca | cccgatgcat | 840 |
| gggaattgct | atactttcaa | caacagagaa | atgagaccaa | ttctcagcac | tccatggggg | 900 |
| ggcagcgaat | atgggctgca | agtcattttg | tacataaacg | aagaggaata | caaccccattc | 960 |
| ctcgtgtcct | ccactggagc | taaggtgatc | atccatcggc | aggatgagta | tcccttcgtc | 1020 |
| gaagatgtgg | aacagagat | tgagacagca | atggtcacct | ctataggaat | gcacctgaca | 1080 |
| gagtccttca | agctgagtga | gccctacagt | cagtgcacgg | aggacgggag | tgacgtgcca | 1140 |
| atcaggaaca | tctacaacgc | tgcctactcg | ctccagatct | gccttcattc | atgcttccag | 1200 |
| acaaagatgg | tggagaaatg | tgggtgtgcc | cagtacagcc | agcctctacc | tcctgcagcc | 1260 |
| aactactgca | actaccagca | gcaccccaac | tggatgtatt | gttactacca | actgcatcga | 1320 |
| gcctttgtcc | aggaagagct | gggctgccag | tctgtgtgca | aggaagcctg | cagctttaaa | 1380 |
| gagtggacac | taaccacaag | cctggcacaa | tggccatctg | tggtttcgga | gaagtggttg | 1440 |
| ctgcctgttc | tcacttggga | ccaaggccgg | caagtaaaca | aaaagctcaa | caagacagac | 1500 |

```
ttggccaaac tcttgatatt ctacaaagac ctgaaccaga gatccatcat ggagagccca    1560
gccaacagta ttgagatgct tctgtccaac ttcggtggcc agctgggcct gtggatgagc    1620
tgctctgttg tctgcgtcat cgagatcatc gaggtcttct tcattgactt cttctctatc    1680
attgcccgcc gccagtggca gaaagccaag gagtggtggg cctggaaaca ggctccccca    1740
tgtccagaag ctccccgtag cccacagggc caggacaatc cagccctgga tatagacgat    1800
gacctaccca ctttcaactc tgctttgcac ctgcctccag ccctaggaac ccaagtgccc    1860
ggcacaccgc cccccaaata caataccttg cgcttggaga gggccttttc caaccagctc    1920
acagataccc agatgctaga tgagctctga                                      1950
```

<210> SEQ ID NO 6
<211> LENGTH: 649
<212> TYPE: PRT
<213> ORGANISM: Homo Sapiens

<400> SEQUENCE: 6

```
Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
        275                 280                 285

Arg Glu Asn Glu Thr Ile Leu Ser Thr Ser Met Gly Gly Ser Glu Tyr
```

-continued

```
               290                 295                 300
Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645
```

<210> SEQ ID NO 7
<211> LENGTH: 1917
<212> TYPE: DNA
<213> ORGANISM: Homo Sapiens

<400> SEQUENCE: 7

```
atggctgagc accgaagcat ggacgggaga atggaagcag ccacacgggg gggctctcac      60
ctccaggctg cagcccagac gccccccagg ccggggccac catcagcacc accaccacca     120
```

-continued

```
cccaaggagg ggcaccagga ggggctggtg gagctgcccg cctcgttccg ggagctgctc      180
accttcttct gcaccaatgc caccatccac ggcgccatcc gcctggtctg ctcccgcggg      240
aaccgcctca agacgacgtc ctgggggctg ctgtccctgg gagccctggt cgcgctctgc      300
tggcagctgg ggctcctctt tgagcgtcac tggcaccgcc cggtcctcat ggccgtctct      360
gtgcactcgg agcgcaagct gctcccgctg gtcaccctgt gtgacgggaa cccacgtcgg      420
ccgagtccgg tcctccgcca tctggagctg ctggacgagt ttgccaggga gaacattgac      480
tccctgtaca acgtcaacct cagcaaaggc agagccgccc tctccgccac tgtccccgc       540 cacgagcccc ccttccacct ggaccgggag atccgtctgc agaggctgag ccactcgggc      600
agccgggtca gagtggggtt cagactgtgc aacagcacgg gcggcgactg cttttaccga      660
ggctacacgt caggcgtggc ggctgtccag gactggtacc acttccacta tgtggatatc      720
ctggccctgc tgcccgcggc atgggaggac agccacggga gccaggacgg ccacttcgtc      780
ctctcctgca gttacgatgg cctggactgc caggcccgac agttccggac cttccaccac      840
cccacctacg gcagctgcta cacggtcgat ggcgtctgga cagctcagcg ccccggcatc      900
acccacggag tcggcctggt cctcagggtt gagcagcagc ctcacctccc tctgctgtcc      960
acgctggccg gcatcagggt catggttcac ggccgtaacc acacgccctt cctggggcac     1020
cacagcttca gcgtccggcc aggaacggag gccaccatca gcatccgaga ggacgaggtg     1080
caccggctcg ggagcccta cggccactgc accgccggcg gggaaggcgt ggaggtggag     1140
ctgctacaca acacctccta caccaggcag gcctgcctgg tgtcctgctt ccagcagctg     1200
atggtggaga cctgctcctg tggctactac ctccaccctc tgccggcggg ggctgagtac     1260
tgcagctctg cccggcaccc tgcctgggga cactgcttct accgcctcta ccaggacctg     1320
gagacccacc ggctcccctg tacctcccgc tgccccaggc cctgcaggga gtctgcattc     1380
aagctctcca ctgggacctc caggtggcct tccgccaagt cagctggatg gactctggcc     1440
acgctaggtg aacagggggct gccgcatcag agccacagac agaggagcag cctggccaaa     1500
atcaacatcg tctaccagga gctcaactac cgctcagtgg aggaggcgcc cgtgtactcg     1560
gtgccgcagc tgctctccgc catgggcagc ctctacagcc tgtggtttgg ggcctccgtc     1620
ctctccctcc tggagctcct ggagctgctg ctcgatgctt ctgccctcac cctggtgcta     1680
ggcggccgcc ggctccgcag ggcgtggttc tcctggccca gagccagccc tgcctcaggg     1740
gcgtccagca tcaagccaga ggccagtcag atgcccccgc ctgcaggcgg cacgtcagat     1800
gacccggagc ccagcgggcc tcatctccca cgggtgatgc ttccagggga tctggcggga     1860
gtctcagccg aagagagctg ggctgggccc cagccccttg agactctgga cacctga         1917
```

<210> SEQ ID NO 8
<211> LENGTH: 638
<212> TYPE: PRT
<213> ORGANISM: Homo Sapiens

<400> SEQUENCE: 8

Met Ala Glu His Arg Ser Met Asp Gly Arg Met Glu Ala Ala Thr Arg
1               5                   10                  15

Gly Gly Ser His Leu Gln Ala Ala Ala Gln Thr Pro Arg Pro Gly
            20                  25                  30

Pro Pro Ser Ala Pro Pro Pro Lys Glu Gly His Gln Glu Gly
        35                  40                  45

Leu Val Glu Leu Pro Ala Ser Phe Arg Glu Leu Leu Thr Phe Phe Cys

```
        50                  55                  60
Thr Asn Ala Thr Ile His Gly Ala Ile Arg Leu Val Cys Ser Arg Gly
 65                  70                  75                  80

Asn Arg Leu Lys Thr Thr Ser Trp Gly Leu Leu Ser Leu Gly Ala Leu
                 85                  90                  95

Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
            115                 120                 125

Pro Leu Val Thr Leu Cys Asp Gly Asn Pro Arg Pro Ser Pro Val
130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
            195                 200                 205

Leu Cys Asn Ser Thr Gly Gly Asp Cys Phe Tyr Arg Gly Tyr Thr Ser
            210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
            275                 280                 285

Val Asp Gly Val Trp Thr Ala Gln Arg Pro Gly Ile Thr His Gly Val
290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
            355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
            420                 425                 430

Phe Tyr Arg Leu Tyr Gln Asp Leu Glu Thr His Arg Leu Pro Cys Thr
            435                 440                 445

Ser Arg Cys Pro Arg Pro Cys Arg Glu Ser Ala Phe Lys Leu Ser Thr
            450                 455                 460

Gly Thr Ser Arg Trp Pro Ser Ala Lys Ser Ala Gly Trp Thr Leu Ala
465                 470                 475                 480
```

```
Thr Leu Gly Glu Gln Gly Leu Pro His Gln Ser His Arg Gln Arg Ser
                485                 490                 495
Ser Leu Ala Lys Ile Asn Ile Val Tyr Gln Glu Leu Asn Tyr Arg Ser
                500                 505                 510
Val Glu Glu Ala Pro Val Tyr Ser Val Pro Gln Leu Leu Ser Ala Met
                515                 520                 525
Gly Ser Leu Tyr Ser Leu Trp Phe Gly Ala Ser Val Leu Ser Leu Leu
                530                 535                 540
Glu Leu Leu Glu Leu Leu Leu Asp Ala Ser Ala Leu Thr Leu Val Leu
545                 550                 555                 560
Gly Gly Arg Arg Leu Arg Arg Ala Trp Phe Ser Trp Pro Arg Ala Ser
                565                 570                 575
Pro Ala Ser Gly Ala Ser Ser Ile Lys Pro Glu Ala Ser Gln Met Pro
                580                 585                 590
Pro Pro Ala Gly Gly Thr Ser Asp Asp Pro Glu Pro Ser Gly Pro His
                595                 600                 605
Leu Pro Arg Val Met Leu Pro Gly Val Leu Ala Gly Val Ser Ala Glu
                610                 615                 620
Glu Ser Trp Ala Gly Pro Gln Pro Leu Glu Thr Leu Asp Thr
625                 630                 635

<210> SEQ ID NO 9
<211> LENGTH: 638
<212> TYPE: PRT
<213> ORGANISM: Homo Sapiens

<400> SEQUENCE: 9

Met Ala Glu His Arg Ser Met Asp Gly Arg Met Glu Ala Ala Thr Arg
1               5                   10                  15
Gly Gly Ser His Leu Gln Ala Ala Ala Gln Thr Pro Pro Arg Pro Gly
                20                  25                  30
Pro Pro Ser Ala Pro Pro Pro Pro Lys Glu Gly His Gln Glu Gly
                35                  40                  45
Leu Val Glu Leu Pro Ala Ser Phe Arg Glu Leu Leu Thr Phe Phe Cys
                50                  55                  60
Thr Asn Ala Thr Ile His Gly Ala Ile Arg Leu Val Cys Ser Arg Gly
65                  70                  75                  80
Asn Arg Leu Lys Thr Thr Ser Trp Gly Leu Leu Ser Leu Gly Ala Leu
                85                  90                  95
Val Ala Leu Cys Trp Gln Leu Gly Leu Leu Phe Glu Arg His Trp His
                100                 105                 110
Arg Pro Val Leu Met Ala Val Ser Val His Ser Glu Arg Lys Leu Leu
                115                 120                 125
Pro Leu Val Thr Leu Cys Asp Gly Asn Pro Arg Arg Pro Ser Pro Val
                130                 135                 140
Leu Arg His Leu Glu Leu Leu Asp Glu Phe Ala Arg Glu Asn Ile Asp
145                 150                 155                 160
Ser Leu Tyr Asn Val Asn Leu Ser Lys Gly Arg Ala Ala Leu Ser Ala
                165                 170                 175
Thr Val Pro Arg His Glu Pro Pro Phe His Leu Asp Arg Glu Ile Arg
                180                 185                 190
Leu Gln Arg Leu Ser His Ser Gly Ser Arg Val Arg Val Gly Phe Arg
                195                 200                 205
Leu Cys Asn Ser Thr Gly Gly Asp Cys Phe Tyr Arg Gly Tyr Thr Ser
```

-continued

```
            210                 215                 220
Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
                260                 265                 270

Arg Gln Phe Arg Thr Phe His His Pro Thr Tyr Gly Ser Cys Tyr Thr
                275                 280                 285

Val Asp Gly Val Trp Thr Ala Gln Arg Pro Gly Ile Thr His Gly Val
290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
                340                 345                 350

Ile Ser Ile Arg Glu Asp Glu Val His Arg Leu Gly Ser Pro Tyr Gly
                355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
                420                 425                 430

Phe Tyr Arg Leu Tyr Gln Asp Leu Glu Thr His Arg Leu Pro Cys Thr
                435                 440                 445

Ser Arg Cys Pro Arg Pro Cys Arg Glu Ser Ala Phe Lys Leu Ser Thr
                450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
                500                 505                 510

Val Glu Glu Ala Pro Val Tyr Ser Val Pro Gln Leu Leu Ser Ala Met
                515                 520                 525

Gly Ser Leu Cys Ser Leu Trp Phe Gly Ala Ser Val Leu Ser Leu Leu
                530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
                580                 585                 590

Pro Pro Ala Gly Gly Thr Ser Asp Asp Pro Glu Pro Ser Gly Pro His
                595                 600                 605

Leu Pro Arg Val Met Leu Pro Gly Val Leu Ala Gly Val Ser Ala Glu
                610                 615                 620

Glu Ser Trp Ala Gly Pro Gln Pro Leu Glu Thr Leu Asp Thr
625                 630                 635
```

<210> SEQ ID NO 10
<211> LENGTH: 11
<212> TYPE: PRT
<213> ORGANISM: Homo Sapiens

<400> SEQUENCE: 10

Met Gly Ser Gln Trp Ser Leu Trp Phe Gly Ala
1               5                   10

<210> SEQ ID NO 11
<211> LENGTH: 11
<212> TYPE: PRT
<213> ORGANISM: Homo Sapiens

<400> SEQUENCE: 11

Met Gly Ser Leu Tyr Ser Leu Trp Phe Gly Ala
1               5                   10

<210> SEQ ID NO 12
<211> LENGTH: 11
<212> TYPE: PRT
<213> ORGANISM: Homo Sapiens

<400> SEQUENCE: 12

Met Gly Ser Leu Cys Ser Leu Trp Phe Gly Ala
1               5                   10

<210> SEQ ID NO 13
<211> LENGTH: 649
<212> TYPE: PRT
<213> ORGANISM: Homo Sapiens

<400> SEQUENCE: 13

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
                20                  25                  30

Cys Leu Asn Thr Asn Thr His Gly Cys Arg Arg Ile Val Val Ser Arg
            35                  40                  45

Gly Arg Leu Arg Arg Leu Leu Trp Ile Gly Phe Thr Leu Thr Ala Val
        50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Pro
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser

```
                195                 200                 205
Asn Asp Thr Ser Asp Cys Ala Thr Tyr Thr Phe Ser Leu Gly Ile Asn
210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
                260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
        290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
                340                 345                 350

Thr Ser Ile Gly Met His Leu Thr Glu Ser Phe Lys Leu Ser Glu Pro
            355                 360                 365

Tyr Ser Gln Cys Thr Glu Asp Gly Ser Asp Val Pro Ile Arg Asn Ile
        370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
                420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Ser Leu Lys Glu Trp Thr Leu
        450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
        530                 535                 540

Cys Val Val Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
                580                 585                 590

Asn Pro Ala Leu Asp Ile Asp Asp Asp Leu Pro Thr Phe Asn Ser Ala
            595                 600                 605

Leu His Leu Pro Pro Ala Leu Gly Thr Gln Val Pro Gly Thr Pro Pro
        610                 615                 620
```

```
Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 14
<211> LENGTH: 649
<212> TYPE: PRT
<213> ORGANISM: Homo Sapiens

<400> SEQUENCE: 14

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
                20                  25                  30

Cys Leu Asn Thr Asn Thr His Gly Cys Arg Arg Ile Val Val Ser Arg
                35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Ala
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
                100                 105                 110

Leu Leu Ala Asp Leu Glu Gln Glu Thr Arg Glu Ala Leu Lys Ser Leu
            115                 120                 125

Tyr Gly Phe Pro Glu Ser Arg Lys Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
                180                 185                 190

Val Met His Ile Glu Ser Lys Gln Val Val Gly Phe Gln Leu Cys Ser
            195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
                260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
```

-continued

```
                340                 345                 350
Thr Ser Ile Gly Met His Leu Thr Glu Ser Phe Lys Leu Ser Glu Pro
            355                 360                 365
Tyr Ser Gln Cys Thr Glu Asp Gly Ser Asp Val Pro Ile Arg Asn Ile
        370                 375                 380
Tyr Asn Ala Ala Tyr Ser Leu Gln Ile Cys Leu His Ser Cys Phe Gln
385                 390                 395                 400
Thr Lys Met Val Glu Lys Cys Gly Cys Ala Gln Tyr Ser Gln Pro Leu
                405                 410                 415
Pro Pro Ala Ala Asn Tyr Cys Asn Tyr Gln Gln His Pro Asn Trp Met
            420                 425                 430
Tyr Cys Tyr Tyr Gln Leu His Arg Ala Phe Val Gln Glu Glu Leu Gly
        435                 440                 445
Cys Gln Ser Val Cys Lys Glu Ala Cys Ser Phe Lys Glu Trp Thr Leu
    450                 455                 460
Thr Thr Ser Leu Ala Gln Trp Pro Ser Val Val Ser Glu Lys Trp Leu
465                 470                 475                 480
Leu Pro Val Leu Thr Trp Asp Gln Gly Arg Gln Val Asn Lys Lys Leu
                485                 490                 495
Asn Lys Thr Asp Leu Ala Lys Leu Leu Ile Phe Tyr Lys Asp Leu Asn
            500                 505                 510
Gln Arg Ser Ile Met Glu Ser Pro Ala Asn Ser Ile Glu Met Leu Leu
        515                 520                 525
Ser Asn Phe Gly Gly Gln Leu Gly Leu Trp Met Ser Cys Ser Val Val
    530                 535                 540
Cys Val Ile Glu Ile Ile Glu Val Phe Phe Ile Asp Phe Phe Ser Ile
545                 550                 555                 560
Ile Ala Arg Arg Gln Trp Gln Lys Ala Lys Glu Trp Trp Ala Trp Lys
                565                 570                 575
Gln Ala Pro Pro Cys Pro Glu Ala Pro Arg Ser Pro Gln Gly Gln Asp
            580                 585                 590
Asn Pro Ala Leu Asp Ile Asp Asp Leu Pro Thr Phe Asn Ser Ala
        595                 600                 605
Leu His Leu Pro Pro Ala Leu Gly Thr Gln Val Pro Gly Thr Pro Pro
    610                 615                 620
Pro Lys Tyr Asn Thr Leu Arg Leu Glu Arg Ala Phe Ser Asn Ser Leu
625                 630                 635                 640
Thr Asp Thr Gln Met Leu Asp Glu Leu
                645

<210> SEQ ID NO 15
<211> LENGTH: 649
<212> TYPE: PRT
<213> ORGANISM: Homo Sapiens

<400> SEQUENCE: 15

Met Ala Pro Gly Glu Lys Ile Lys Ala Lys Ile Lys Lys Asn Leu Pro
1               5                   10                  15
Val Thr Gly Pro Gln Ala Pro Thr Ile Lys Glu Leu Met Arg Trp Tyr
            20                  25                  30
Cys Leu Asn Thr Asn Thr His Gly Cys Arg Arg Ile Val Val Ser Arg
        35                  40                  45
Gly Arg Leu Arg Arg Leu Leu Trp Ile Gly Phe Thr Leu Thr Ala Val
    50                  55                  60
```

-continued

```
Ala Leu Ile Leu Trp Gln Cys Ala Leu Leu Val Phe Ser Phe Tyr Thr
 65                  70                  75                  80

Val Ser Val Ser Ile Lys Val His Phe Arg Lys Leu Asp Phe Pro Ala
                 85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Glu Ala Glu Ser Trp Asn
130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Thr
                165                 170                 175

Gly Arg Lys Arg Lys Val Gly Gly Ser Ile Ile His Lys Ala Ser Asn
                180                 185                 190

Val Met His Ile Glu Ser Lys Gln Val Val Gly Phe Gln Leu Cys Ser
            195                 200                 205

Asn Asp Thr Ser Asp Cys Ala Thr Tyr Thr Phe Ser Ser Gly Ile Asn
210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
        275                 280                 285

Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
```

```
                        485                 490                 495
Asn Lys Thr Asp Leu Ala Lys Leu Leu Ile Phe Tyr Lys Asp Leu Asn
                500                 505                 510
Gln Arg Ser Ile Met Glu Ser Pro Ala Asn Ser Ile Glu Met Leu Leu
            515                 520                 525
Ser Asn Phe Gly Gly Gln Leu Gly Leu Trp Met Ser Cys Ser Val Val
        530                 535                 540
Cys Val Ile Glu Ile Ile Glu Val Phe Phe Ile Asp Phe Phe Ser Ile
545                 550                 555                 560
Ile Ala Arg Arg Gln Trp Gln Lys Ala Lys Glu Trp Trp Ala Trp Lys
                565                 570                 575
Gln Ala Pro Pro Cys Pro Glu Ala Pro Arg Ser Pro Gln Gly Gln Asp
            580                 585                 590
Asn Pro Ala Leu Asp Ile Asp Asp Gly Leu Pro Thr Phe Asn Ser Ala
        595                 600                 605
Leu His Leu Pro Pro Ala Leu Gly Thr Gln Val Pro Gly Thr Pro Pro
    610                 615                 620
Pro Lys Tyr Asn Thr Leu Arg Leu Glu Arg Ala Phe Ser Asn Gln Leu
625                 630                 635                 640
Thr Asp Thr Gln Met Leu Asp Glu Leu
                645

<210> SEQ ID NO 16
<211> LENGTH: 649
<212> TYPE: PRT
<213> ORGANISM: Homo Sapiens

<400> SEQUENCE: 16

Met Ala Pro Gly Glu Lys Ile Lys Ala Lys Ile Lys Lys Asn Leu Pro
1               5                   10                  15
Val Thr Gly Pro Gln Ala Pro Thr Ile Lys Glu Leu Met Arg Trp Tyr
            20                  25                  30
Cys Leu Asn Thr Asn Thr His Gly Cys Arg Arg Ile Val Val Ser Arg
        35                  40                  45
Gly Arg Leu Arg Arg Leu Leu Trp Ile Gly Phe Thr Leu Thr Ala Val
    50                  55                  60
Ala Leu Ile Leu Trp Gln Cys Ala Leu Leu Val Phe Ser Phe Tyr Thr
65                  70                  75                  80
Val Ser Val Ser Ile Lys Val His Phe Arg Lys Leu Asp Phe Pro Ala
                85                  90                  95
Val Thr Ile Cys Asn Ile Asn Pro Tyr Lys Tyr Ser Thr Val Arg His
            100                 105                 110
Leu Leu Ala Asp Leu Glu Gln Glu Thr Arg Glu Ala Leu Lys Ser Leu
        115                 120                 125
Tyr Gly Phe Pro Glu Ser Arg Lys Arg Arg Glu Ala Glu Ser Trp Asn
    130                 135                 140
Ser Val Ser Glu Gly Lys Gln Pro Arg Phe Ser His Arg Ile Pro Leu
145                 150                 155                 160
Leu Ile Phe Asp Gln Asp Glu Lys Gly Lys Ala Arg Asp Phe Phe Thr
                165                 170                 175
Gly Arg Lys Arg Lys Val Gly Gly Ser Ile Ile His Lys Ala Ser Asn
            180                 185                 190
Val Met His Ile Glu Ser Lys Gln Val Val Gly Phe Gln Leu Cys Ser
        195                 200                 205
```

-continued

Asn Asp Thr Ser Asp Cys Ala Thr Tyr Thr Phe Ser Ser Gly Ile Asn
210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
            245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile His Arg Gln Asp Glu
            325                 330                 335

Tyr Pro Ser Val Glu Asp Val Gly Thr Glu Ile Glu Thr Thr Met Val
            340                 345                 350

Thr Ser Ile Gly Met His Leu Thr Glu Ser Phe Lys Leu Ser Glu Pro
            355                 360                 365

Ser Ser Gln Cys Thr Glu Gly Gly Ser Asp Val Pro Ile Arg Asn Ile
370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
            405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Arg Phe Lys Glu Trp Thr Leu
450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
            485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
            565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
            595                 600                 605

Leu His Leu Pro Pro Ala Leu Gly Thr Gln Val Pro Gly Thr Pro Pro
610                 615                 620

Pro Lys Tyr Asn Thr Leu Arg Leu Glu Arg Ala Phe Ser Asn Gln Leu

```
                625                 630                 635                 640
Thr Asp Thr Gln Met Leu Asp Glu Leu
                645

<210> SEQ ID NO 17
<211> LENGTH: 638
<212> TYPE: PRT
<213> ORGANISM: Homo Sapiens

<400> SEQUENCE: 17

Met Ala Glu His Arg Ser Met Asp Gly Arg Met Glu Ala Ala Thr Arg
1               5                   10                  15

Gly Gly Ser His Leu Gln Ala Ala Gln Thr Pro Pro Arg Pro Gly
            20                  25                  30

Pro Pro Ser Ala Pro Pro Pro Lys Glu Gly His Gln Glu Gly
        35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65              70                  75                  80

Asn Arg Leu Lys Thr Thr Ser Trp Gly Leu Ser Leu Gly Ala Leu
            85                  90                  95

Val Ala Leu Cys Trp Gln Leu Gly Leu Leu Phe Glu Arg His Trp His
        100                 105                 110

Arg Pro Val Leu Met Ala Val Ser Val His Ser Glu Arg Lys Leu Leu
    115                 120                 125

Pro Leu Val Thr Leu Cys Asp Gly Asn Pro Arg Arg Pro Ser Pro Val
    130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
    210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Ile His His Pro Thr Tyr Gly Ser Cys Tyr Thr
        275                 280                 285

Val Asp Gly Val Trp Thr Ala Gln Arg Pro Gly Ile Thr His Gly Val
    290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350
```

```
Ile Arg Ile Arg Glu Asp Glu Val His Arg Leu Gly Ser Pro Tyr Gly
        355                 360                 365

His Cys Thr Ala Gly Gly Gly Val Glu Val Glu Leu Leu His Asn
    370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
                420                 425                 430

Phe Tyr Arg Leu Tyr Gln Asp Leu Glu Thr His Arg Leu Pro Cys Thr
            435                 440                 445

Ser Arg Cys Pro Arg Pro Cys Arg Glu Ser Ala Phe Lys Leu Ser Thr
        450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
                500                 505                 510

Val Glu Glu Ala Pro Val Tyr Ser Val Pro Gln Leu Leu Ser Ala Met
            515                 520                 525

Gly Ser Leu Cys Ser Leu Trp Phe Gly Ala Ser Val Leu Ser Leu Leu
        530                 535                 540

Glu Leu Leu Glu Leu Leu Leu Asp Ala Ser Ala Leu Thr Leu Val Leu
545                 550                 555                 560

Gly Gly Arg Arg Leu His Arg Ala Trp Phe Ser Trp Pro Arg Ala Ser
                565                 570                 575

Pro Ala Ser Gly Ala Ser Ser Ile Lys Pro Glu Ala Ser Gln Met Pro
            580                 585                 590

Pro Pro Ala Gly Gly Thr Ser Asp Asp Pro Glu Pro Ser Gly Pro His
        595                 600                 605

Leu Pro Arg Val Met Leu Pro Gly Val Leu Ala Gly Val Ser Ala Glu
        610                 615                 620

Glu Ser Trp Ala Gly Pro Gln Pro Leu Glu Thr Leu Asp Thr
625                 630                 635

<210> SEQ ID NO 18
<211> LENGTH: 638
<212> TYPE: PRT
<213> ORGANISM: Homo Sapiens

<400> SEQUENCE: 18

Met Ala Glu His Arg Ser Met Asp Gly Arg Met Glu Ala Ala Thr Arg
1               5                   10                  15

Gly Gly Ser His Leu Gln Ala Ala Gln Thr Pro Arg Pro Gly
                20                  25                  30

Pro Pro Ser Ala Pro Pro Pro Lys Glu Gly His Gln Glu Gly
            35                  40                  45

Leu Val Glu Leu Pro Ala Ser Phe Arg Glu Leu Leu Thr Phe Phe Cys
        50                  55                  60

Thr Asn Ala Thr Ile His Gly Ala Ile Arg Leu Val Cys Ser Arg Gly
65              70                  75                  80

Asn Arg Leu Lys Thr Thr Ser Trp Gly Leu Leu Ser Leu Gly Ala Leu
                85                  90                  95
```

```
Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
        115                 120                 125

Pro Leu Val Thr Leu Cys Asp Gly Asn Pro Arg Arg Pro Ser Pro Val
130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
        275                 280                 285

Val Asp Gly Val Trp Thr Ala Gln Arg Pro Gly Ile Thr His Gly Val
290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
        355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
            420                 425                 430

Phe Tyr Arg Leu Tyr Gln Asp Leu Glu Thr His Arg Leu Pro Cys Thr
        435                 440                 445

Ser Arg Cys Pro Arg Pro Cys Arg Glu Ser Ala Phe Lys Leu Ser Thr
450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
            500                 505                 510
```

```
Val Glu Glu Ala Pro Val Tyr Ser Val Pro Gln Leu Leu Ser Ala Met
            515                 520                 525

Gly Ser Leu Cys Ser Leu Trp Phe Gly Ala Ser Val Leu Ser Leu Leu
        530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
            580                 585                 590

Pro Pro Ala Gly Gly Thr Ser Asp Asp Pro Glu Pro Ser Gly Pro His
        595                 600                 605

Leu Pro Arg Val Met Leu Pro Gly Val Leu Ala Gly Val Ser Ala Glu
    610                 615                 620

Glu Ser Trp Ala Gly Pro Gln Pro Leu Glu Thr Leu Asp Thr
625                 630                 635

<210> SEQ ID NO 19
<211> LENGTH: 638
<212> TYPE: PRT
<213> ORGANISM: Homo Sapiens

<400> SEQUENCE: 19

Met Ala Glu His Arg Ser Met Asp Gly Arg Met Glu Ala Ala Thr Arg
1               5                   10                  15

Gly Gly Pro His Leu Gln Ala Ala Gln Thr Pro Pro Arg Pro Gly
            20                  25                  30

Pro Pro Ser Ala Pro Pro Pro Pro Lys Glu Gly His Gln Glu Gly
        35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
        115                 120                 125

Pro Leu Val Thr Leu Cys Asp Gly Asn Pro Arg Arg Pro Ser Pro Val
    130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Pro His Glu Pro Pro Phe His Leu Asp Arg Glu Ile Arg
            180                 185                 190

Leu Gln Ser Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
    210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255
```

Gly His Phe Val Leu Ser Cys Ser Tyr Asp Gly Leu Asp Cys Gln Ala
              260                 265                 270

Arg Gln Phe Arg Thr Phe His His Pro Thr Tyr Gly Ser Cys Tyr Thr
          275                 280                 285

Val Asp Gly Val Trp Thr Ala Gln Arg Pro Gly Ile Thr His Gly Val
      290                 295                 300

Gly Leu Val Leu Arg Val Glu Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
              340                 345                 350

Ile Ser Ile Arg Glu Asp Glu Val His Arg Leu Gly Ser Pro Tyr Gly
          355                 360                 365

His Cys Thr Ala Gly Gly Glu Gly Val Glu Val Glu Leu Leu His Asn
      370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
              420                 425                 430

Phe Tyr Arg Leu Tyr Gln Asp Leu Glu Thr His Arg Leu Pro Cys Thr
          435                 440                 445

Ser Arg Cys Pro Arg Pro Cys Arg Glu Ser Ala Phe Lys Leu Ser Thr
      450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
              500                 505                 510

Val Glu Glu Ala Pro Val Tyr Ser Val Pro Gln Leu Leu Ser Ala Met
          515                 520                 525

Gly Ser Leu Cys Ser Leu Trp Phe Gly Ala Ser Val Leu Ser Leu Leu
      530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
              580                 585                 590

Pro Pro Ala Gly Gly Thr Ser Asp Asp Pro Glu Pro Ser Gly Pro His
          595                 600                 605

Leu Pro Arg Val Met Leu Pro Gly Val Leu Ala Gly Val Ser Ala Glu
      610                 615                 620

Glu Ser Trp Ala Gly Pro Gln Pro Leu Glu Thr Leu Asp Lys
625                 630                 635

<210> SEQ ID NO 20
<211> LENGTH: 638
<212> TYPE: PRT
<213> ORGANISM: Homo Sapiens

<400> SEQUENCE: 20

```
Met Ala Glu His Arg Ser Met Asp Gly Arg Met Glu Ala Ala Thr Arg
1               5                   10                  15

Gly Gly Pro His Leu Gln Ala Ala Gln Thr Pro Arg Pro Gly
            20                  25                  30

Pro Pro Ser Ala Pro Pro Pro Lys Glu Gly His Gln Glu Gly
            35                  40                  45

Leu Val Glu Leu Pro Ala Ser Phe Arg Glu Leu Leu Thr Phe Phe Cys
        50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
                100                 105                 110

Arg Pro Val Leu Met Ala Val Ser Val His Ser Glu Arg Lys Leu Leu
                115                 120                 125

Pro Leu Val Thr Leu Cys Asp Gly Asn Pro Arg Arg Pro Ser Pro Val
130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
                180                 185                 190

Leu Gln Arg Leu Ser His Ser Gly Ser Arg Val Arg Val Gly Phe Arg
                195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
                260                 265                 270

Arg Gln Phe Arg Thr Phe His His Pro Thr Tyr Gly Ser Cys Tyr Thr
                275                 280                 285

Val Asp Gly Val Trp Thr Ala Gln Arg Pro Gly Ile Thr His Gly Val
                290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
                340                 345                 350

Ile Ser Ile Arg Glu Asp Glu Val His Arg Leu Gly Ser Pro Tyr Gly
                355                 360                 365

His Cys Thr Ala Gly Gly Glu Gly Val Glu Val Glu Leu Leu His Asn
                370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415
```

-continued

Gly Ala Glu Tyr Cys Ser Ser Ala Arg His Pro Ala Trp Gly His Cys
          420                 425                 430

Phe Tyr Arg Leu Tyr Gln Asp Leu Glu Thr His Arg Leu Pro Cys Thr
          435                 440                 445

Ser Arg Cys Pro Arg Pro Cys Arg Glu Ser Ala Phe Lys Leu Ser Thr
450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
              485                 490                 495

Ser Leu Ala Lys Ile Asn Ile Val Tyr Gln Gly Leu Asn Tyr Arg Ser
          500                 505                 510

Val Glu Glu Ala Pro Val Tyr Ser Val Pro Gln Leu Leu Ser Ala Met
          515                 520                 525

Gly Ser Leu Cys Ser Leu Trp Phe Gly Ala Ser Val Leu Ser Leu Leu
          530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
              565                 570                 575

Pro Ala Ser Gly Ala Ser Ser Ile Lys Pro Glu Ala Ser Gln Met Pro
          580                 585                 590

Pro Pro Ala Gly Gly Thr Ser Asp Asp Pro Glu Pro Ser Gly Pro His
          595                 600                 605

Leu Pro Arg Val Met Leu Pro Gly Val Leu Ala Gly Val Ser Ala Glu
          610                 615                 620

Glu Ser Trp Ala Gly Pro Gln Pro Leu Glu Thr Leu Asp Thr
625                 630                 635

<210> SEQ ID NO 21
<211> LENGTH: 638
<212> TYPE: PRT
<213> ORGANISM: Homo Sapiens

<400> SEQUENCE: 21

Met Ala Glu His Arg Ser Met Asp Gly Arg Met Glu Ala Ala Thr Arg
1               5                   10                  15

Gly Gly Ser His Leu Gln Ala Ala Gln Thr Pro Pro Arg Pro Gly
          20                  25                  30

Pro Pro Ser Ala Pro Pro Pro Pro Lys Glu Gly His Gln Glu Gly
          35                  40                  45

Leu Val Glu Leu Pro Ala Ser Phe Arg Glu Leu Leu Thr Phe Phe Cys
          50                  55                  60

Thr Asn Ala Thr Ile His Gly Thr Ile Arg Leu Val Cys Ser Arg Gly
65                  70                  75                  80

Asn Arg Leu Lys Thr Thr Ser Trp Gly Leu Leu Ser Leu Gly Ala Leu
              85                  90                  95

Val Ala Leu Cys Trp Gln Leu Gly Leu Leu Phe Glu Arg His Trp His
          100                 105                 110

Arg Pro Val Leu Met Ala Val Ser Val His Ser Glu Arg Lys Leu Leu
          115                 120                 125

Pro Leu Val Thr Leu Cys Asp Gly Asn Pro Arg Arg Pro Ser Pro Val
          130                 135                 140

Leu Arg His Leu Glu Leu Leu Asp Glu Phe Ala Arg Glu Asn Ile Asp

```
            145                 150                 155                 160
Ser Leu Tyr Asn Val Asn Leu Ser Lys Gly Arg Ala Ala Leu Ser Ala
                165                 170                 175

Thr Val Pro Pro His Glu Pro Phe His Leu Asp Arg Glu Ile Arg
            180                 185                 190

Leu Gln Arg Leu Ser His Ser Gly Ser Arg Val Arg Val Gly Phe Arg
            195                 200                 205

Leu Cys Asn Ser Thr Gly Gly Asp Cys Phe Tyr Arg Gly Tyr Thr Ser
            210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
            275                 280                 285

Val Asp Gly Val Trp Thr Ala Gln Arg Pro Gly Ile Thr His Gly Val
            290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
            355                 360                 365

His Cys Thr Ala Gly Glu Gly Val Glu Val Gln Leu Leu His Asn
            370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
            420                 425                 430

Phe Tyr Arg Leu Tyr Arg Asp Leu Glu Thr His Arg Leu Pro Cys Thr
            435                 440                 445

Ser Arg Cys Pro Arg Pro Cys Arg Glu Ser Ala Phe Lys Leu Ser Thr
            450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
            500                 505                 510

Val Glu Glu Ala Pro Val Tyr Ser Val Pro Gln Leu Leu Ser Ala Met
            515                 520                 525

Gly Ser Leu Cys Ser Leu Trp Phe Gly Ala Ser Val Leu Ser Leu Leu
            530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575
```

Pro Ala Ser Gly Ala Ser Ser Ile Lys Pro Glu Ala Gly Gln Met Pro
            580                 585                 590

Pro Pro Ala Gly Gly Thr Ser Asp Asp Pro Glu Pro Ser Gly Pro His
        595                 600                 605

Leu Pro Arg Val Met Leu Pro Gly Val Leu Ala Gly Val Ser Ala Glu
            610                 615                 620

Glu Ser Trp Ala Gly Pro Gln Pro Leu Glu Thr Leu Asp Thr
625                 630                 635

<210> SEQ ID NO 22
<211> LENGTH: 638
<212> TYPE: PRT
<213> ORGANISM: Homo Sapiens

<400> SEQUENCE: 22

Met Ala Glu His Arg Ser Met Asp Gly Arg Met Glu Ala Ala Thr Arg
1               5                   10                  15

Gly Gly Ser His Leu Gln Ala Ala Gln Thr Pro Arg Pro Gly
            20                  25                  30

Pro Pro Ser Ala Pro Pro Pro Pro Lys Glu Gly His Gln Glu Gly
            35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
            100                 105                 110

Arg Pro Val Leu Met Ala Val Ser His Ser Glu Arg Lys Leu Leu
        115                 120                 125

Pro Leu Val Thr Leu Cys Asp Gly Asn Pro Arg Arg Pro Ser Pro Val
    130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
    210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
        275                 280                 285

Val Asp Gly Val Trp Thr Ala Gln Arg Pro Gly Ile Thr His Gly Val
    290                 295                 300

Gly Leu Val Leu Arg Val Glu Gln Gln Pro His Leu Pro Leu Leu Ser

```
            305                 310                 315                 320
Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
                340                 345                 350

Ile Ser Ile Arg Glu Asp Glu Val His Arg Leu Gly Ser Pro Tyr Gly
                355                 360                 365

His Cys Thr Ala Gly Glu Gly Val Glu Val Glu Leu Leu His Asn
    370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
                420                 425                 430

Phe Tyr Arg Leu Tyr Gln Asp Leu Glu Thr His Arg Leu Pro Cys Thr
                435                 440                 445

Ser Arg Cys Pro Arg Pro Cys Arg Glu Ser Ala Phe Lys Leu Ser Thr
    450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Gly His Arg Gln Arg Ser
                485                 490                 495

Ser Leu Ala Lys Ile Asn Ile Val Tyr Gln Glu Leu Asn Tyr Arg Ser
                500                 505                 510

Val Glu Glu Ala Pro Val Tyr Ser Val Pro Gln Leu Leu Ser Ala Met
                515                 520                 525

Gly Ser Leu Cys Ser Leu Trp Phe Gly Ala Ser Val Leu Ser Leu Leu
                530                 535                 540

Glu Leu Leu Glu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
                580                 585                 590

Pro Pro Ala Gly Gly Thr Ser Asp Asp Pro Glu Pro Ser Gly Pro His
                595                 600                 605

Leu Pro Arg Val Met Leu Pro Gly Val Leu Ala Gly Val Ser Ala Glu
                610                 615                 620

Glu Ser Trp Ala Gly Pro Gln Pro Leu Glu Thr Leu Asp Thr
625                 630                 635

<210> SEQ ID NO 23
<211> LENGTH: 638
<212> TYPE: PRT
<213> ORGANISM: Homo Sapiens

<400> SEQUENCE: 23

Met Ala Glu His Arg Ser Met Asp Gly Arg Met Glu Ala Ala Thr Arg
1               5                   10                  15

Gly Gly Ser His Leu Gln Ala Ala Gln Thr Pro Arg Pro Arg Pro Gly
                20                  25                  30

Pro Pro Ser Ala Pro Pro Pro Pro Lys Glu Gly His Gln Glu Gly
            35                  40                  45
```

-continued

```
Leu Val Glu Leu Pro Ala Ser Phe Arg Glu Leu Leu Thr Phe Phe Cys
 50                  55                  60

Thr Asn Ala Thr Ile His Gly Ala Ile Arg Leu Val Cys Ser Arg Gly
 65                  70                  75                  80

Asn Arg Leu Lys Thr Thr Ser Trp Gly Leu Leu Ser Leu Gly Ala Leu
                 85                  90                  95

Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
            115                 120                 125

Pro Leu Val Thr Leu Cys Asp Gly Asn Pro Arg Arg Pro Ser Pro Val
130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Pro His Glu Pro Pro Phe His Leu Asp Arg Glu Ile Arg
            180                 185                 190

Leu Gln Arg Leu Ser His Ser Gly Ser Arg Val Arg Val Gly Phe Arg
            195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
            275                 280                 285

Val Asp Gly Val Trp Thr Ala Gln Arg Pro Gly Ile Thr His Gly Val
290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
            355                 360                 365

His Cys Thr Ala Gly Gly Glu Gly Val Glu Val Gln Pro Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
            420                 425                 430

Phe Tyr Arg Leu Tyr Gln Asp Leu Glu Thr His Arg Leu Pro Cys Thr
            435                 440                 445

Ser Arg Cys Pro Arg Pro Cys Arg Glu Ser Ala Phe Lys Leu Ser Thr
450                 455                 460

Gly Thr Ser Arg Trp Pro Ser Ala Lys Ser Ala Gly Trp Thr Leu Ala
```

```
                465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
                500                 505                 510

Val Glu Glu Ala Pro Val Tyr Ser Val Pro Gln Leu Leu Ser Ala Met
                515                 520                 525

Gly Ser Leu Cys Ser Leu Trp Phe Gly Ala Ser Val Leu Ser Leu Leu
            530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
                580                 585                 590

Pro Pro Ala Gly Gly Thr Ser Asp Asp Pro Glu Pro Ser Gly Pro His
            595                 600                 605

Leu Pro Arg Val Met Leu Pro Gly Val Leu Ala Gly Val Ser Ala Glu
            610                 615                 620

Glu Ser Trp Ala Gly Pro Gln Pro Leu Glu Thr Leu Asp Thr
625                 630                 635

<210> SEQ ID NO 24
<211> LENGTH: 638
<212> TYPE: PRT
<213> ORGANISM: Homo Sapiens

<400> SEQUENCE: 24

Met Ala Glu His Arg Ser Met Asp Gly Arg Met Glu Ala Ala Thr Arg
1               5                   10                  15

Gly Gly Ser His Leu Gln Ala Ala Ala Gln Thr Pro Pro Arg Pro Gly
                20                  25                  30

Pro Pro Ser Ala Pro Pro Pro Pro Lys Glu Gly His Gln Glu Gly
            35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
                100                 105                 110

Arg Pro Val Leu Met Ala Val Ser Val His Ser Glu Arg Lys Leu Leu
            115                 120                 125

Pro Leu Val Thr Leu Cys Asp Gly Asn Pro Arg Arg Pro Ser Pro Val
            130                 135                 140

Leu Arg His Leu Glu Leu Leu Asp Glu Phe Ala Arg Glu Asn Ile Asp
145                 150                 155                 160

Ser Leu Tyr Ser Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
            195                 200                 205
```

-continued

```
Leu Cys Asn Ser Thr Gly Gly Asp Cys Phe Tyr Arg Gly Tyr Thr Ser
    210                 215                 220
Gly Val Ala Ala Val Gln Asp Trp Tyr His Phe His Tyr Val Asp Ile
225                 230                 235                 240
Leu Ala Leu Leu Pro Ala Ala Trp Glu Asp Ser His Gly Ser Gln Asp
                245                 250                 255
Gly His Phe Val Leu Ser Cys Ser Tyr Asp Gly Leu Asp Cys Gln Ala
            260                 265                 270
Arg Gln Phe Arg Thr Phe His His Pro Thr Tyr Gly Ser Cys Tyr Thr
        275                 280                 285
Val Asp Gly Val Trp Thr Ala Gln Arg Pro Gly Ile Thr His Gly Val
290                 295                 300
Gly Leu Val Leu Arg Val Glu Gln Gln Pro His Leu Pro Leu Leu Ser
305                 310                 315                 320
Thr Leu Ala Gly Ile Arg Val Met Val His Gly Arg Asn His Thr Pro
                325                 330                 335
Phe Leu Gly His His Ser Phe Ser Val Arg Pro Gly Thr Glu Ala Thr
            340                 345                 350
Ile Ser Ile Arg Glu Asp Glu Val His Arg Leu Gly Ser Pro Tyr Gly
        355                 360                 365
His Cys Thr Ala Gly Gly Glu Gly Val Glu Val Glu Leu Leu His Asn
370                 375                 380
Thr Ser Tyr Thr Arg Gln Pro Cys Leu Val Ser Cys Phe Gln Gln Leu
385                 390                 395                 400
Met Val Glu Thr Cys Ser Cys Gly Tyr Tyr Leu His Pro Leu Pro Ala
                405                 410                 415
Gly Ala Glu Tyr Cys Ser Ser Ala Arg His Pro Ala Trp Gly His Cys
            420                 425                 430
Phe Tyr Arg Leu Tyr Gln Asp Leu Glu Thr His Arg Leu Pro Cys Thr
        435                 440                 445
Ser Arg Cys Pro Arg Pro Cys Arg Glu Ser Ala Phe Lys Leu Ser Thr
450                 455                 460
Gly Thr Ser Arg Trp Pro Ser Ala Lys Ser Ala Gly Trp Thr Leu Ala
465                 470                 475                 480
Thr Leu Gly Glu Gln Gly Leu Pro His Gln Ser His Arg Gln Arg Ser
                485                 490                 495
Ser Leu Ala Lys Ile Asn Ile Val Tyr Gln Glu Leu Asn Tyr Arg Ser
            500                 505                 510
Val Glu Glu Ala Pro Val Tyr Ser Val Pro Gln Leu Leu Ser Ala Met
        515                 520                 525
Gly Ser Leu Cys Ser Leu Trp Phe Gly Ala Ser Val Leu Ser Leu Leu
530                 535                 540
Glu Leu Leu Glu Leu Leu Leu Asp Ala Ser Ala Leu Thr Leu Val Leu
545                 550                 555                 560
Gly Gly Arg Arg Leu Arg Arg Ala Trp Phe Ser Trp Pro Arg Ala Ser
                565                 570                 575
Pro Ala Ser Gly Ala Ser Ser Ile Lys Pro Glu Ala Ser Gln Met Pro
            580                 585                 590
Pro Pro Ala Gly Gly Thr Ser Asp Asp Pro Glu Pro Ser Gly Pro His
        595                 600                 605
Leu Pro Arg Val Met Leu Pro Gly Val Leu Ala Gly Val Ser Ala Glu
610                 615                 620
Glu Ser Trp Ala Gly Pro Gln Pro Leu Glu Thr Leu Asp Thr
```

<210> SEQ ID NO 25
<211> LENGTH: 638
<212> TYPE: PRT
<213> ORGANISM: Homo Sapiens

<400> SEQUENCE: 25

Met Ala Glu His Arg Ser Met Asp Gly Arg Met Glu Ala Ala Thr Arg
1               5                   10                  15

Gly Gly Ser His Leu Gln Ala Ala Gln Thr Pro Arg Pro Gly
            20                  25                  30

Pro Pro Ser Ala Pro Pro Pro Lys Glu Gly His Gln Glu Gly
        35                  40                  45

Leu Val Glu Leu Pro Ala Ser Phe Arg Glu Leu Thr Phe Phe Cys
    50                  55                      60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
            100                 105                 110

Arg Pro Val Leu Met Ala Val Ser Val His Ser Glu Arg Lys Leu Leu
            115                 120                 125

Pro Leu Val Thr Leu Cys Asp Gly Asn Pro Arg Arg Pro Ser Pro Val
    130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
    195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Phe His His Pro Thr Tyr Gly Ser Cys Tyr Thr
    275                 280                 285

Val Asp Gly Val Trp Thr Ala Gln Arg Pro Gly Ile Thr His Gly Val
    290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Ser Ile Arg Glu Asp Glu Val His Arg Leu Gly Ser Pro Tyr Gly
    355                 360                 365

His Cys Thr Ala Gly Gly Glu Gly Val Glu Val Glu Leu Leu His Asn
    370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Gly Ser Ala Arg His Pro Ala Trp Gly His Cys
            420                 425                 430

Phe Tyr Arg Leu Tyr Gln Asp Leu Glu Thr His Arg Leu Pro Cys Thr
        435                 440                 445

Ser Arg Cys Pro Arg Pro Cys Arg Glu Ser Ala Phe Lys Leu Ser Thr
    450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
            500                 505                 510

Val Glu Glu Ala Pro Val Tyr Ser Val Pro Gln Leu Leu Ser Ala Met
        515                 520                 525

Gly Ser Leu Cys Ser Leu Trp Phe Gly Ala Ser Val Leu Ser Leu Leu
    530                 535                 540

Glu Leu Leu Glu Leu Leu Leu Asp Ala Ser Ala Leu Thr Leu Val Leu
545                 550                 555                 560

Gly Gly Arg Arg Leu Arg Arg Ala Trp Phe Ser Trp Pro Arg Ala Ser
                565                 570                 575

Pro Ala Ser Gly Ala Ser Ser Ile Lys Pro Glu Ala Ser Gln Met Pro
            580                 585                 590

Pro Pro Ala Gly Gly Thr Ser Asp Asp Pro Glu Pro Ser Gly Pro His
        595                 600                 605

Leu Pro Arg Val Met Leu Pro Gly Val Leu Gly Val Ser Ala Glu
    610                 615                 620

Glu Ser Trp Ala Gly Pro Gln Pro Leu Glu Thr Leu Asp Thr
625                 630                 635

<210> SEQ ID NO 26
<211> LENGTH: 638
<212> TYPE: PRT
<213> ORGANISM: Homo Sapiens

<400> SEQUENCE: 26

Met Ala Glu His Arg Ser Met Asp Gly Arg Met Glu Ala Ala Thr Arg
1               5                   10                  15

Gly Gly Ser His Leu Gln Ala Ala Gln Thr Pro Arg Pro Gly
            20                  25                  30

Pro Pro Ser Ala Pro Pro Pro Lys Glu Gly His Gln Glu Gly
        35                  40                  45

Leu Val Glu Leu Pro Ala Ser Phe Arg Glu Leu Leu Thr Phe Phe Cys
    50                  55                  60

Thr Asn Ala Thr Ile His Gly Ala Ile Arg Leu Val Cys Ser Arg Gly
65                  70                  75                  80

Asn Arg Leu Lys Thr Thr Ser Trp Gly Leu Leu Ser Leu Gly Ala Leu
                85                  90                  95

Val Ala Leu Cys Trp Gln Leu Gly Leu Leu Phe Glu Arg His Trp His
            100                 105                 110

-continued

Arg Pro Val Leu Met Ala Val Ser Val His Ser Glu Arg Lys Leu Leu
            115                 120                 125

Pro Leu Val Thr Leu Cys Asp Gly Asn Pro Arg Arg Pro Ser Pro Val
        130                 135                 140

Leu Arg His Leu Glu Leu Leu Asp Glu Phe Ala Arg Glu Asn Ile Asp
145                 150                 155                 160

Ser Leu Tyr Asn Val Asn Leu Ser Lys Gly Arg Ala Ala Leu Ser Ala
                165                 170                 175

Thr Val Pro Arg His Glu Pro Pro Phe His Leu Asp Arg Glu Ile Arg
            180                 185                 190

Leu Gln Arg Leu Ser His Ser Gly Ser Arg Val Arg Val Gly Phe Arg
        195                 200                 205

Leu Cys Asn Ser Thr Gly Gly Asp Cys Phe Tyr Arg Gly Tyr Thr Ser
210                 215                 220

Gly Val Ala Ala Val Gln Asp Trp Tyr His Phe His Tyr Val Asp Ile
225                 230                 235                 240

Leu Ala Leu Leu Pro Ala Ala Trp Glu Asp Ser His Gly Ser Gln Asp
                245                 250                 255

Gly His Phe Val Leu Ser Cys Ser Tyr Asp Gly Leu Asp Cys Gln Ala
            260                 265                 270

Arg Gln Phe Arg Thr Ile His His Pro Thr Tyr Gly Ser Cys Tyr Thr
        275                 280                 285

Val Asp Gly Val Trp Thr Ala Gln Arg Pro Gly Ile Thr His Gly Val
            290                 295                 300

Gly Leu Val Leu Arg Val Glu Gln Gln Pro His Leu Pro Leu Leu Ser
305                 310                 315                 320

Thr Leu Ala Gly Ile Arg Val Met Val His Gly Arg Asn His Thr Pro
                325                 330                 335

Phe Leu Gly His His Ser Phe Ser Val Arg Pro Gly Thr Glu Ala Thr
            340                 345                 350

Ile Arg Ile Arg Glu Asp Glu Val His Arg Leu Gly Ser Pro Tyr Gly
        355                 360                 365

His Cys Thr Ala Gly Gly Glu Gly Val Glu Val Glu Leu Leu His Asn
370                 375                 380

Thr Ser Tyr Thr Arg Gln Ala Cys Leu Val Ser Cys Phe Gln Gln Leu
385                 390                 395                 400

Met Val Glu Thr Cys Ser Cys Gly Tyr Tyr Leu His Pro Leu Pro Ala
                405                 410                 415

Gly Ala Glu Tyr Cys Ser Ser Ala Arg His Pro Ala Trp Gly His Cys
            420                 425                 430

Phe Tyr Arg Leu Tyr Gln Asp Leu Glu Thr His Arg Leu Pro Cys Thr
        435                 440                 445

Ser Arg Cys Pro Arg Pro Cys Arg Glu Ser Ala Phe Lys Leu Ser Thr
450                 455                 460

Gly Thr Ser Arg Trp Pro Ser Ala Lys Ser Ala Gly Trp Thr Leu Ala
465                 470                 475                 480

Thr Leu Gly Glu Gln Gly Leu Pro His Gln Ser His Arg Gln Arg Ser
                485                 490                 495

Ser Leu Ala Lys Ile Asn Ile Val Tyr Gln Glu Leu Asn Tyr Arg Ser
            500                 505                 510

Val Glu Glu Ala Pro Val Tyr Ser Val Pro Gln Leu Leu Ser Ala Met
        515                 520                 525

```
Gly Ser Leu Cys Ser Leu Trp Phe Gly Ala Ser Val Leu Ser Leu Leu
            530                 535                 540

Glu Leu Leu Glu Leu Leu Leu Asp Ala Ser Ala Leu Thr Leu Val Leu
545                 550                 555                 560

Gly Gly Arg Arg Leu His Arg Ala Trp Phe Ser Trp Pro Arg Ala Ser
                565                 570                 575

Pro Ala Ser Gly Ala Ser Ser Ile Lys Pro Glu Ala Ser Gln Met Pro
                580                 585                 590

Pro Pro Ala Gly Gly Thr Ser Asp Asp Pro Glu Pro Ser Gly Pro His
                595                 600                 605

Leu Pro Arg Val Met Leu Pro Gly Val Leu Ala Gly Val Ser Ala Glu
610                 615                 620

Glu Ser Trp Ala Gly Pro Gln Pro Leu Glu Thr Leu Asp Thr
625                 630                 635

<210> SEQ ID NO 27
<211> LENGTH: 649
<212> TYPE: PRT
<213> ORGANISM: Homo Sapiens

<400> SEQUENCE: 27

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
                20                  25                  30

Cys Leu Asn Thr Asn Thr His Gly Cys Arg Arg Ile Val Val Ser Arg
            35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
                100                 105                 110

Leu Leu Ala Asp Leu Glu Gln Glu Thr Arg Glu Ala Leu Lys Ser Leu
            115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
                180                 185                 190

Val Met His Ile Glu Ser Lys Gln Val Val Gly Phe Gln Leu Cys Ser
            195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
                260                 265                 270
```

```
Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
        290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 28
<211> LENGTH: 649
<212> TYPE: PRT
<213> ORGANISM: Homo Sapiens
```

<400> SEQUENCE: 28

```
Met Ala Pro Gly Glu Lys Ile Lys Ala Lys Ile Lys Lys Asn Leu Pro
  1               5                  10                  15
Val Thr Gly Pro Gln Ala Pro Thr Ile Lys Glu Leu Met Arg Trp Tyr
             20                  25                  30
Cys Leu Asn Thr Asn Thr His Gly Cys Arg Arg Ile Val Val Ser Arg
         35                  40                  45
Gly Arg Leu Arg Arg Leu Leu Trp Ile Gly Phe Thr Leu Thr Ala Val
     50                  55                  60
Ala Leu Ile Leu Trp Gln Cys Ala Leu Leu Val Phe Ser Phe Tyr Thr
 65                  70                  75                  80
Val Ser Val Ser Ile Lys Val Asn Phe Arg Lys Leu Asp Phe Pro Ala
                 85                  90                  95
Val Thr Ile Cys Asn Ile Asn Pro Tyr Lys Tyr Ser Thr Val Arg His
            100                 105                 110
Leu Leu Ala Asp Leu Glu Gln Glu Thr Arg Glu Ala Leu Lys Ser Leu
        115                 120                 125
Tyr Gly Phe Pro Glu Ser Arg Lys Arg Arg Glu Ala Glu Ser Trp Asn
    130                 135                 140
Ser Val Ser Glu Gly Lys Gln Pro Arg Phe Ser His Arg Ile Pro Leu
145                 150                 155                 160
Leu Ile Phe Asp Gln Asp Glu Lys Gly Lys Ala Arg Asp Phe Phe Thr
                165                 170                 175
Gly Arg Lys Arg Lys Val Gly Gly Ser Ile Ile His Lys Ala Ser Asn
            180                 185                 190
Val Met His Ile Glu Ser Lys Gln Val Val Gly Phe Gln Leu Cys Ser
        195                 200                 205
Asn Asp Thr Ser Asp Cys Ala Thr Tyr Thr Phe Ser Ser Gly Ile Asn
    210                 215                 220
Ala Ile Gln Glu Trp Tyr Lys Leu His Tyr Met Asn Ile Met Ala Gln
225                 230                 235                 240
Val Pro Leu Glu Lys Lys Ile Asn Met Ser Tyr Ser Ala Glu Glu Leu
                245                 250                 255
Leu Val Thr Cys Phe Phe Asp Gly Val Ser Cys Asp Ala Arg Asn Phe
            260                 265                 270
Thr Leu Phe His His Pro Met His Gly Asn Cys Tyr Thr Phe Asn Asn
        275                 280                 285
Arg Glu Asn Glu Thr Ile Leu Ser Thr Ser Met Gly Gly Ser Glu Tyr
    290                 295                 300
Gly Leu Gln Val Ile Leu Tyr Ile Asn Glu Glu Glu Tyr Asn Pro Phe
305                 310                 315                 320
Leu Val Ser Ser Thr Gly Ala Lys Val Ile Ile His Arg Gln Asp Glu
                325                 330                 335
Tyr Pro Phe Val Glu Asp Val Gly Thr Glu Ile Glu Thr Ala Met Val
            340                 345                 350
Thr Ser Ile Gly Met His Leu Thr Glu Ser Phe Lys Leu Ser Glu Pro
        355                 360                 365
Tyr Ser Gln Cys Thr Glu Asp Gly Ser Asp Val Pro Ile Arg Asn Ile
    370                 375                 380
Tyr Asn Ala Ala Tyr Ser Leu Gln Ile Cys Leu His Ser Cys Phe Gln
385                 390                 395                 400
Thr Lys Met Val Glu Lys Cys Gly Cys Ala Gln Tyr Ser Gln Pro Leu
                405                 410                 415
```

```
Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 29
<211> LENGTH: 649
<212> TYPE: PRT
<213> ORGANISM: Homo Sapiens

<400> SEQUENCE: 29

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
```

-continued

```
            130                 135                 140
Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
                180                 185                 190

Val Met His Ile Glu Ser Lys Gln Val Val Gly Phe Gln Leu Cys Ser
                195                 200                 205

Asn Asp Thr Ser Asp Cys Ala Thr Tyr Thr Phe Ser Ser Gly Ile Asn
210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
                260                 265                 270

Thr Leu Phe His His Pro Met His Gly Asn Cys Tyr Thr Phe Asn Asn
                275                 280                 285

Arg Glu Asn Glu Thr Ile Leu Ser Thr Ser Met Gly Gly Ser Glu Tyr
                290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
                340                 345                 350

Thr Ser Ile Gly Met His Leu Thr Glu Ser Phe Lys Leu Ser Glu Pro
                355                 360                 365

Tyr Ser Gln Cys Thr Glu Asp Gly Ser Asp Val Pro Ile Arg Asn Ile
                370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
                420                 425                 430

Tyr Cys Tyr Tyr Gln Leu His Arg Ala Phe Val Gln Glu Glu Leu Gly
                435                 440                 445

Cys Gln Ser Val Cys Lys Glu Ala Cys Ser Phe Lys Glu Trp Thr Leu
450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
                515                 520                 525

Ser Asn Phe Gly Gly Gln Leu Gly Leu Trp Met Ser Cys Ser Val Val
                530                 535                 540

Cys Val Ile Glu Ile Ile Glu Val Phe Phe Ile Asp Phe Phe Ser Ile
545                 550                 555                 560
```

-continued

```
Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 30
<211> LENGTH: 649
<212> TYPE: PRT
<213> ORGANISM: Homo Sapiens

<400> SEQUENCE: 30

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Glu Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
```

```
                275                 280                 285
Arg Glu Asn Glu Thr Ile Leu Ser Thr Ser Met Gly Gly Ser Glu Tyr
290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile His Arg Gln Asp Glu
                325                 330                 335

Tyr Pro Phe Val Glu Asp Val Gly Thr Glu Ile Glu Thr Ala Met Val
                340                 345                 350

Thr Ser Ile Gly Met His Leu Thr Glu Ser Phe Lys Leu Ser Glu Pro
            355                 360                 365

Tyr Ser Gln Cys Thr Glu Asp Gly Ser Asp Val Pro Ile Arg Asn Ile
370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
                420                 425                 430

Tyr Cys Tyr Tyr Gln Leu His Arg Ala Phe Val Gln Glu Glu Leu Gly
            435                 440                 445

Cys Gln Ser Val Cys Lys Glu Ala Cys Ser Phe Lys Glu Trp Thr Leu
450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
            515                 520                 525

Ser Asn Phe Gly Gly Gln Leu Gly Leu Trp Met Ser Cys Ser Val Val
530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
                580                 585                 590

Asn Pro Ala Leu Asp Ile Asp Asp Leu Pro Thr Phe Asn Ser Ala
            595                 600                 605

Leu His Leu Pro Pro Ala Leu Gly Thr Gln Val Pro Ser Thr Pro Pro
610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 31
<211> LENGTH: 649
<212> TYPE: PRT
<213> ORGANISM: Homo Sapiens

<400> SEQUENCE: 31
```

```
Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
                35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Ala
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
                100                 105                 110

Leu Leu Ala Asp Leu Glu Gln Glu Thr Arg Glu Ala Leu Lys Ser Leu
            115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
            165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
            195                 200                 205

Asn Asp Thr Ser Asp Cys Ala Thr Tyr Thr Phe Ser Ser Gly Ile Asn
210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
            245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
            275                 280                 285

Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
            325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
            355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
            405                 410                 415

Pro Pro Ala Ala Asn Tyr Cys Asn Tyr Gln Gln His Pro Asn Trp Met
```

-continued

```
                420                 425                 430
Tyr Cys Tyr Tyr Gln Leu His Arg Ala Phe Val Gln Glu Glu Leu Gly
            435                 440                 445

Cys Gln Ser Val Cys Lys Glu Ala Cys Ser Phe Lys Glu Trp Thr Leu
        450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Thr Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Ser Leu
625                 630                 635                 640

Thr Asp Thr Gln Met Leu Asp Glu Leu
                645

<210> SEQ ID NO 32
<211> LENGTH: 649
<212> TYPE: PRT
<213> ORGANISM: Homo Sapiens

<400> SEQUENCE: 32

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140
```

-continued

```
Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
        275                 280                 285

Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
            325                 330                 335

Tyr Pro Phe Val Glu Asp Val Gly Thr Glu Ile Glu Thr Ala Met Val
        340                 345                 350

Thr Ser Ile Gly Met His Leu Thr Glu Ser Phe Lys Leu Ser Glu Pro
    355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
```

-continued

```
                565                 570                 575
Gln Ala Pro Pro Cys Pro Glu Ala Pro Arg Ser Pro Gln Gly Gln Asp
            580                 585                 590
Asn Pro Ala Leu Asp Ile Asp Asp Gly Leu Pro Thr Phe Asn Ser Ala
        595                 600                 605
Leu His Leu Pro Pro Ala Leu Gly Thr Gln Val Pro Gly Thr Pro Pro
    610                 615                 620
Pro Lys Tyr Asn Thr Leu Arg Leu Glu Arg Ala Phe Ser Asn Gln Leu
625                 630                 635                 640
Thr Asp Thr Gln Met Leu Asp Glu Leu
                    645

<210> SEQ ID NO 33
<211> LENGTH: 649
<212> TYPE: PRT
<213> ORGANISM: Homo Sapiens

<400> SEQUENCE: 33

Met Ala Pro Gly Glu Lys Ile Lys Ala Lys Ile Lys Lys Asn Leu Pro
1               5                   10                  15
Val Thr Gly Pro Gln Ala Pro Thr Ile Lys Glu Leu Met Arg Trp Tyr
            20                  25                  30
Cys Leu Asn Thr Asn Thr His Gly Cys Arg Arg Ile Val Val Ser Arg
        35                  40                  45
Gly Arg Leu Arg Arg Leu Leu Trp Ile Gly Phe Thr Leu Thr Ala Val
    50                  55                  60
Ala Leu Ile Leu Trp Gln Cys Ala Leu Leu Val Phe Ser Phe Tyr Thr
65                  70                  75                  80
Val Ser Val Ser Ile Lys Val His Phe Arg Lys Leu Asp Phe Pro Ala
                85                  90                  95
Val Thr Ile Cys Asn Ile Asn Pro Tyr Lys Tyr Ser Thr Val Arg His
            100                 105                 110
Leu Leu Ala Asp Leu Glu Gln Glu Thr Arg Glu Ala Leu Lys Ser Leu
        115                 120                 125
Tyr Gly Phe Pro Glu Ser Arg Lys Arg Glu Ala Glu Ser Trp Asn
    130                 135                 140
Ser Val Ser Glu Gly Lys Gln Pro Arg Phe Ser His Arg Ile Pro Pro
145                 150                 155                 160
Leu Ile Phe Asp Gln Asp Glu Lys Gly Lys Ala Arg Asp Phe Phe Thr
                165                 170                 175
Gly Arg Lys Arg Lys Val Gly Gly Ser Ile Ile His Lys Ala Ser Asn
            180                 185                 190
Val Met His Ile Glu Ser Lys Gln Val Val Gly Phe Gln Leu Cys Ser
        195                 200                 205
Asn Asp Thr Ser Asp Cys Ala Thr Tyr Thr Phe Ser Leu Gly Ile Asn
    210                 215                 220
Ala Ile Gln Glu Trp Tyr Lys Leu His Tyr Met Asn Ile Met Ala Gln
225                 230                 235                 240
Val Pro Leu Glu Lys Lys Ile Asn Met Ser Tyr Ser Ala Glu Glu Leu
                245                 250                 255
Leu Val Thr Cys Phe Phe Asp Gly Val Ser Cys Asp Ala Arg Asn Phe
            260                 265                 270
Thr Leu Phe His His Pro Met His Gly Asn Cys Tyr Thr Phe Asn Asn
        275                 280                 285
```

```
Arg Glu Asn Glu Thr Ile Leu Ser Thr Ser Met Gly Gly Ser Glu Tyr
    290                 295                 300

Gly Leu Gln Val Ile Leu Tyr Ile Asn Glu Glu Tyr Asn Pro Phe
305                 310                 315                 320

Leu Val Ser Ser Thr Gly Ala Lys Val Ile Ile His Arg Gln Asp Glu
                325                 330                 335

Tyr Pro Phe Val Glu Asp Val Gly Thr Glu Ile Glu Thr Ala Met Val
            340                 345                 350

Thr Ser Ile Gly Met His Leu Thr Glu Ser Phe Lys Leu Ser Glu Pro
        355                 360                 365

Tyr Ser Gln Cys Thr Glu Asp Gly Ser Asp Val Pro Ile Arg Asn Ile
    370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
            420                 425                 430

Tyr Cys Tyr Tyr Gln Leu His Arg Ala Phe Val Gln Glu Glu Leu Gly
        435                 440                 445

Cys Gln Ser Val Cys Lys Glu Ala Cys Ser Leu Lys Glu Trp Thr Leu
    450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
    530                 535                 540

Cys Val Ile Glu Ile Ile Glu Val Phe Phe Ile Asp Phe Phe Ser Ile
545                 550                 555                 560

Thr Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 34
<211> LENGTH: 649
<212> TYPE: PRT
<213> ORGANISM: Homo Sapiens

<400> SEQUENCE: 34

Met Ala Pro Gly Glu Lys Ile Lys Ala Lys Ile Lys Lys Asn Leu Pro
1               5                   10                  15
```

-continued

```
Val Thr Gly Pro Gln Ala Pro Thr Ile Lys Glu Leu Met Arg Trp Tyr
             20                  25                  30

Cys Leu Asn Thr Asn Thr His Gly Cys Arg Arg Ile Val Val Ser Arg
             35                  40                  45

Gly Arg Leu Arg Arg Leu Leu Trp Ile Gly Phe Thr Leu Thr Ala Val
             50                  55                  60

Ala Leu Ile Leu Trp Gln Cys Ala Leu Leu Val Phe Ser Phe Tyr Thr
 65                  70                  75                  80

Val Ser Val Ser Ile Lys Val His Phe Arg Lys Leu Asp Phe Pro Ala
                     85                  90                  95

Val Thr Ile Cys Asn Ile Asn Pro Tyr Lys Tyr Ser Thr Val Arg His
                 100                 105                 110

Leu Leu Ala Asp Leu Glu Gln Glu Thr Arg Glu Ala Leu Lys Ser Leu
                 115                 120                 125

Tyr Gly Phe Pro Glu Ser Arg Lys Arg Arg Glu Ala Glu Ser Trp Asn
             130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                 165                 170                 175

Gly Arg Lys Arg Lys Val Gly Gly Ser Ile Ile His Lys Ala Ser Asn
             180                 185                 190

Val Met His Ile Glu Ser Lys Gln Val Val Gly Phe Gln Leu Cys Ser
             195                 200                 205

Asn Asp Thr Ser Asp Cys Ala Thr Tyr Thr Phe Ser Ser Gly Ile Asn
             210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                 245                 250                 255

Leu Val Thr Cys Phe Phe Asp Gly Val Ser Cys Asp Ala Arg Asn Phe
             260                 265                 270

Thr Leu Phe His His Pro Met His Gly Asn Cys Tyr Thr Phe Asn Asn
             275                 280                 285

Arg Glu Asn Glu Thr Ile Leu Ser Thr Ser Met Gly Gly Ser Glu Tyr
             290                 295                 300

Gly Leu Gln Val Ile Leu Tyr Ile Asn Glu Glu Glu Tyr Asn Pro Phe
305                 310                 315                 320

Leu Val Ser Ser Thr Gly Ala Lys Val Ile Ile His Arg Gln Asp Glu
                 325                 330                 335

Tyr Pro Phe Val Glu Asp Val Gly Thr Glu Ile Glu Thr Ala Met Val
             340                 345                 350

Thr Ser Ile Gly Met His Leu Thr Glu Ser Phe Lys Leu Ser Glu Pro
             355                 360                 365

Tyr Ser Gln Cys Thr Glu Asp Gly Ser Asp Val Pro Ile Arg Asn Ile
             370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                 405                 410                 415

Pro Pro Ala Ala Asn Tyr Cys Asn Tyr Gln Gln His Pro Asn Trp Met
             420                 425                 430
```

Tyr Cys Tyr Tyr Gln Leu His Arg Ala Phe Val Gln Glu Glu Leu Gly
        435                 440                 445

Cys Gln Ser Val Cys Lys Glu Ala Cys Ser Phe Lys Glu Trp Thr Leu
        450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
            500                 505                 510

Gln Arg Ser Ile Met Glu Ser Pro Ala Asn Ser Ile Glu Met Leu Leu
        515                 520                 525

Ser Asn Phe Gly Gly Gln Leu Gly Leu Trp Met Ser Cys Ser Val Val
        530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
        595                 600                 605

Leu His Leu Pro Pro Ala Leu Gly Thr Gln Val Pro Gly Thr Pro Pro
        610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 35
<211> LENGTH: 649
<212> TYPE: PRT
<213> ORGANISM: Homo Sapiens

<400> SEQUENCE: 35

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Trp Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

-continued

```
Leu Ile Phe Asp Gln Asp Glu Lys Gly Lys Ala Arg Asp Phe Phe Thr
                165                 170                 175
Gly Arg Lys Arg Lys Val Gly Gly Ser Ile Ile His Lys Ala Ser Asn
            180                 185                 190
Val Met His Ile Glu Ser Lys Gln Val Val Gly Phe Gln Leu Cys Ser
        195                 200                 205
Asn Asp Thr Ser Asp Cys Ala Thr Tyr Thr Phe Ser Ser Gly Ile Asn
    210                 215                 220
Ala Ile Gln Glu Trp Tyr Lys Leu His Tyr Met Asn Ile Met Ala Gln
225                 230                 235                 240
Val Pro Leu Glu Lys Lys Ile Asn Met Ser Tyr Ser Ala Glu Glu Leu
                245                 250                 255
Leu Val Thr Cys Phe Phe Asp Gly Val Ser Cys Asp Ala Arg Asn Phe
            260                 265                 270
Thr Leu Phe His His Pro Met His Gly Asn Cys Tyr Thr Phe Asn Asn
        275                 280                 285
Arg Glu Asn Glu Thr Ile Leu Ser Thr Ser Met Gly Gly Ser Glu Tyr
    290                 295                 300
Gly Leu Gln Val Ile Leu Tyr Ile Asn Glu Glu Tyr Asn Pro Phe
305                 310                 315                 320
Leu Val Ser Ser Thr Gly Ala Lys Val Ile His Arg Gln Asp Glu
                325                 330                 335
Tyr Pro Phe Val Glu Asp Val Gly Thr Glu Ile Glu Thr Ala Met Val
            340                 345                 350
Thr Ser Ile Gly Met His Leu Thr Glu Ser Phe Lys Leu Ser Glu Pro
        355                 360                 365
Tyr Ser Gln Cys Thr Glu Asp Gly Ser Asp Val Pro Ile Arg Asn Ile
    370                 375                 380
Tyr Asn Ala Ala Tyr Ser Leu Gln Ile Cys Leu His Ser Cys Phe Gln
385                 390                 395                 400
Thr Lys Met Val Glu Lys Cys Gly Cys Ala Gln Tyr Ser Gln Pro Leu
                405                 410                 415
Pro Pro Ala Ala Asn Tyr Cys Asn Tyr Gln Gln His Pro Asn Trp Met
            420                 425                 430
Tyr Cys Tyr Tyr Gln Leu His Arg Ala Phe Val Gln Glu Glu Leu Gly
        435                 440                 445
Cys Gln Ser Val Cys Lys Glu Ala Cys Ser Phe Lys Glu Trp Thr Leu
    450                 455                 460
Thr Thr Ser Leu Ala Gln Trp Pro Ser Val Val Ser Glu Lys Trp Leu
465                 470                 475                 480
Leu Pro Val Leu Thr Trp Asp Gln Gly Arg Gln Val Asn Lys Lys Leu
                485                 490                 495
Asn Lys Thr Asp Leu Ala Lys Leu Leu Ile Phe Tyr Lys Asp Leu Asn
            500                 505                 510
Gln Arg Ser Ile Met Glu Ser Pro Ala Asn Ser Ile Glu Met Leu Leu
        515                 520                 525
Ser Asn Phe Gly Gly Gln Leu Gly Leu Trp Met Ser Cys Ser Val Val
    530                 535                 540
Cys Val Ile Glu Ile Ile Glu Val Phe Phe Ile Asp Phe Phe Ser Ile
545                 550                 555                 560
Ile Ala Arg Arg Gln Trp Gln Lys Ala Lys Glu Trp Trp Ala Trp Lys
                565                 570                 575
```

```
Gln Ala Pro Pro Cys Pro Glu Ala Pro Arg Ser Pro Gln Gly Gln Asp
            580                 585                 590

Asn Pro Ala Leu Asp Ile Asp Asp Leu Pro Thr Phe Asn Ser Ala
            595                 600                 605

Leu His Leu Pro Pro Ala Leu Gly Thr Gln Val Pro Gly Thr Pro Pro
    610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645

<210> SEQ ID NO 36
<211> LENGTH: 649
<212> TYPE: PRT
<213> ORGANISM: Homo Sapiens

<400> SEQUENCE: 36

Met Ala Pro Gly Glu Lys Ile Lys Ala Lys Ile Lys Lys Asn Leu Pro
1               5                   10                  15

Val Thr Gly Pro Gln Ala Pro Thr Ile Lys Glu Leu Met Arg Trp Tyr
            20                  25                  30

Cys Leu Asn Thr Asn Thr His Gly Cys Arg Arg Ile Val Val Ser Arg
        35                  40                  45

Gly Arg Leu Arg Arg Leu Leu Trp Ile Gly Phe Thr Leu Thr Ala Val
    50                  55                  60

Ala Leu Ile Leu Arg Gln Cys Ala Leu Leu Val Phe Ser Phe Tyr Thr
65                  70                  75                  80

Val Ser Val Ser Ile Lys Val His Phe Arg Lys Leu Asp Phe Pro Ala
                85                  90                  95

Val Thr Ile Cys Asn Ile Asn Pro Tyr Lys Tyr Ser Thr Val Arg His
            100                 105                 110

Leu Leu Ala Asp Leu Glu Gln Glu Thr Arg Glu Ala Leu Lys Ser Leu
        115                 120                 125

Tyr Gly Phe Pro Glu Ser Arg Lys Arg Arg Glu Ala Glu Ser Trp Asn
    130                 135                 140

Ser Val Ser Glu Gly Lys Gln Pro Arg Phe Ser His Arg Ile Pro Leu
145                 150                 155                 160

Leu Ile Phe Asp Gln Asp Glu Lys Gly Lys Ala Arg Asp Phe Phe Thr
                165                 170                 175

Gly Arg Lys Arg Lys Val Gly Gly Ser Ile Ile His Lys Ala Ser Asn
            180                 185                 190

Val Met His Ile Glu Ser Lys Gln Val Val Gly Phe Gln Leu Cys Ser
        195                 200                 205

Asn Asp Thr Ser Asp Cys Ala Thr Tyr Thr Phe Ser Ser Gly Ile Asn
    210                 215                 220

Ala Ile Gln Glu Trp Tyr Lys Leu His Tyr Met Asn Ile Met Ala Gln
225                 230                 235                 240

Val Pro Leu Glu Lys Lys Ile Asn Met Ser Tyr Ser Ala Glu Glu Leu
                245                 250                 255

Leu Val Thr Cys Phe Phe Asp Gly Val Ser Cys Asp Ala Arg Asn Phe
            260                 265                 270

Thr Leu Phe His His Pro Met His Gly Asn Cys Tyr Thr Phe Asn Asn
        275                 280                 285

Arg Glu Asn Glu Thr Ile Leu Ser Thr Ser Met Gly Gly Ser Glu Tyr
    290                 295                 300
```

```
Gly Leu Gln Val Ile Leu Tyr Ile Asn Glu Glu Tyr Asn Pro Phe
305                 310                 315                 320

Leu Val Ser Ser Thr Gly Ala Lys Val Ile His Arg Gln Asp Glu
            325                 330                 335

Tyr Pro Phe Val Glu Asp Val Gly Thr Glu Ile Glu Thr Ala Met Val
                340                 345                 350

Thr Ser Ile Gly Met His Leu Thr Glu Ser Phe Lys Leu Ser Glu Pro
                355                 360                 365

Tyr Ser Gln Cys Thr Glu Asp Gly Ser Asp Val Pro Ile Arg Asn Ile
                370                 375                 380

Tyr Asn Ala Ala Tyr Ser Leu Gln Ile Cys Leu His Ser Cys Phe Gln
385                 390                 395                 400

Thr Lys Met Val Glu Lys Cys Gly Cys Ala Gln Tyr Ser Gln Pro Leu
                405                 410                 415

Pro Pro Ala Ala Asn Tyr Cys Asn Tyr Gln Gln His Pro Asn Trp Met
                420                 425                 430

Tyr Cys Tyr Tyr Gln Leu His Arg Ala Phe Val Gln Glu Glu Leu Gly
                435                 440                 445

Cys Gln Ser Val Cys Lys Glu Ala Cys Ser Phe Lys Glu Trp Thr Leu
                450                 455                 460

Thr Thr Ser Leu Ala Gln Trp Pro Ser Val Val Ser Glu Lys Trp Leu
465                 470                 475                 480

Leu Pro Val Leu Thr Trp Asp Gln Gly Arg Gln Val Asn Lys Lys Leu
                485                 490                 495

Asn Lys Thr Asp Leu Ala Lys Leu Leu Ile Phe Tyr Lys Asp Leu Asn
                500                 505                 510

Gln Arg Ser Ile Met Glu Ser Pro Ala Asn Ser Ile Glu Met Leu Leu
                515                 520                 525

Ser Asn Phe Gly Gly Gln Leu Gly Leu Trp Met Ser Cys Ser Val Val
                530                 535                 540

Cys Val Ile Glu Ile Ile Glu Val Phe Phe Ile Asp Phe Phe Ser Ile
545                 550                 555                 560

Ile Ala Arg Arg Gln Trp Gln Lys Ala Lys Glu Trp Trp Ala Trp Lys
                565                 570                 575

Gln Ala Pro Pro Cys Pro Glu Ala Pro Arg Ser Pro Gln Gly Gln Asp
                580                 585                 590

Asn Pro Ala Leu Asp Ile Asp Asp Leu Pro Thr Phe Asn Ser Ala
                595                 600                 605

Leu His Leu Pro Pro Ala Leu Gly Thr Gln Val Pro Gly Thr Pro Pro
                610                 615                 620

Pro Lys Tyr Asn Thr Leu Arg Leu Glu Arg Ala Phe Ser Asn Gln Leu
625                 630                 635                 640

Thr Asp Thr Gln Met Leu Asp Glu Leu
                645
```

HUMAN SALTY TASTE RECEPTOR AND METHODS OF MODULATING SALTY TASTE PERCEPTION

CROSS-REFERENCE TO RELATED APPLICATIONS

This application claims benefit to U.S. Provisional Application No. 60/853,290 filed Oct. 19, 2006, the entire contents of which are incorporated by reference herein, in their entirety and for all purposes.

FIELD

The invention relates generally to the field of cell biology. More specifically, the invention relates to sodium ion channels and their role in the recognition of salty taste in humans.

BACKGROUND

Various publications, including patents, published applications, technical articles and scholarly articles are cited throughout the specification. Each of these cited publications is incorporated by reference herein, in its entirety and for all purposes.

Sodium plays an important role in the body's metabolism, including, among other things, electrical impulse transmission and fluid and electrolyte homeostasis. In addition, sodium contributes to the development and stability of flavor in the various foods ingested by animals, particularly by humans. The sodium ion can inhibit the bitter taste of some stimuli, thereby modifying the taste of food. This inhibitory effect of sodium on bitter taste does not depend on the saltiness of the compound containing the sodium ion, but rather depends on the concentration of the sodium ion.

Excess intake of sodium, however, has been implicated in various disease states, including gastric cancer and hypertension. Hypertension is a major risk factor for heart disease, stroke, and kidney disease. Because of the potential negative health effects of excess sodium consumption, the United States FDA recommends that adults limit their intake to less than 2400 milligrams of sodium per day. Nevertheless, Americans generally far exceed this recommended allowance. As such, various medical and scientific groups have recommended drastic reductions in sodium intake.

To further the goal of reduced sodium intake, numerous salty taste mimics and salty taste enhancers have been developed. In general, such mimics have not proven commercially viable as they lack the clean saltiness of sodium chloride, and most do not affect food flavor as sodium salt does.

The dearth of mimics of salty taste, commonly known as salt substitutes, reflects the extreme structural specificity of the taste receptor. As far is known, only sodium chloride (NaCl) and lithium chloride (LiCl) impart a true salty taste. Both heavier anions paired with Na and Li, and heavier cations paired with Cl tend to be bitter. The cation specificity suggests an ion channel, while the chloride effects suggests paracellular shunts. In addition, the concentration at which NaCl imparts a salty taste is above 50 mM, a concentration on the higher end of receptor processes. These two observations—the specificity for Na and Li, and the effective concentration range—are believed to be the key to discovering the mechanism of salty taste in humans.

Over the past two decades, numerous studies, both qualitative and quantitative, of salt-induced changes in neural activity in the presence or absence of specific inhibitors and enhancers have led to the supposition that an epithelial sodium channel (ENaC) acts as the primary receptor for saltiness (Brand et al. (1985) *Brain Res.* 334:207-14; Feigin et al. (1994) *Am. J. Physiol.* 266 (Cell Physiol):C1165-72; and, Brelin et al. (2006) *Adv. Otorhinolaryngol.* 63:152-90). While the ENaC serves as the salt receptor for many experimental animals (Halpern, B P (1998) *Neurosci. Biobehav. Rev.* 23(1):5-47), no conclusive evidence has emerged that the same holds true for human beings. Notably, the inability of amiloride to inhibit sodium-induced salty taste response in humans suggests that ENaCs are not involved in human salty taste recognition, at least to the extent observed in other animals.

Because of this discrepancy between human and animal models, the transduction mechanisms underlying the perception of salty taste in humans remain under investigation. Sufficient activation of the nerve eventually evokes the sensation of saltiness in the higher cortical areas (Schoenfeld, M A et al. (2004) *Neuroscience.* 127:347-53).

Because of the robust response shown to amiloride by taste cells of many rodents, the ENaCs in these cells are assumed to be located primarily at the apical membrane, above the level of the tight junctions. This location makes them susceptible to the action of drugs such as amiloride. It is assumed that amiloride cannot pass the tight junctions. Augmenting the direct mechanism at the apical membrane is a paracellular shunt pathway into the basolateral area of taste buds below the tight junction level (Mierson, S et al. (1996) *J. Neurophysiol.* 76:1297-309). Since sodium can pass the tight junctions, the paracellular mechanism should result in an amiloride insensitive salty taste response. The human salty response may be amiloride-insensitive because the vast majority of taste cell ENaCs are located below these tight junctions. Other mechanisms for salt perception may exist. These could be entirely different from the ENaC, or an alternative manifestation of the ENaC due to sodium load or hormonal influences on ENaC expression or composition.

ENaCs comprise a family of cation channel proteins mediating sodium permeation in epithelia (Mano, I et al. (1999) *Bioessays* 21:568-78). Expression cloning originally demonstrated that there are three homologous genes, each encoding one of the three subunits of the channel—i.e., alpha ($\alpha$), beta ($\beta$) and gamma ($\gamma$) (Canessa, C M et al. (1994) *Nature* 367:463-7). Co-expression of all three subunits is essential for maximal Na+ channel activity, although the alpha subunit by itself produces a small current. A fourth subunit, delta ($\delta$) was later cloned and shown to be similar to the alpha subunit both structurally and functionally, albeit with a 30-fold lower affinity for amiloride (Waldmann et al. (1995) *J. Biol. Chem.* 270:27411-4). This lower amiloride sensitivity is assumed to be reflected in a motif called the PreMR2 sequence. The transmembrane topology of the ENaCs comprises two hydrophobic transmembrane domains flanking a long extracellular loop, with intracellular amino and carboxyl termini. The subunit stoichiometry of the ENaCs may be species-specific and tissue-specific, since there is evidence for an $\alpha 2\beta\gamma$ configuration in rats (Firsov et al. (1998) *EMBO J.* 17:344-52) and an $(\alpha)1\beta(1)\gamma(1)$ arrangement in humans (Staruschenko, A (2005) *Biophys. J.* 88:3966-75).

For improved health and wellness, there is a need to diminish sodium intake. This need must be balanced with the desire for the taste of sodium, and the ability of sodium to impart improved flavor in food. One attractive means to diminish dietary sodium without sacrificing sodium flavor is to use modulators of salty taste. Thus, there is a need to establish the definitive receptor for salty taste perception and for a means to identify modulators of salty taste perception.

SUMMARY

The invention provides an isolated human salty taste receptor comprising at least one beta polypeptide subunit, at least one gamma polypeptide subunit, and at least one delta polypeptide subunit wherein said delta polypeptide subunit comprises the amino acid sequence of SEQ ID NO:12. In some aspects, the delta polypeptide subunit has the amino acid sequence of SEQ ID NO:9. Also provided is an isolated human salty taste receptors comprising at least one alpha polypeptide subunit, at least one beta polypeptide subunit, at least one delta polypeptide subunit, and at least one gamma polypeptide subunit.

The invention also provides a method for identifying modulators of epithelial sodium ion channels. Such methods include assembling at least one epithelial sodium ion channel in a lipid membrane (wherein the epithelial sodium ion channel comprises at least three types of subunits, which are independently an alpha subunit, a beta subunit, a gamma subunit, a delta subunit, and an epsilon subunit); contacting the ion channel with a test compound in the presence of sodium ions or lithium ions; and determining a modulation of the biological activity of the epithelial sodium ion channel in the presence of the test compound relative to the biological activity of the epithelial sodium ion channel in the absence of the test compound. The lipid membrane is preferably an artificial membrane.

In some aspects, the epithelial ion channel comprises one alpha subunit, one beta subunit, and one gamma subunit. In other aspects, the epithelial ion channel comprises one alpha subunit, one beta subunit, one gamma subunit, and one epsilon subunit. In other aspects, the epithelial ion channel comprises two alpha subunits, one beta subunit, and one gamma subunit. In further aspects the epithelial ion channel comprises three alpha subunits, three beta subunits, and three gamma subunits. Additional aspects include those wherein the epithelial ion channel comprises one delta subunit, one beta subunit, and one gamma subunit. In other aspects, the epithelial ion channel comprises two delta subunits, one beta subunit, and one gamma subunit. In still further aspects, the epithelial ion channel comprises two delta subunits, two beta subunits, and two gamma subunits. In still further aspects, the epithelial ion channel comprises three delta subunits, three beta subunits, and three gamma subunits.

In the method for identifying modulators of epithelial sodium channels, the method may further include contacting the epithelial sodium ion channel with an epithelial sodium ion channel antagonist, such as, but not limited to chlorhexidine, amiloride, phenamil, benzamil or a homolog, analog, or derivative thereof.

In the method for identifying modulators of epithelial sodium channels, suitable lipid components for the membrane include at least one of phosphatidylcholine, phoshpatidylethanolamine, phostphatidylserine, phosphatidylglyine, phosphatidylinositol, sphingomyelin, cholesterol, cardiolipin, or a homolog, analog, or derivative thereof. As such the lipids may be organized as a micelle, liposome, or lipid bilayer.

In some aspects of the method for identifying modulators of epithelial sodium channels, at least two subunits of an epithelial sodium ion channel are present in the lipid membrane at differing ratios relative to each other.

In the step for determining a modulation of the biological activity of the epithelial sodium ion channel, any suitable means known in the art may be used, such as, but not limited to, voltage clamping, and/or measurement of an indicator dye. The method may be adapted for high throughput screening.

The method for identifying modulators of epithelial sodium channels thus provides compounds identified by the method that act as modulators of the epithelial sodium channels. These compounds may be formulated into compositions by admixing the compounds with a pharmaceutically acceptable carrier.

In a specific aspect, the invention provides a method for identifying modulators of the human salty taste receptor comprising: assembling at least one salty taste receptor in a lipid membrane, wherein the salty taste receptor comprises at least one beta subunit, at least one gamma subunit, and at least one delta subunit; contacting the ion channel with a test compound in the presence of sodium ions or lithium ions; and determining a modulation of the biological activity of the salty taste receptor in the presence of the test compound relative to the biological activity of the salty taste receptor in the absence of the test compound.

In some aspects, the human salty taste receptor comprises one alpha subunit, one beta subunit, and one gamma subunit. In other aspects, the salty taste receptor comprises one alpha subunit, one beta subunit, one gamma subunit, and one epsilon subunit. In other aspects, the salty taste receptor comprises two alpha subunits, one beta subunit, and one gamma subunit. In further aspects the salty taste receptor comprises three alpha subunits, three beta subunits, and three gamma subunits. Additional aspects include those wherein the salty taste receptor comprises one delta subunit, one beta subunit, and one gamma subunit. In other aspects, the salty taste receptor comprises two delta subunits, one beta subunit, and one gamma subunit. In still further aspects, the salty taste receptor comprises two delta subunits, two beta subunits, and two gamma subunits. In still further aspects, the salty taste receptor comprises three delta subunits, three beta subunits, and three gamma subunits.

In the method for identifying modulators of the human salty taste receptor, the delta subunit preferably comprises the amino acid sequence of SEQ ID NO:12. In some aspects, the delta receptor comprises the amino acid sequence of SEQ ID NO:9. In the method for identifying modulators of the human salty taste receptor, the method may further comprise contacting the epithelial sodium ion channel with an epithelial sodium ion channel antagonist, such as, but not limited to, chlorhexidine, amiloride, phenamil, benzamil or a homolog, analog, or derivative thereof.

In the method for identifying modulators of the human salty taste receptor, the lipid membrane may comprise at least one of phosphatidylcholine, phoshpatidylethanolamine, phostphatidylserine, phosphatidylglyine, phosphatidylinositol, sphingomyelin, cholesterol, cardiolipin, or a homolog, analog, or derivative thereof. The lipids may be organized as a liposome or lipid bilayer.

In some aspects of the method for identifying modulators of the human salty taste receptor, at least two subunits of an epithelial sodium ion channel are present in the lipid membrane at differing ratios relative to each other. The channels in the membrane preferably comprise at least one biological activity of a functional human salty taste receptor.

In the step for determining a modulation of the biological activity of the salty taste receptor, any suitable means known in the art may be used, such as, but not limited to voltage clamping, and/or measurement of an indicator dye. The method may be adapted for high throughput screening.

Compounds that modulate human salty taste perception are identified by the method of the invention and may include, for example, salty taste mimics, enhancers, modifiers, and inhibitors. The invention thus provides modulators of human salty taste perception which may further be used in compositions by admixing the compounds with a pharmaceutically acceptable carrier, or foods and beverages to modulate the salty taste perception of the food or beverage.

The invention also provides an artificial lipid membrane comprising at least one type of phospholipid and an epithelial sodium ion channel or specific ratios of epithelial sodium ion channel subunits wherein the subunits are selected from the group consisting of alpha subunits, beta subunits, gamma subunits, delta subunits, and epsilon subunits.

The artificial lipid membrane may comprise at least one phospholipid including phosphatidylcholine, phoshpatidylethanolamine, phostphatidylserine, phosphatidylglyine, phosphatidylinositol, sphingomyelin, cholesterol, cardiolipin, or a homolog, analog, or derivative thereof. The lipid membrane may be organized, for example, as a liposome or lipid bilayer.

In some aspects, the artificial lipid membrane comprises at least one epithelial ion channel comprising one alpha subunit, one beta subunit, and one gamma subunit. In other aspects, the epithelial ion channel comprises one alpha subunit, one beta subunit, one gamma subunit, and one epsilon subunit. In other aspects, the epithelial ion channel comprises two alpha subunits, one beta subunit, and one gamma subunit. In further aspects the epithelial ion channel comprises three alpha subunits, three beta subunits, and three gamma subunits. Additional aspects include those wherein the epithelial ion channel comprises one delta subunit, one beta subunit, and one gamma subunit. In other aspects, the epithelial ion channel comprises two delta subunits, one beta subunit, and one gamma subunit. In still further aspects, the epithelial ion channel comprises two delta subunits, two beta subunits, and two gamma subunits. In still further aspects, the epithelial ion channel comprises three delta subunits, three beta subunits, and three gamma subunits.

The method also provides a method for preparing such artificial lipid membrane comprising admixing a liposome comprising at least one phospholipid with an epithelial sodium ion channel or specific ratios of epithelial sodium ion channel subunits wherein the epithelial sodium ion channel or epithelial sodium ion channel subunits are dissolved in a suitable aqueous buffer comprising at least one detergent, incubating the liposome with the epithelial sodium ion channel or epithelial sodium ion channel subunit for a sufficient amount of time, and removing the at least one detergent.

The method of preparing the artificial lipid membrane may further comprise reconstituting the proteo-liposome into a planar lipid bilayer.

The invention further provides a method for identifying modulators of salty taste perception comprising: assembling at least one epithelial sodium ion channel in a lipid membrane, wherein the epithelial sodium ion channel comprises at least one of an alpha subunit, a beta subunit, a gamma subunit, a delta subunit, or an epsilon subunit; contacting the ion channel with a test compound in the presence of sodium or lithium; determining a modulation of the biological activity of the epithelial sodium ion channel in the presence of the test compound relative to the biological activity of the epithelial sodium ion channel in the absence of the test compound; and administering the test compound to a subject and determining a modulation of salty taste perception in the subject relative to the level of salty taste perception in the subject in the absence of the test compound. Preferably, the epithelial sodium ion channel comprises at least one beta subunit, at least one gamma subunit, and at least one delta subunit.

In some aspects, the epithelial ion channel comprises one alpha subunit, one beta subunit, and one gamma subunit. In other aspects, the epithelial ion channel comprises one alpha subunit, one beta subunit, one gamma subunit, and one epsilon subunit. In other aspects, the epithelial ion channel comprises two alpha subunits, one beta subunit, and one gamma subunit. In further aspects the epithelial ion channel comprises three alpha subunits, three beta subunits, and three gamma subunits. Additional aspects include those wherein the epithelial ion channel comprises one delta subunit, one beta subunit, and one gamma subunit. In other aspects, the epithelial ion channel comprises two delta subunits, one beta subunit, and one gamma subunit. In still further aspects, the epithelial ion channel comprises two delta subunits, two beta subunits, and two gamma subunits. In still further aspects, the epithelial ion channel comprises three delta subunits, three beta subunits, and three gamma subunits.

In some aspects, the delta subunit comprises the amino acid sequence of SEQ ID NO: 12. In some aspects, the delta subunit comprises the amino acid sequence of SEQ ID NO:9.

In some aspects, the subject is a human.

The method permits identification of a compound that reacts in vitro with the human salty taste receptor and which is perceived by subjects as salty. The invention thus provides such compounds which may be used in compositions by admixing the compounds with a pharmaceutically acceptable carrier, or foods or beverages to modulate the salty taste perception of the food or beverage. Preferably, the compounds allow perception of salty taste, but which have a reduced effect on blood pressure as compared to salt and which have no untoward effect on the subject.

In some aspects, the compounds can be additionally screened by cell based assays for epithelial sodium channel activity.

The invention also provides kits for identifying modulators of the human salty taste receptor comprising at least one form of phospholipid; substantially purified epithelial sodium ion channel subunits comprising alpha subunits, delta subunits, beta subunits, gamma subunits, or epsilon subunits; and optionally comprising an epithelial sodium ion channel modulator, sodium or lithium, and instructions for using the kit in a method for identifying modulators of the human salty taste receptor.

The instructions may provide, for example, directions to admix the subunits in specific ratios to achieve various forms of the epithelial sodium ion channel of interest. In some aspects, at least two subunits are added to be present at differing ratios relative to each other.

The kit may contain a modulator such as, but not limited to amiloride, phenamil, benzamil, chlorhexidine, or a source of guanidinium ion.

The invention also provides a method of modulating salty taste perception (either by stimulating salty taste perception or inhibiting salty taste perception) comprising contacting a human salty taste receptor with a compound that stimulates salty taste perception wherein the salty taste receptor comprises at least one beta polypeptide subunit, at least one gamma polypeptide subunit, and at least one delta polypeptide subunit wherein said delta polypeptide subunit comprises the amino acid sequence of SEQ ID NO:12, and wherein said compound specifically interacts with said delta subunit.

In some aspects, the human salty taste receptor comprises one alpha subunit, one beta subunit, and one gamma subunit. In other aspects, the salty taste receptor comprises one alpha subunit, one beta subunit, one gamma subunit, and one epsi- Ion subunit. In other aspects, the salty taste receptor comprises two alpha subunits, one beta subunit, and one gamma subunit. In further aspects the salty taste receptor comprises three alpha subunits, three beta subunits, and three gamma subunits. Additional aspects include those wherein the salty taste receptor comprises one delta subunit, one beta subunit, and one gamma subunit. In other aspects, the salty taste receptor comprises two delta subunits, one beta subunit, and one gamma subunit. In still further aspects, the salty taste receptor comprises two delta subunits, two beta subunits, and two gamma subunits. In still further aspects, the salty taste receptor comprises three delta subunits, three beta subunits, and three gamma subunits.

In some aspects the compound specifically interacts a portion of the delta subunit containing the amino acid sequence of SEQ ID NO:12. In some aspects, the compound binds to the portion of the delta subunit containing the amino acid sequence of SEQ ID NO:12.

BRIEF DESCRIPTION OF THE DRAWINGS

FIGS. 3 (a, b, c, d) shows an alignment of ENaC delta subunit sequenced from cDNA of ten individuals (labeled DENACA, DENACD, DENACE, DENACG, DENACH, DENACI, DENACJ, DENACT, DENACTV and DENACW, respectively), as compared with the GeneBank sequence of the top row (DENACGB). DENACA, DENACD, DENACE, DENACG, DENACH, DENACI, DENACJ, DENACT, DENACTV and DENACW correspond to SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, and SEQ ID NO:26, respectively.

FIG. 8 (a, b, c, d) shows an alignment of ENaC gamma subunit sequenced from cDNA of ten individuals (labled GENACA, GENACB, GENACD, GENACE, GENACG, GENACH, GENACJ, GENACT, GENACV, and GENACW, respectively) compared with the GeneBank sequence of the top row (GENACGB). GENACA, GENACB, GENACD, GENACE, GENACG, GENACH, GENACJ, GENACT, GENACV, and GENACW correspond to SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, and SEQ ID NO:36, respectively.

DETAILED DESCRIPTION

Figure 1:
FIG. 1 shows a human taste bud stained by an ATPase histochemical procedure.

It is to be understood that this invention is not limited to particular methods, reagents, compounds, compositions, or biological systems, which can, of course, vary. It is also to be understood that the terminology used herein is for the purpose of describing particular aspects only, and is not intended to be limiting.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein the "Epithelial Sodium Channel" or, as abbreviated, "ENaC," refers to a multisubunit protein that is responsible for flow of or transport of sodium ions across specific epithelium or cell membranes. ENaCs are generally composed of multiple subunits, generally α, β, γ subunits. There are also δ and ε subunits which may be in some ENaCs in specific tissues. The "salty taste receptor" as discovered herein, is a species of ENaC that is localized in taste cells and in one aspect is composed of β, γ, and δ subunits.

As used herein, "test compound" refers to any purified molecule, substantially purified molecule, molecules that are one or more components of a mixture of compounds, or a mixture of a compound with any other material that can be analyzed using the methods of the present invention. Test compounds can be organic or inorganic chemicals, or biomolecules, and all fragments, analogs, homologs, conjugates, and derivatives thereof. Biomolecules include proteins, polypeptides, nucleic acids, lipids, monosaccharides, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

As used herein, the terms "modulate" means any change, increase, or decrease in the amount, quality, or effect of a particular activity or protein. "Modulators" refer to any inhibitory or activating molecules identified using in vitro and in vivo assays for, e.g., agonists, antagonists, and their homologs, including fragments, variants, and mimetics, as defined herein, that exert substantially the same biological activity as the molecule. "Inhibitors" or "antagonists" are modulating compounds that reduce, decrease, block, prevent, delay activation, inactivate, desensitize, or downregulate the biological activity or expression of a molecule or pathway of interest. "Inducers," "activators," or "agonists" are modulating compounds that increase, induce, stimulate, open, activate, facilitate, enhance activation, sensitize, or upregulate a molecule or pathway of interest. In some preferred aspects of the invention, the level of inhibition or upregulation of the expression or biological activity of a molecule or pathway of interest refers to a decrease (inhibition or downregulation) or increase (upregulation) of greater than from about 50% to about 99%, and more specifically, about 50%, 51%, 52%, 53%, 54%, 55%, 56%, 57%, 58%, 59%, 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more. The inhibition or upregulation may be direct, i.e., operate on the molecule or pathway of interest itself, or indirect, i.e., operate on a molecule or pathway that affects the molecule or pathway of interest.

"Pharmaceutically acceptable carrier" refers to a medium that does not interfere with the effectiveness of the biological activity of the active ingredient(s) of a composition, and is not toxic to the subject to which it is administered.

"Ct" or "threshold cycle" refers to the PCR cycle in which a noticeable increase in reporter fluorescence above a baseline signal is initially detected.

"ΔCt" refers to the difference between the Ct of a sample assay and the Ct of a control sample. Thus, ΔCt=Ct(target)−Ct(control).

"ΔΔCt" refers to the difference between the average ΔCt value of a target sample and the average ΔCt for a corresponding calibrator sample. Thus, ΔΔCt(test sample)=AvgΔCt(test sample)−AvgΔCt(calibrator sample).

"Biological activity" as used herein refers to a measurable function of an ENaC, including but not limited to, maintenance of a sodium gradient across the membrane, changes in ion flux, changes in membrane potential, current amplitude, voltage gating, sensitivity to chlorhexidine, amiloride, or its analogs, stimulation by bretylium, novobiocin, or guanidinium ions, binding to subunit-specific monoclonal antibodies, and the like.

The present invention is based on the discovery that the human salty taste receptor is an epithelial sodium ion channel. It is thus an object of the present invention to use the precise molar ratios of the ENaC subunits and to reconstitute the ENaCs in a lipid bilayer in order to identify compounds that modulate the biological activity of the ENaCs. In particular it is an object of the present invention to use the precise molar ratios of the salty taste receptor subunits to reconstitute the salty taste receptor in a lipid bilayer in order to identify compounds that modulate the biological activity of the salty taste receptor and to identify compounds that modulate salty taste perception in human beings. Without intending to be limited to any particular theory or mechanism of action, it is believed that a passive influx of sodium ions through epithelial sodium channels in certain taste receptor cells causes a change in intracellular ion balance leading to a depolarization, ultimately resulting in neurotransmitter release, which in turn produces a perception of salty taste.

In one aspect, the invention provides assays to identify compounds that bind and/or modulate the human salty taste receptor. The methods comprise assembling at least one epithelial sodium ion channel in a lipid membrane, wherein the epithelial sodium ion channel comprises an alpha, beta, gamma, or delta subunit, contacting the at least one ion channel with a test compound in the presence of sodium or lithium, and determining a modulation of the biological activity of the at least one epithelial sodium ion channel in the presence of the test compound relative to the biological activity of the at least one subunit in the absence of the test compound.

Where the biological activity of the sample containing the test compound is higher than the activity in the sample lacking the test compound, the compound is an agonist. If the activity of the sample containing the test compound is lower than the activity in the sample lacking the test compound, the compound is an antagonist.

Epithelial sodium ion channels are heteromultimeric complexes that are comprised of different subunits. Various subunits of ENaC have been identified, and include, without limitation, the alpha subunit, the beta subunit, the gamma subunit, the delta subunit, and the epsilon subunit. The ENaC subunits may derived from any species, however, mammalian ENaC subunits are preferred and the most preferred species is human. Examples of nucleic acid sequences encoding human ENaC subunits and the deduced amino acid sequences are provided herein. Other subunits with amino acid sequences that are substantially homologous or which represent isoforms of the subunit proteins may be used in practicing the invention. Amino acid sequences that are "substantially homologous" are at least protein sequences that are from about 80% to about 100% identical to the sequence provided herein for the subunit sequence. More preferably, the sequences are about 85% to about 100% identical. Most preferably, the sequences are about 90%, 91%, 92%, 93%, 94%, 95%, 96%, 97%, 98%, 99%, or 100% identical to the reference sequence provided herein for the subunit.

Representative nucleotide sequences encoding human alpha subunit, human beta subunit, human gamma subunit, and human delta subunit are provided as SEQ ID NO:1, SEQ ID NO:3, SEQ ID NO:5, and SEQ ID NO:7, respectively. The deduced amino acid sequences for human alpha subunit, human beta subunit, human gamma subunit, and human delta subunit are provided as SEQ ID NO:2, SEQ ID NO:4, SEQ ID NO:6, and SEQ ID NO:8, respectively. In a preferred aspect for the salty taste receptor, the delta subunit comprises a cysteine at position 532 with respect to SEQ ID NO:8. The delta receptor with $Cys_{532}$ is shown in SEQ ID NO:9. Such substitution may arise due to a alteration in the triplet codon from tac to tgc (with respect to that shown in SEQ ID NO:7) and results in a change from tyrosine (Tyr) to cysteine (Cys).

In some aspects, the ENaC is comprised of at least one alpha subunit, at least one beta subunit, and at least one gamma subunit (e.g., (α)1(β)1(γ)1). In other aspects, the ENaC is comprised of at least one alpha subunit, at least one beta subunit, at least one gamma subunit, and at least one delta subunit. In other aspects, the ENaC is composed of two alpha subunits, one beta subunit, one gamma subunit (α2βγ). In other aspects, the ENaC is composed of three alpha subunits, three beta subunits, and three gamma subunits ((α)3(β)3(γ)3).

In another aspect, the ENaC comprises an epsilon subunit and at least one other subunit such as an alpha subunit, beta subunit, delta subunit, gamma subunit, or combinations thereof. In still other aspects the ENaC comprises a plurality of beta subunits. In a preferred aspect, the ENaC is comprised of at least one beta subunit, at least one gamma subunit, and at least one delta subunit (the salty taste receptor). The most preferred aspect is an ENaC comprising at least one beta, at least one gamma, and at least one delta subunit (e.g., (β)1(γ)1)(δ)1 in which the delta subunit contains $Cys_{532}$.

The various subunits can be present in the ENaC in different ratios relative to other subunits. The observed variation may relate to which tissue the particular ENaC of interest is expressed in. For example, but not by way of limitation, an ENaC can be comprised of two alpha, one beta, and one gamma subunit. Thus, in certain aspects of the invention, the ENaC assembled into a lipid membrane is comprised of at least two subunits that are present in different ratios relative to the other subunits. In other aspects, the ENaC is comprised of at least two subunits that are present in the same ratio relative to the other subunits. The ratios of the ENaC subunits may also vary depending on the tissue in which the ENaCs of interest are expressed. Further, there may be important sequence variability in the form of each subunit expressed in various tissues. For example, but not by way of limitation, the delta subunit of ENaC expressed in the salty taste receptor preferably has a cysteine in the putative amiloride binding site of delta at position 532 of SEQ ID NO:8 (which encodes human delta from kidney). Human kidney delta has a tyrosine at this position. Thus, when expressing a human salty taste receptor, it is preferred to use a delta with the putative amiloride binding site of MGSLCSLWFGA (SEQ ID NO: 12) which includes $CYS_{532}$. As this motif is at least a putative site for amiloride binding, other compounds that modulate the human salty taste receptor may also bind to this site.

In certain aspects of the invention, the lipid membranes produced with the ENaC subunits in them contain ENaC subunits that form the salty taste receptor. These salty taste receptors include at least one beta, at least one gamma, and at least one delta subunit. In preferred aspects, the delta subunit comprises $Cys_{532}$. In other aspects, the ENaC contains subunits selected from alpha, beta, gamma, delta, and epsilon. In some aspects, the ENaC is composed of at least one alpha, at least one beta, and at least one gamma. In other aspects, the ENaC comprises at least one epsilon subunit.

The ENaC or the various subunits that are to be assembled into the lipid membrane can be obtained from any source suitable in the art. For example, an ENaC or any subunit thereof can be freshly isolated from any cell that expresses and ENaC, including cell lines and stable cell lines. For example, but not by way of limitation, ENaC are expressed in neural tissue, the pancreas, testes, ovaries, tongue, colon, kidneys, lungs, sweat glands, and the like. In some aspects, the ENaC for salty taste perception is isolated from the papillae of the tongue. In other aspects, an ENaC or any subunit thereof can be recombinantly expressed, purified and used to reconstitute a lipid membrane to form functional ENaCs.

In certain aspects, each subunit of the ENaC is separately expressed in a recombinant expression system such as, but not limited to bacterial cells, Spodoptera frugiperda cells, mammalian cells, and frog oocytes. The expressed protein is purified by standard biochemical means as is well-known in the art. Alternatively, expressed protein may be immunopurified using immobilized antibodies that specifically bind the ENaC subunits. Methods for purifying proteins by immunoaffinity (using antibodies that specifically bind the subunit or ENaC of interest). In other aspects, the ENaC subunits are expressed as a fusion protein with a polypeptide that allows for rapid purification and subsequent cleavage from the expressed protein. Such purification systems include, but are not limited to the pGEX system (glutathione-S-transferase fusion proteins) and multi-histidine fusion proteins (for nickel binding affinity purification). These and other types of purification are described in numerous references and are well-known to those of skill in the art. In certain preferred aspects, the ENaC subunits are expressed simultaneously using a baculovirus system and Spodoptera frugiperda cells and membrane fractions are prepared as described in Rao, U.S. et al. (2002) "Activation of Large Conductance Sodium Channels Upon Expression of Amiloride-Sensitive Sodium Channel in SF9 Insect Cells" J. Biol. Chem. 277(7):4900-4905.

In certain aspects, the subunits of the ENaC are substantially purified prior to incorporation into the membrane. As used herein, "substantially purified" refers to subunits that are at least 80% free of contaminating material (e.g., proteins, polysaccharides, and lipids) derived from the cells from which they are obtained. Preferably, the subunits are at least about 85% free of contaminating material. More preferably, the subunits are at least about 90%, 91%, 92%, 93%, 94%, 95%, 96%, 97%, 98%, 99%, or more free of contaminating material.

To recreate a particular ENaC which may be present in a tissue in the artificial membranes of the invention, the ratio of the subunits present in the ENaC may be determined by quantitative PCR. As the ratio of protein subunits of a multimeric receptor often correlates to the amount of mRNA produced in a cell for the given receptor, quantitative PCR can provide an efficient means of determining the ratio of mRNA present. Protocols for performing quantitative PCR are well known in the art. Further, given the sequences of the ENaCs provided herein and the knowledge in the art and software available for selecting PCR oligonucleotide primers that can specifically and reliably amplify messages for particular genes, one of skill in the art may easily and routinely perform quantitative PCR on tissue samples and determine the identity and ratio of the subunits that form a particular ENaC. Assays for determining the relative amounts of mRNA are well known in the art. Once the ratio of mRNA is determined, one may extrapolate the amount of protein of each subunit that must be added to the membrane to provide the appropriate stoichiometric amounts of protein to form biologically active ENaCs.

The concentration of affinity-purified protein can be determined by measuring the total nitrogen content of the protein eluate and comparing the nitrogen content with the total protein content of the eluate. Nitrogen content can be determined by any means suitable in the art, such as the well-known Kjeldahl Nitrogen Method. Protein concentration can be determined, for example, by spectrophotometry whereby a protein sample is analyzed for its absorption of light at 280 nm to derive an absorption coefficient. Any means known in the art for assessing concentration and/or purity of protein may be used.

The invention thus provides artificial membrane systems containing substantially purified ENaC protein subunits that assemble into functional ENaCs. Specifically, the invention provides artificial membrane systems containing substantially purified human salty taste receptor. These membrane systems permit analysis of ENaCs, including, but not limited to the salty taste receptor apart from contaminating proteins such as endogenous ENaCs. The invention permits the assembly of ENaCs in which the subunits are added at known ratios to permit the assembly of precise ratios of selected subunits. The lipid membrane can comprise any combination of lipids.

Non-limiting examples of suitable lipids include phosphatidylcholine, phoshpatidylethanolamine, phostphatidylserine, phosphatidylglyine, phosphatidylinositol, sphingomyelin, cholesterol, cardiolipin, or a homolog, analog, or derivative thereof. Phospholipids are preferred, and can be obtained from any source suitable in the art. For example, the phospholipids can be extracted from a cell, or can be synthetic phospholipids, which are commercially available.

The lipid membrane can be in any conformation or phase, including without limitation, liposomes, a lipid bilayer, or the hexagonal phase. Liposomes and lipid bilayers are particularly preferred.

The effect of the test compound on the biological activity of the ENaC an be determined by any means suitable in the art. The test compound can be assessed at multiple concentrations. In some aspects, the test compound is assessed for its ability to modulate at least one biological activity of the ENaC. In preferred aspects, the ENaC is the salty taste receptor.

The biological activity of the ENaC can be determined by measuring the current of ENaC assembled in the lipid membrane. Voltage clamping is one preferable technique to measure ENaC current. Voltage clamp techniques are well known in the art. (Nagel, G et al. (2005) *J. Physiol.* 564(Pt 3):671-82; Staruschenko, A et al. (2004) *J. Biol. Chem.* 279:27729-34; Tong, Q et al. (2004) *J. Biol. Chem.* 279:22654-63; Sheng, S et al. (2000) *J. Biol. Chem.* 275:8572-81). The following parameters can be measured using a voltage clamp: single channel conductance, channel open time, voltage dependence, blockade induced by application of a particular compound, and activation induced by application of a particular compound. Other suitable techniques for measuring the biological activity of ENaCs include flux assays, patch clamping, voltage-sensitive dyes, and ion-sensitive dyes. Preferably, ENaC activity is measured by membrane electrophysiology or by assessing the change in fluorescence of a membrane potential dye in response to sodium or lithium, or analogs thereof (e.g., isotopes). All such assays are well known in the art. (Gill, S et al. (2003) *Assay Drug Dev. Technol.* 1:709-17, flux assay; Caldwell, R A et al. (2005) *Am. J. Physiol. Lung Cell Mol. Physiol.* 288:L813-9, patch clamp). A variety of voltage sensitive dyes are commercially available, including without limitation styryl dyes, oxonol dyes, and merocyanine-rhodanine dyes. Selection of the appropriate voltage sensitive dye is within the relevant skill in the art. Similarly, a variety of ion sensitive dyes are commercially available, including single excitation dyes, dual excitation ratiometric dyes, and dual emission ratiometric dyes.

The salty taste receptor is responsive to sodium and lithium ions. However, unlike other ENaCs, the human salty taste receptor is not sensitive to amiloride. Thus, amiloride should not inhibit or stimulate the salty taste receptor ENaC. Conversely, chlorhexidine acts as an inhibitor of the salty taste response in humans, and may be used in assays to identify salty taste modifiers. One may assess specificity of stimulation of the salty taste receptor with test compounds by showing that the effect is inhibited by chlorhexidine. Moreover, test compounds that can overcome the effect of chlorhexidine (and stimulate the salty taste receptors in the membrane systems of the invention) are strong salty taste enhancers. Basic compounds containing guanidinium ions as well as certain amines act as salty taste enhancers. These include guanidine, arginine, and homoarginine. Both L- and D-arginine are equally effective. While not wishing to be bound by any particular theory of operation, this lack of enantiomeric specificity suggests that the primary enhancing effect derives from a compact, basic moiety, in this case the guanidinium ion.

Thus, salty taste receptors in the membrane system of the invention may be stimulated by contacting them with a source of guanidinium ions. It may be assumed that these enhancing compounds interact directly with the human salty taste ion channel, since most sodium channel blockers and enhancers contain guanidinium groups that interact with acidic moieties inside the channel pore lumen. Thus, the molecular mechanisms of human salty taste share selected functional features in common with known sodium channels but also have unique pharmacological attributes.

Amiloride and amiloride derivatives (e.g., phenamil, benzamil and the like) may be useful in assessing other ENaCs, such as those containing an alpha subunit. Amiloride and derivatives may also be used in assays to inhibit the background (endogenous ENaCs) if the purity of the subunit preparations is low such that host cell ENaCs are contaminating the preparation. Thus, in some aspects of the invention, the methods further comprise contacting the ENaC with a sodium ion channel antagonist. Such antagonists are well-known to those of skill in the art. Preferably, the antagonist is amiloride, chlorhexidine, or homologs, analogs, or derivatives thereof.

The invention also includes within its scope high-throughput screening assays to identify compounds that modulate the biological activity of the salty taste receptor. High-throughput screening assays permit screening of large numbers of test compounds in an efficient manner. For example, but not by way of limitation, lipid membranes comprising an assembled ENaC can be dispersed throughout a multi-well plate such as a 96-well microtiter plate. Each well of the microtiter plate can be used to run a separate assay against a candidate modulator. A microtiter plate permits screening of multiple concentrations of a test compound, multiple test compounds, alone or in combination with other test compounds, and multiple ENaCs, including ENaCs with varying ratios of subdomains as described and exemplified herein under identical assay conditions. In other aspects of the invention, planar lipid bilayers containing the ENaC of interest is contacted with a test compound and a measurement is taken. The solution on one or both sides of the planar bilayer is changed and the bilayer is contacted with a second test compound. This may be continuously used as a high-throughput assay. The assays may take place in the presence of additional agonists or antagonists. Data obtained for the test compounds are compared with measurements taken in the presence of known agonists or antagonists and/or to control samples (such as a non-stimulatory/non-inhibitory medium).

Serial assays may be performed to narrow down the pool of test compounds that act as salty taste modifiers. For example, the in vitro assays of the invention may be combined with cell-based assays as a secondary or confirming screening step. Such assays have been described, for example, in published U.S. Patent Application 2005/0059094 to Servant et al.

An additional aspect of the invention features methods for identifying compounds that modulate salty taste perception in a subject by a combination of in vitro and in vivo screening assays. In one aspect, a test compound is first screened in vitro to determine its modulatory effect on an epithelial sodium ion channel, and then screened further in vivo to determine if the compound can modulate, preferably enhance, salty taste perception in a subject.

In one aspect, the in vitro screening assay comprises identifying modulators of the human salty taste receptor comprising contacting a test compound with at least one ENaC and determining a decrease in the biological activity of the ENaC in the presence of the test compound relative to the biological activity of the ENaC in the absence of the test compound. This aspect can be practiced according to the details described herein. In one aspect, the in vivo screening assay comprises identifying compounds that enhance salty taste perception in a subject comprising administering a test compound to the subject and determining whether salty taste perception is enhanced in the subject relative to the level of salty taste perception by the subject in the absence of the test compound.

For in vivo screening, subjects can be recruited via an Institutional Review Board-approved method such as general advertisement in print media. Prior to entering the study, each subject provides informed consent. The participants can be requested to refrain from eating, drinking or chewing gum for at least one hour prior to testing. Subjects can be paid to participate in the study.

Experimental solutions containing a candidate test compound to be administered to study subjects can be presented in the form of a binary mixture such as the compound and an inorganic salt such as NaCl. Preliminary experiments can be carried out to establish an appropriate concentration range for the test compound and inorganic salts. For example, four concentrations of the test compound are used with four concentrations of the inorganic salts. Aqueous solutions can be prepared to encompass all possible combinations of the concentrations of the test compound with the inorganic salts.

To assess the salty taste amplifying properties of a given stimulus, any means suitable in the art can be used. One non-limiting example of such means is the method of magnitude estimation. Magnitude estimation measures ratings of the perceived intensities of saltiness from a sample. Subjects participating in saltiness assessments can be instructed to rate the saltiness or relative saltiness of a solution. Each solution can be sampled by the subject once, twice, three times, or more.

Prior to sampling a test solution, subjects can be instructed to rinse their mouth. For example, subjects can be instructed to rinse with and expectorate water four times, preferably within a short duration of time such as period of approximately two minutes. Test samples and inorganic salt solutions can then be administered to the subjects, preferably in random order, and without replacement. For example, solutions can be prepared in polystyrene medicine cups (Dynarex, N.Y.) in 10 ml aliquots, and administered to the subjects. The subject can be instructed to rate the relative saltiness of the solution, and the relative saltiness ratings for each solution can be arithmetically averaged to yield single ratings of saltiness.

Magnitude estimation may not reveal differences due to variations in subject number use. To eliminate the variance produced by idiosyncratic number usage in the magnitude estimation task, the saltiness ratings can be standardized to the grand arithmetic mean of the saltiness ratings of NaCl alone in water (averaged across all NaCl concentrations). Each subject's mean saltiness rating can be divided into the grand saltiness mean, and the quotient can be used as the multiplicative standardization factor for that individual's saltiness rating. This procedure equates mean saltiness ratings of NaCl in water across subjects.

Analysis of variance (ANOVA) can be conducted on the standardized repeated measures data from the magnitude estimation, and post-hoc pairwise comparisons can be conducted with Tukey's honest significant difference (HSD) analysis.

An alternative to magnitude estimation is a forced-ranking procedure, wherein a series of two-alternative forced-choice pairings are used to rank the saltiness of aqueous solutions of NaCl in the presence or absence of a test compound putative enhancer. In this procedure, subjects can be instructed to taste half of the first solution (for example, 5 ml or 10 ml solution) of the first pair of samples for three seconds and expectorate. Subjects then rinse twice and taste half of the second sample, expectorate, rinse twice and taste the remainder of the two solutions using the same procedure. After tasting both solutions twice, subjects can be asked to indicate which solution they thought was saltier. If they report that neither solution seemed saltier, subjects can be asked to guess (forced-choice). The procedure can repeated for all samples.

The saltiness rankings can be calculated based on the number of times a particular solution is chosen as being saltier than all other solutions using the Friedman analysis of pairwise rankings. The Tukey HSD can be calculated to determine if the differences between individual rankings are significant.

Compounds identified by any of the foregoing inventive screening methods are contemplated to be within the scope of this invention. Such compounds are preferably agonists of ENaCs, more preferably agonists of the human salty taste receptor, and even more preferably are enhancers of human salty taste receptors. Such compounds may be formulated as a nutraceutical or pharmaceutical composition by admixing such compound in an amount effective to enhance salty taste perception in the subject to which it is administered and a pharmaceutically or nutraceutically acceptable carrier, as described herein.

It is an object of the invention to use the assays to identify compounds that are perceived as salty, as well as to identify compounds that enhance salty taste (such that a reduced amount of sodium or lithium is perceived as a higher concentration of sodium or lithium). The invention enables the screening of libraries of compounds including natural or synthetic molecules including, but not limited to proteins, peptides, oligonucleotides, polynucleotides, polysaccharides, lipids, small organic molecules, and the like, for their ability to act as salt substitutes, salty taste enhancers, or salty taste inhibitors. The invention includes salt substitutes, salty taste enhancers, and salty taste inhibitors identified by the methods of the invention.

Also featured in accordance with the present invention are artificial lipid membranes and methods for preparing the same. The artificial lipid membranes comprise at least one lipid and an assembled ENaC or at least one subunit of an ENaC. In preferred aspects, the ENaC is a salty taste receptor. The lipid membrane can be comprised of any suitable lipid, and are preferably comprised of phospholipids. Suitable lipids include, without limitation, phosphatidylcholine, phoshpatidylethanolamine, phostphatidylserine, phosphatidylglyine, phosphatidylinositol, sphingomyelin, cholesterol, cardiolipin, or a homolog, analog, or derivative thereof, and these can be obtained from any source suitable in the art. The lipid membrane can be in any conformation, and preferably is a liposome or lipid bilayer.

In one aspect, an artificial lipid membrane is prepared by admixing a liposome that comprises at least one phospholipid with an ENaC or a particular subunit or subunits of an ENaC that has dissolved in a suitable aqueous buffer. The aqueous buffer comprises at least one detergent. Suitable detergents are well known in the art, and include without limitation, Tween, Triton, CHAPS, sodium cholate, and octyl-glucoside. After mixing the phospholipids and ENaC or subunits thereof, the mixture is allowed to incubate for several minutes, preferably at least about 20 minutes, to permit assembly of the ENaC into a lipid membrane. Following the incubation, the detergent is removed according to any means suitable in the art, such as those described and exemplified herein. Other methods known in the art of preparing lipids and liposomes containing proteins may be used to produce the lipids and liposomes containing the ENaC subunits.

In some aspects, the ENaC is assembled into a liposome. The liposome can be converted into a planar lipid bilayer by use of techniques that are well known and routine in the art, including those that are described and exemplified herein. In some aspects, the liposomes contain a substance other than found in the surrounding milieu. For example, but not by way of limitation, the liposomes may contain a fluorescent voltage-sensitive or membrane potential dye that is responsive to sodium or lithium, to indicate a change in sodium content as a marker of sodium flow upon stimulation with a test compound.

The invention also features kits for identifying modulators of the human salty taste receptor. The kits comprise at least one phospholipid, an isolated epithelial sodium ion channel subunit(s), and optionally a source of sodium and/or lithium ions, and instructions for using the kit in a method for identifying modulators of the human salty taste receptor. In some aspects, the kits optionally comprise an epithelial sodium ion channel antagonist and/or agonist.

The invention provides a method for modulating salty taste perception in a subject by contacting a salty taste receptor with a compound that specifically interacts with the putative amiloride-sensitive region of the delta subunit that contains $Cys_{532}$. In human subjects, this delta subunit comprises the amino acid sequence of SEQ ID NO: 12. The modulators may enhance or inhibit salty taste perception by either stimulating the receptor or blocking the receptor. The compounds may interact with the delta receptor by binding to the receptor, preferably in the putative amiloride sensitive region having the amino acid sequence of SEQ ID NO: 12.

Using computer programs for rational-based drug design that are available in the art, molecular modeling may be performed based on the primary amino acid sequence data available herein and knowledge in the art as to tertiary structure of ion channels to provide a three dimensional model of the human salty taste receptor. Such modeling permits the rational selection of candidate compounds that will interact with specific modulatory sites including, as example, the putative amiloride binding site of the delta subunit, motif SEQ ID NO: 12. These compounds, or classes of compounds, will act as salty taste modifiers. Compounds that interact with these regions (e.g., delta subunit SEQ ID NO: 12) are useful as modifiers of salty taste perception. Thus, the data presented herein provide a structural-functional relationship between the subunits comprising the salty taste receptor and the areas of the subunits that are likely involved in salty taste perception.

The following actual and prophetic examples are provided to describe the invention in more detail. They are intended to illustrate, not to limit the invention.

EXAMPLE 1

Procedure for Obtaining Human Fungiform Papillae and Taste Cells. Human fungiform papillae containing taste buds are routinely obtained from the anterior dorsal surface of the tongues of volunteers by a minor surgical biopsy procedure carried out under local anesthesia. The general procedure is described in Spielman, A I et al. Collection of taste tissue from mammals. *Experimental Cell Biology of Taste and Olfaction*. Spielman A I and Brand J G eds. CRC Press, Boca Raton, Fla., pp 25-32. Volunteers give informed consent. This procedure has been reviewed and approved by an Institutional Review Board. The excised papillae can be subsequently used either for RNA extraction, immunohistochemistry or in situ hybridization, or in a procedure that results in a suspension of isolated taste cells.

RNA extraction, histochemistry an in situ analysis. When used for total RNA extraction, papillae are immediately subjected to a standard extraction procedure using TRIzol™ reagent (Invitrogen, Carlsbad, Calif.). The RNA extract is treated with DNase to remove most genomic DNA. Any DNA remaining could otherwise yield false positive results in subsequent steps where the use of intron-spanning primers is not possible. Genomic material, however, is useful in quantitative reverse trancriptase polymerase chain reaction (QRT-PCR) because the single copy of the genomic DNA signals the point of highest sensitivity of the PCR, and provides thereby a convenient end-point for the procedure. Reverse transcription is then performed on the RNA to yield a DNA copy of the RNA, known as complementary DNA or cDNA. This cDNA will used as the substrate in the polymerase chain reaction.

Because the fungiform papillae RNA and subsequent cDNA are generally of high quality, the entire coding sequence or open reading frame (ORF) of the protein under study can be immediately amplified. The oligo-nucleotide primers used to effect this amplification are designed based on the published sequence of the same or similar protein annotated in GenBank. The PCR reaction products can be analyzed by agarose gel electrophoresis. This procedure is often used to obtain the entire coding sequence of a gene known to be expressed in taste bud cells, the full sequence of which cannot be obtained readily from single cell analysis.

Figure 2:
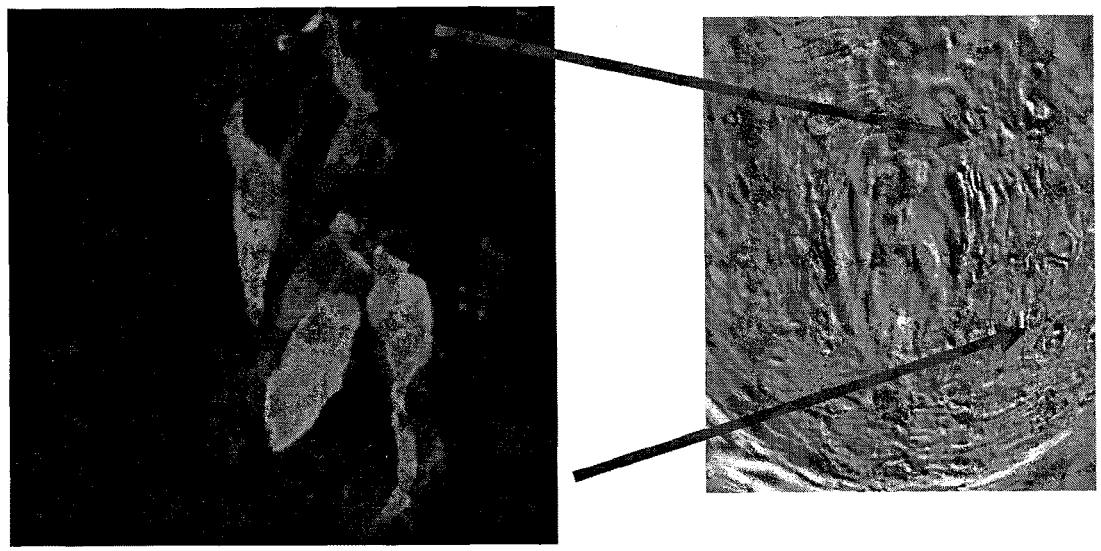
FIG. 2 shows antibody detection of the second messenger enzyme, phospholipase Cbeta2 (PLCbeta2) using an immunohistochemical procedure on human taste cells. Panel A shows the subset of cells labeled by the antibody. Panel B is a contrast image of the taste bud and of the surrounding fungiform papillae.

The excised papillae may also be used for general or immunohistochemical, or in situ hybridization analysis. Various techniques and procedures are available and can be used to fix and protect the tissue. As an example, FIG. 1 shows a human taste bud stained by an ATPase histochemical procedure. FIG. 2 shows antibody detection of the second messenger enzyme, phospholipase Cbeta2 (PLCbeta2) using an immunohistochemical procedure on human taste cells. The procedure is as follows: Histological sections (8 to 10 microns) of fungiform papillae were washed three times in 1×PBS for 10 minutes, placed in blocking buffer at room temperature for 4-18 hours. Blocking buffer was removed and primary antibody (rabbit anti-PLCbeta2) was added in three concentrations (1:50, 1:100, and 1:200 in buffer). The primary antibody solution was removed and the slides were washed three times in PBS. The first wash drained immediately while the subsequent washes were incubated for 10-20 minutes each. Excess fluid was removed and a the secondary antibody solution (CY3-labeled goat anti-rabbit, 1:1000) was added to the sections and the slides were incubated at room temperature for 45-120 minutes. The slides were washed three times in PBS. The first wash drained immediately while the subsequent washes were incubated for 10-20 minutes each. The excess fluid was drained, but slides were allowed to remain wet. Coverslips were placed on the slides and the slides were examined under a fluorescence microscope.

RT-PCR for identifying ENaC subunits and sequencing the same. Extraction of total RNA from biopsied fungiform papillae is carried out as described above, without DNase treatment, followed by synthesis of first-strand cDNA. Amplification of ENaC subunits (no more than 500 bp in size) can be performed with the PCR Core System I reagent kit (Promega Corp., Madison Wis.) using primers as above.

If a product of apparently the correct size is obtained, this product is excised from the gel and purified. The product is then ligated into a plasmid vector to yield a recombinant plasmid which has the gene for the coding sequence of the protein (e.g., ENaC δ) inserted into it. The recombinant plasmid is used to transform bacterial cells which, when provided with an appropriate growth medium, produce large amounts of plasmid. Purification of the bacterial culture yields the recombinant plasmid in a pure form, which enables one to get the sequence of the protein gene from human fungiform papillae. Finally, a bioinformatic analysis of the sequence, using the BLAST program confirms that the correct sequence has indeed been obtained.

Using this procedure, evidence was found for transcripts of four ENaC subunit types in human fungiform papillae. These subunits are the alpha, beta, gamma, and delta ENaC subunits. The complete ORF of the alpha subunit was rarely observed, but the complete ORF of the other subunits was nearly always observed. Surprisingly, it was discovered that the delta subunit of ENaC is present in human fungiform papillae.

EXAMPLE 2

Identification of the Human Salty Taste Receptor and the Importance of the Delta Subunit In accordance with the present invention, the delta subunit of the ENaC in the fungiform (taste) papillae of humans. The clones in which the subunit was detected were from pooled cDNA from 3 individuals who agreed to undergo a biopsy procedure to remove several fungiform papillae from the anterior dorsal surface of the tongue.

Characteristics of the delta subunit. The delta subunit of the epithelial sodium channel was detected in the fungiform papillae from thirteen individuals by RT-PCR. The detected fragments were amplified by PCR and subcloned. The polynucleotide encoding delta subunit from these thirteen individuals was then fully sequenced. It was determined that the human delta subunit from fungiform papillae differed from human delta subunit cloned from kidney in the putative amiloride binding site. The putative amiloride binding site contains a tyrosine at amino acid 532 in delta subunit from kidney (SEQ ID NO:8), but amino acid 532 in delta from fungiform papillae was cysteines in each of the thirteen samples sequenced (SEQ ID NO:9):

TABLE 1

| Source of delta | Sequence of putative amiloride binding site | |
|---|---|---|
| Kidney delta: | MGSLYSLWFGA | (SEQ ID NO: 11) |
| Taste delta # 1: | MGSLCSLWFGA | (SEQ ID NO: 12) |
| Taste delta # 2: | MGSLCSLWFGA | (SEQ ID NO: 12) |
| Taste delta # 3: | MGSLCSLWFGA | (SEQ ID NO: 12) |

FIG. 3 shows an amino acid sequence alignment of 11 delta subunits, where the first sequence is the GenBank sequence with the other 10 sequences being from 10 different individuals. At position 180, a possible polymorphism (R to P) is indicated. Other positions indicating possible polymorphisms are with positions 278 (F to I), 355 (S to R), 389 (E to Q), and 566 (R to H). Position 566 has also been implicated in amiloride binding. Without intending to be limited to any particular theory or mechanism of action, the polymorphisms may play a role in sensitivity to salty stimuli or may play a role in sensitivity to taste modulators.

The Y to C change at position 532 is significant as it may help explain why rat salty taste receptors are apparently amiloride sensitive while human salty taste receptors are not. As the rat's delta ENaC subunit is a psuedogene, it is not expressed. It is believed that the amiloride-sensitive alpha subunit functions as part of the salty receptor in rat. Although this substitution does not significantly alter the receptor sensitivity and specificity, the pharmacology of the channel is altered.

Figure 4:
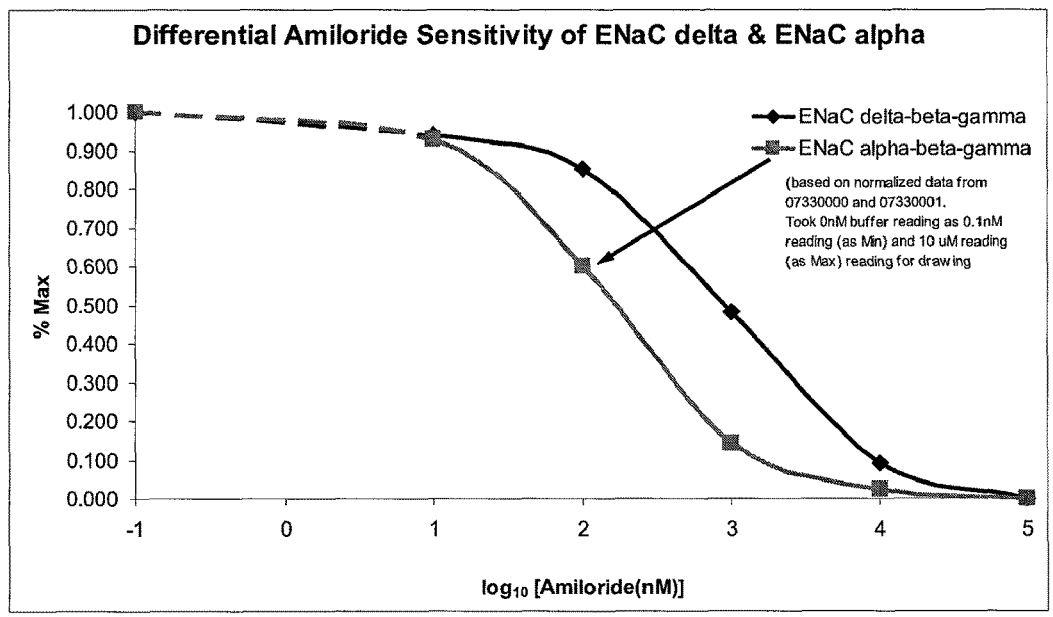
FIG. 4 shows amiloride inhibition of ENaC of different composition. ENaC composed of human delta, beta, gamma was less sensitive to amiloride than that composed of human alpha, beta, gamma.

While the delta subunit is amiloride sensitive, it is less so than the alpha (FIG. 4). Thus, if the human salty taste receptor ENaC contained the usual form of delta, it too should show amiloride sensitivity. However, the putative amiloride binding site in delta from human taste cells contains a non-conservative substitution and may therefore have a different sensitivity to amiloride than delta subunit in kidney. Without intending to be limited to any particular theory or mechanism of action, it delta shows less sensitivity, this observation potentially can be interpreted to mean that delta is in the human salty taste receptor, particularly because amiloride cannot cross tight junctions. Because of the differences between rat and human, the rat is probably not a good model for salty taste perception in humans.

Figure 5:
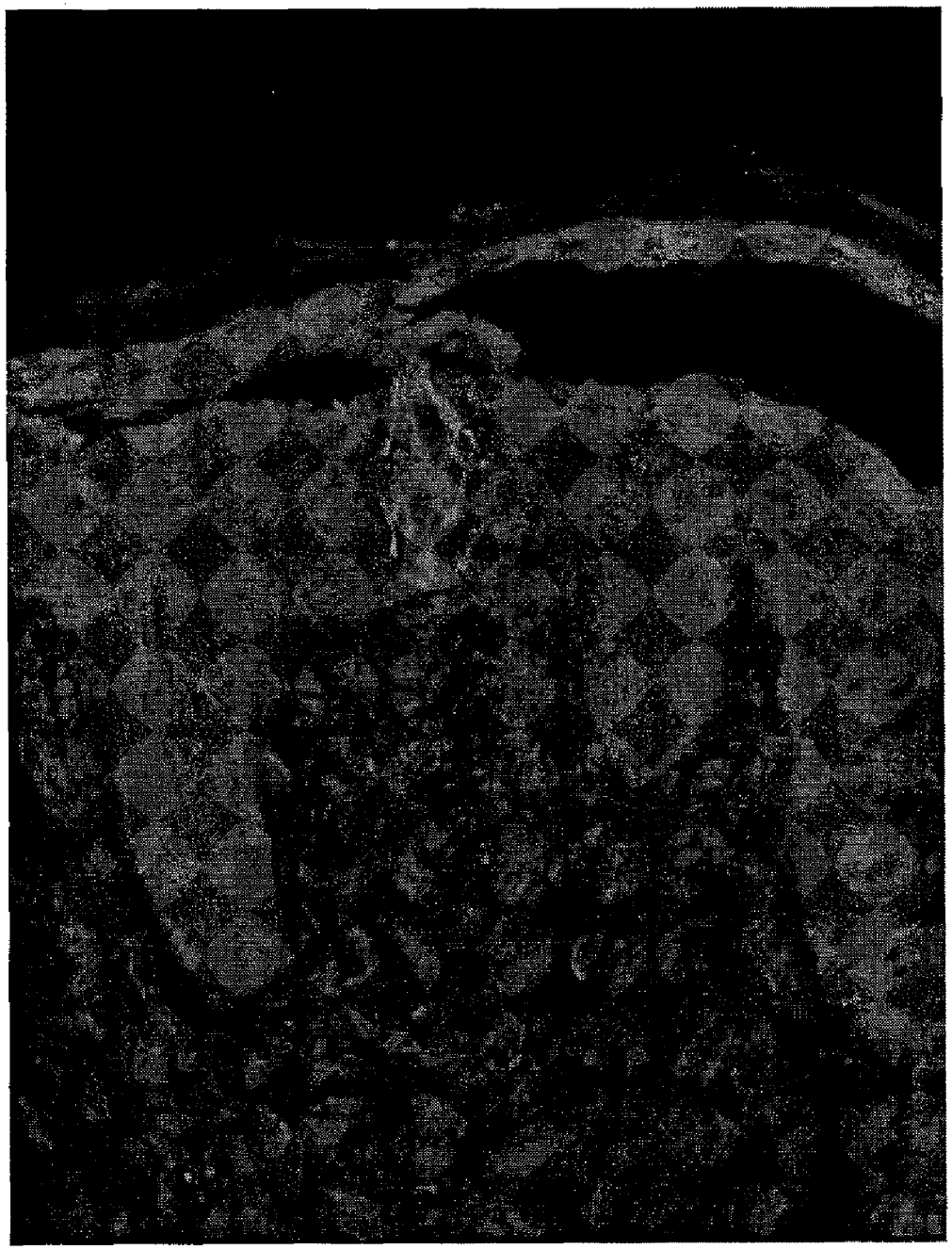
FIG. 5 shows immuno-labeling of a subset of cells in a human taste bud.

Cellular specificity of the human fungiform delta ENaC subunit. A human taste bud is shown in FIG. 1, wherein an 8 micron section of a human fungiform papilla is stained by an ATPase histochemical procedure. The question now became whether some, all, or none of these taste cells expressed delta ENaC. To view only those cells expressing the delta subunit, an antibody to the delta form of human ENaC was raised in rabbits. A representative photograph is shown in FIG. 5. The slide shows tissue specific labeling on a subset of cells within a human taste bud. The implication is that the human salty taste receptor is an ENaC composed of a multimer of delta, beta, and gamma subunits or of subunits alpha, delta, beta, and gamma. This specificity of delta in the taste cells accompanied by a notable dearth of full-length alpha in these same buds, suggested that the human salty taste receptor is a delta-containing ENaC and not simply an alpha, beta, gamma ENaC as suggested by others.

Figure 6:
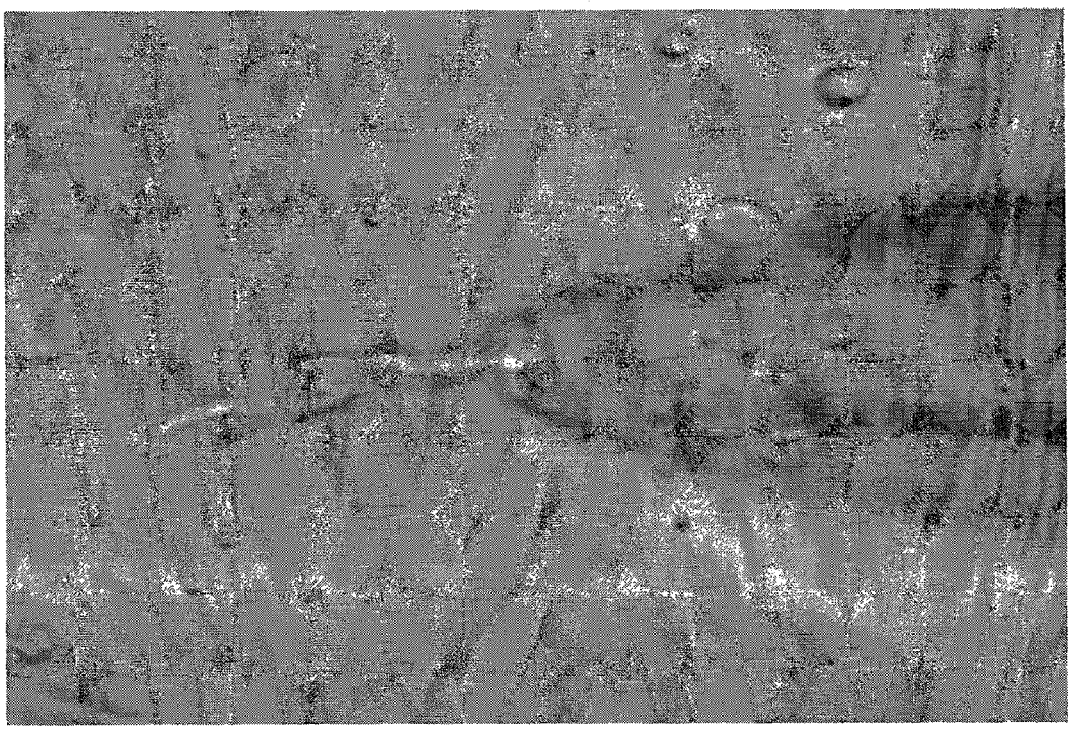
FIG. 6 shows the capture of an isolated human taste bud cell by a micro-pipette from an aqueous suspension. The cell thus captured is placed in an RNA-preserving medium for further study.

Isolation of human taste bud cells. A suspension of single isolated taste bud cells was prepared from human fungiform papillae by incubation of biopsied papillae in a collagenase-based enzymatic procedure, followed by washing of the papillae to effectively removed enzyme, then trituration of same through a glass pipette. The resulting suspension was enriched for cells of the taste bud. Individual cells were captured using a glass micropipette (See FIG. 6) and individually placed into a tube containing 2 to 10 µl of RNAlater.

The delta subunit is located in taste bud cells. cDNA was derived from 7 human fungiform taste cells that were individually isolated and captured, as described above, and then pooled. A product of the correct size (~500 bp) was noted and its identity as a human ENaC delta subunit was confirmed by sequencing. Using this PCR procedure of identifying overlapping segments of the ORF of delta ENaC, the complete ORF of taste cell delta ENaC was obtained.

Figure 7:
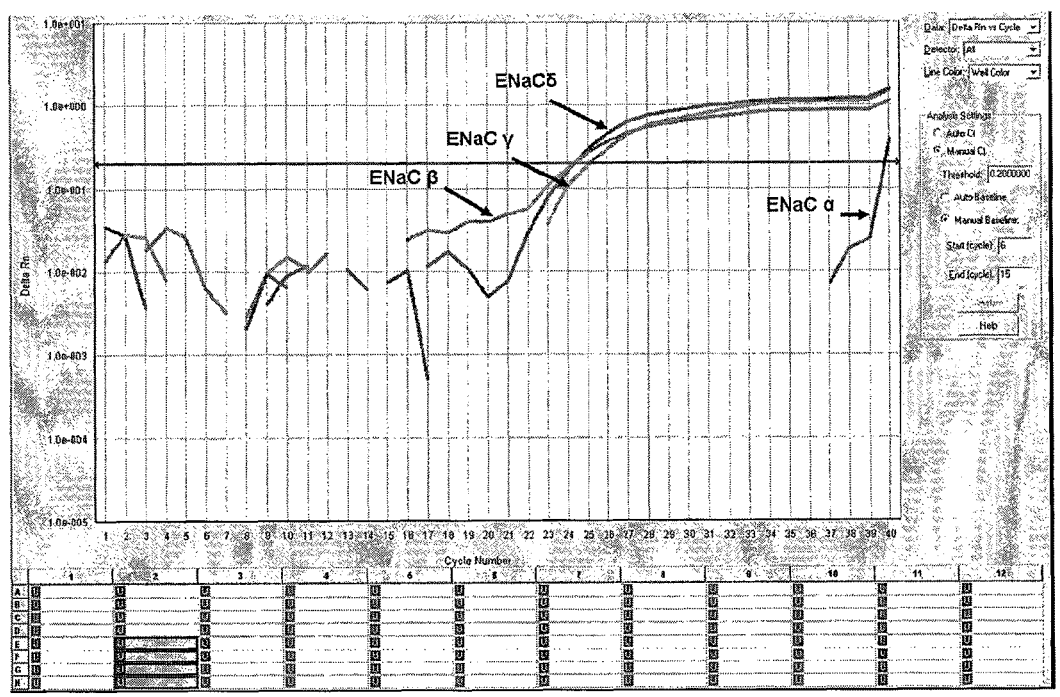
FIG. 7 shows an early quantitative RT-PCR of a single cell tracing the amplification of partial transcripts of the ENaC subunits, alpha, beta, gamma, and delta. The result suggests a cell containing equal copies of delta, beta, and gamma, with the alpha transcript showing as a genomic control.

Single cell RT-PCR using nested primers was also performed, and revealed that two out of twelve human taste bud cells tested provided strong evidence for expression of delta, beta, and gamma subunits, without expressing full-length alpha (data not shown). One early single cell Q-RT-PCR revealed no message for the alpha subunit but approximately equal numbers of message copies for delta, gamma and beta (FIG. 7).

Using calcium imaging on a preparation of isolated taste cells, it is possible to identify those individual cells that are activated by sodium chloride. These cells are captured and their contents analyzed by Q-SC-RT-PCR. In a group of 30 salt sensitive cells, the primary expressed subunit was determined to be delta. Eight expressed delta, beta, and gamma, while 7 expressed delta, alpha, beta, and gamma.

An alignment of the amino acid sequences of the 10 gamma subunits sequenced from taste cells as compared to the GenBank sequence for gamma is shown in FIG. 8.

Having identified the salty receptor as delta, beta, gamma or delta, alpha, beta, gamma, each subunit will be expressed and reconstituted into lipid bilayers for analyses, as provided by the examples below.

EXAMPLE 3

Preparation of Liposomes and Artificial Lipid Bilayers

This example demonstrates the techniques that are readily practiced to solubilize an abundant receptor from its membrane milieu, purify the receptor, and reconstitute the receptor in an artificial lipid membrane such as a lipid bilayer. Such membranes serve as an artificial biological membrane in which the receptor resumes its native conformation and can be studied in detail and in isolation, e.g., without interference from other proteins or the metabolic whimsy of a living cell.

This example, in part, describes the extraction, purification, and membrane-reconstitution of a taste receptor for L-arginine (L-arg) from catfish. The methods, which are published and described in Grosvenor, W et al. (2004) *BMC Neuroscience* 5:25, can be readily adapted for reconstitution of ENaC, ENaC subunits, and salty taste receptors in lipid membranes as described below. The catfish has served as a model for taste receptor studies because the receptors are very sensitive to certain amino acids. One such amino acid is L-arg. Like the ENaC, the taste receptor for L-arg in catfish is an ion channel. Parallel approaches are utilized in solubilizing the L-arg and ENaC-type receptors. The receptors differ primarily by origin—the L-arg receptor is purified from catfish taste tissue and the ENaC subunits are synthesized by a heterologous cell culture expression system.

Liposome generation. Liposomes are used to carry the solubilized receptor to the bilayer construct. The major challenge to studying a membrane-soluble protein is developing a procedure to move the protein from its native membrane or synthesis end point to an artificial lipid bilayer. Solubilization usually uses detergent and this detergent must be removed to avoid damage to the bilayer. The liposome performs this transfer by taking up the protein from the detergent system and giving it up to the bilayer.

Liposomes are prepared by adding 5 mg of the mixture of 1,2-dioleoyl-sn-glycero-3-phosphoethanolamine: 1,2-dioleoyl-sn-glycero-3-phosphocholine (DOPE:DOPC) in a 2:1 ratio in 0.5 ml of chloroform to a round bottom flask. The flask is rotated for 30-40 min at 4° C. After evaporation of the chloroform, a thin layer of lipid is formed to which 2 ml of buffer solution (300 mM NaCl, 50 mM Tris, pH=7) is added. After addition of the buffer, the flask is bath-sonicated 3 times with 3-5 min pulses to induce liposome formation. Alternatively, the probe sonicator can be pulsed for only 30-40 sec.

Dissolution of the L-ArgR into liposomes and pharmacology of L-ArgR in a lipid membrane. An amount (0.01 to 0.5 µg) of the L-ArgR dissolved in 100 mM NaCl/50 mM Tris, pH=7.1 containing one of several detergents such as Tween, CHAPS, Triton, Sodium Cholate, or/and Octyl-glucoside is added to the liposomes. The ratio of protein to lipid (mass:mass) for measuring channel activity as single cannel events is 1:2000-5000. The ratio for measuring macroscopic properties is in the range of 1:50-100. The protein-lipid mixture is incubated for 20-30 mins.

Figure 9:
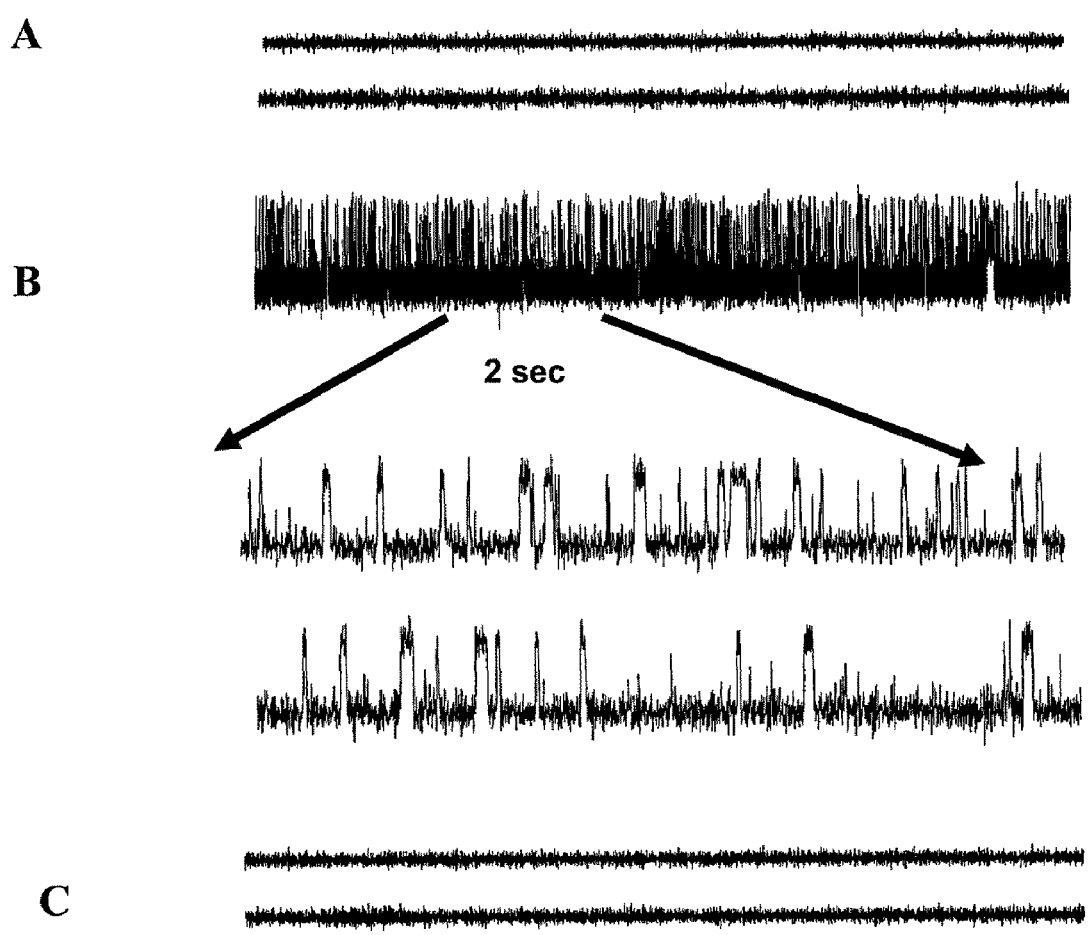
FIG. 9 shows single channel recording of the activity of the catfish putative taste receptor for L-arginine in planar lipid bilayers. Proteoliposomes containing purified receptor protein from catfish taste epithelium are fused to planar lipid bilayers. Control records (trace shown in part A) were obtained after addition of proteolipisomes to the membrane bathing solution before addition of L-Arg. The addition of 10 µM L-Arg to the cis-side of the bilayer evoked regular periodic channel activity (trace shown in panel B, including the inset that shows the current record at an expanded scale). After several minutes of single channel recording, 100 µM D-Arg was added to the cis-side (trace shown in panel C) and activity ceased. Transmembrane potential was −100 mV. Traces shown in all panels are continuous records of that specific condition.

The properties of the L-ArgR as measured in the bilayer are very similar to those observed through taste nerve recordings from the animal, when the L-ArgR is in its native state. For example, the taste nerve recordings indicate that the sensitivity of the native receptor is in the tenths of uM of L-arg, while D-arg inhibits the receptor. FIG. 9 shows that when the L-ArgR is reconstituted into a bilayer, the same properties are seen. This demonstrates that a receptor like the L-ArgR is more directly and more readily studied when in the bilayer than when in the native state where its activity must be inferred from secondary neural recordings.

Reconstitution of the ENaC protein into liposomes. An amount (0.01 to 0.5 µg) of the sodium channel of interest, including ENaCα, ENaCδ, or specific ratio mixtures derived from the ENaC subunits, α, β, γ, δ, dissolved in 100 mM NaCl/50 mM Tris, pH=7.1 containing one of several detergents such as Tween, CHAPS, Triton, Sodium Cholate, or/and Octyl-glucoside will be added to the liposomes. The ratio of protein to lipid (mass:mass) for measuring channel activity as single cannel events is 1:2000-5000. The ratio for measuring macroscopic properties is in the range of 1:50-100. The protein-lipid mixture will be incubated for 20-30 mins. This procedure will be followed because the ENaC protein, being a membrane channel, needs to remain in solution while it is reconstituted into liposomes.

Reconstituted detergent-free proteo-liposomes containing one or more of the ENaCs can be prepared at least two ways. In one method, they can be formed through centrifugation of the protein:lipid mixture through gel filtration columns. These gel columns are prepared from Sephadex G-50 (fine), swollen overnight, and poured into 5-ml disposable columns (1.5-ml bed volume). Columns are pre-spun in a centrifuge at 1,000×g. The protein:lipid mixture is loaded on the top of the column, and proteo-liposomes free of detergent can be recovered by spinning the columns at 700 g for 1 min. Alternatively, detergent can be removed by dialysis. For dialysis, the protein:lipid mixture is loaded into a cassette dialysis unit and the mixture dialyzed overnight against 2000 ml of a Tris/NaCl/sucrose (detergent-free) buffer at 4° C. Phospholipid vesicles containing the protein are expected to form spontaneously as the concentration of detergent decreases during the dialysis.

Reconstitution of the channel proteins from proteo-liposomes into a planar lipid bilayer. The planar lipid bilayer is formed on an aperture between two aqueous compartments, which for operational purposes are called cis and trans compartments. The voltage generator will be connected to the cis compartment, with an Ag/AgCl electrode, to control membrane potential. The trans compartment (virtual ground) will be connected to the input of the current-measuring amplifier through a second Ag/AgCl electrode.

Forming the bilayer. A 4:1 mixture of DOPE:DOPC will be dissolved in 25 µl of n-decane (concentration ranging from 15 to 25 mg/ml). This mixture will be kept at room temperature and prepared each day that the experiment is performed. Electrode compartments will be filled with 3 M KCl and the Ag/AgCl electrodes will be placed in the compartment. The cis and trans compartments will be filled with the recording bath solution (100 mM NaCl, 10 Tris, pH 7) and agar bridges will be placed between them and the electrode compartments. To form the bilayer, a droplet of the lipid mixture will be spread onto the hole from the cis side.

The lipids can be determined to be completely formed around the hole when the resistance increased and the signal is not saturating. To verify that an organized bilayer has formed, the voltage pulses across the bilayer can be applied and "capacitive currents" can be measured. For a hole of 100 µm, the capacitance is expected to be of the order of 50-100 pF. The electrical resistance of the bilayer is expected to be higher than 109 Ohm.

Reconstitution. After the bilayer has formed, 10-15 μl of the proteo-liposomes will be added to the cis-side of the bilayer under constant stirring. When channel subunits are incorporated into the bilayer, the currents are expected to change in steps. Macroscopic current will be measured when many channels are incorporated.

Liposome fusion with the bilayer happens spontaneously, and currents will be able to be recorded within about 5 to 30 minutes. In some cases, it may be necessary to facilitate the liposome fusion by: creating a concentration gradient across the liposome by adding the liposomes formed previously in 300 mM NaCl to a bilayer bathing solution containing 100 mM NaCl, or by creating a concentration gradient across the lipid bilayer by adding 100 mM NaCl to the cis side and 10 mM NaCl to the trans side, or by changing bilayer and/or liposome lipid composition by the addition of negatively charged lipid such as DOPS to the bilayer.

EXAMPLE 4

Expression of Varying Ratios of ENaC Receptor Subdomains In Lipid Bilayers

This is a prophetic example. The ENaC is a heteromultimeric complex generally comprised of three subunits: either of subunits $\alpha$, $\beta$, and $\gamma$ (in most tissues as $\alpha 2 \beta\gamma$ complex) or subunits $\delta$, $\beta$, and $\gamma$. These subunits can assemble in varying ratios, often dictated by the tissue source. Varying the relative ratios of the subunits confers unique kinetics and pharmacology upon these channels. Without intending to be limited to any particular theory or mechanism of action, it is believed that the $\delta$ subunit replaces the $\alpha$ subunit in many tissues, and that such a substitution may modify particularly the pharmacology of the channel.

Single cell quantitative PCR with specific reference to estimation of the ratios of ENaC subunits. While there is no guarantee of a one-to-one correspondence between amount of message and amount of protein, Q-PCR is one tool available for estimation of ENaC ratio. Assuming a salty taste cell is active, it is likely to have a number of copies of a particular subunit. It is likely that the ratio of message copies will be at least approximately that of the protein products. Quantitative single cell PCR can be used to gain a semi-quantitative picture of the relative abundance of message for any proteins of interest. The procedure, although theoretically straight forward, presents a number of challenging obstacles. With taste cells, for example, RNA quality can be problematic because the time-consuming procedure currently used to obtain isolated cells (see above) is conducive to destruction of RNA. To be confident in the experimental technique, the following procedure can be carried out: (1) Design several unique primer pairs for each gene of interest, using only those that have almost identical efficiency under the same PCR conditions for every gene of interest. (2) Construct a primer set (mixture of primer pairs) from the appropriate pairs above that registers as a blank when used in a water control PCR reaction. (3) Collect individual cells (as above) into an RNase-free environment, lyse the cell and reverse transcribe the single cell mRNA content using a commercially available kit. (4) Run a limited (10-25) number of cycles of the first stage PCR with the primer set and condition above, so that all of the reactions are in a linear amplification phase. (5) Dilute the above reaction (100×-1000×), and use an aliquot as template along with a single pair of primers from the set above and perform the second stage of PCR (in duplicate/triplicate) using a Q-PCR machine. (6) A relative quantification method is used for data analysis. Normalization is based on amplification of a genomic DNA that is not translated/transcribed of which there is, by definition, one copy of the gene. The differences in gene expression can be determined by comparing ratio ($\Delta Ct$ between target gene and genomic reference sequence in sample) differences ($\Delta\Delta Cts$, the differences of $\Delta Cts$ between two samples).

A taste bud cell containing message for human ENaC subunits $\delta$, $\beta$, and $\gamma$, but no message for $\alpha$ was apparent. The Q-PCR trace of this analysis is shown in FIG. 7. From this single cell, it can be concluded that the ENAC of that cell is of multimeric structure, $\delta 61 \beta 1 \gamma 1$. However, as these traces are not normalized, the definitive structure may have a different stoichiometric ratio. The best evidence, however, suggests that the human salty taste receptor is composed of $\delta 1 \beta 1 \gamma 1$.

Once sequence confirmation is obtained, the recombinant plasmid can be used as the substrate in a process known as in vitro protein expression (IVPE). This procedure, be it either cell driven or a cell-free system, allows generation of large amounts (mM) of desired protein, in this case, ENaC subunits, $\delta$, $\alpha$, $\beta$, and $\gamma$. A Western blot can be used to confirm the identity of the manufactured protein. Analysis of the reaction mixture using an antibody to the protein (a Western blot) is used to confirm that the desired protein has indeed been obtained.

The desired protein can be isolated and purified. Purification of the protein by affinity chromatography involves chemically linking an antibody to the protein with a column matrix such as Sephadex. Passing the IVPE reaction mixture through the column results in binding of the protein to its antibody on the column. Elution of the column with an appropriate reagent yields the enriched protein. The protein eluate can be quantified by measuring total nitrogen, as in the Kjeldahl procedure. This measure of total nitrogen content is then compared to the protein's absorption at 280 nm to calculate an absorption coefficient. From this point, absorption at 280 nm becomes a convenient and accurate measure of protein concentration.

Knowing the actual concentration of each subunit of the ENaC allows the combination of these subunits in specific ratios, these having been estimated by the Q-PCR of single cells. As these proteins are membrane associated, they will require some amount of detergent to remain soluble. While their being soluble is required for combining them in specific ratios, detergent will destroy the lipid bilayer into which they need to be reconstituted to measure activity. Thus, reconstitution of the lipid bilayer with the isolated proteins requires that any detergent be removed. Detergent can be removed by any means suitable in the art, such as dialysis as described herein. Reconstitution of isolated proteins into lipid membranes has been described (Grosvenor, W et al. (2004) *BMC Neurosci.* 5:2202-5), and summarized in the examples above. Because the subunits for human ENaC are synthesized, an advantage is gained as careful control over the composition an ratios of any putative salt taste receptor subunits can be exerted.

The present invention is not limited to the embodiments described and exemplified above, but is capable of variation and modification within the scope of the appended claims.

What is claimed:

1. A method for identifying modulators of the human salty taste receptor, comprising:
    assembling at least one salty taste receptor in a planar lipid bilayer, wherein the salty taste receptor comprises at least one beta subunit, at least one gamma subunit, and at least one delta subunit;
    contacting the human salty taste receptor with a test compound in the presence of sodium or lithium; and
    determining a modulation of the biological activity of the human salty taste receptor in the presence of the test compound relative to the biological activity of the human salty taste receptor in the absence of the test compound.

2. The method of claim 1, wherein said delta subunit comprises the amino acid sequence of SEQ ID NO:12.

3. The method of claim 1, further comprising contacting the human salty taste receptor with an epithelial sodium ion channel antagonist.

4. The method of claim 1, wherein at least two subunits of human salty taste receptor are present in the lipid membrane at differing ratios relative to each other.

5. A method according to claim 1 adapted for high throughput screening.

6. The method of claim 1, wherein the planar lipid bilayer is formed from phospholipids.

7. The method of claim 1, wherein the planar lipid bilayer is formed from synthetic phospholipids.

8. The method of claim 1, wherein the planar lipid bilayer comprises at least one phospholipid including phosphatidylcholine, phoshpatidylethanolamine, phostphatidylserine, phosphatidylglyine, phosphatidylinositol, sphingomyelin, cholesterol, cardiolipin, or a homolog, analog, or derivative thereof.

9. The method of claim 1, wherein the planar lipid bilayer is formed from a mixture of 1,2-dioleoyl-sn-glycero-3-phosphoethanolamine and 1,2-dioleoyl-sn-glycero-3-phosphocholine.

10. The method of claim 1, wherein the planar lipid bilayer is prepared by admixing a liposome comprising at least one phospholipid with an epithelial sodium ion channel or epithelial sodium ion channel subunits.

11. The method of claim 10 comprising
    dissolving the epithelial sodium ion channel or epithelial sodium ion channel subunits an aqueous buffer comprising at least one detergent,
    incubating the liposome with the epithelial sodium ion channel or epithelial sodium ion channel subunit for a sufficient amount of time to permit assembly of the epithelial sodium ion channel or epithelial sodium ion channel subunits in the liposome, and
    removing the at least one detergent.

* * * * *